(12) United States Patent
Doran et al.

(10) Patent No.: US 6,896,696 B2
(45) Date of Patent: May 24, 2005

(54) FLEXIBLE AND EXPANDABLE STENT

(75) Inventors: Burns P. Doran, Albertville, MN (US); Jason Todd Lenz, Maplewood, MN (US); Graig L. Kveen, Maple Grove, MN (US); Timothy Samuel Girton, Minneapolis, MN (US); James F. Hemerick, Champlin, MN (US); Timothy J. Ley, Shoreview, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 393 days.

(21) Appl. No.: 09/957,983

(22) Filed: Sep. 21, 2001

(65) Prior Publication Data

US 2002/0055770 A1 May 9, 2002

Related U.S. Application Data

(63) Continuation-in-part of application No. 09/197,278, filed on Nov. 20, 1998.
(60) Provisional application No. 60/234,548, filed on Sep. 22, 2000, provisional application No. 60/272,651, filed on Mar. 1, 2001, and provisional application No. 60/272,906, filed on Mar. 1, 2001.

(51) Int. Cl.[7] ............................................. A61F 29/00
(52) U.S. Cl. ........................................................ 623/1.15
(58) Field of Search ................................ 623/1.1–1.22; 606/108, 191, 192, 194, 195, 198; 600/1–6

(56) References Cited

U.S. PATENT DOCUMENTS

| | | | | |
|---|---|---|---|---|
| 5,356,423 A | 10/1994 | Tihon et al. | ................. | 606/194 |
| 5,591,197 A | 1/1997 | Orth et al. | ................. | 606/198 |
| 5,609,627 A | * 3/1997 | Goicoechea et al. | ......... | 128/898 |
| 5,697,971 A | 12/1997 | Fischell et al. | ................. | 623/1 |
| 5,718,713 A | 2/1998 | Frantzen | ..................... | 606/198 |

(Continued)

FOREIGN PATENT DOCUMENTS

| | | |
|---|---|---|
| DE | 297 01 758 | 3/1997 |
| DE | 297 02 671 U1 | 4/1997 |
| DE | 297 08 689 U1 | 7/1997 |
| DE | 297 08 879 U1 | 7/1997 |
| DE | 297 16 476 U1 | 2/1998 |
| DE | 298 16 878 U1 | 12/1998 |
| EP | 0 364 787 B1 | 4/1990 |
| EP | 0 540 290 A2 | 5/1993 |
| EP | 0 541 443 A1 | 5/1993 |

(Continued)

OTHER PUBLICATIONS

U.S. Appl. No. 60/076,946, filed Mar. 3, 1998, Tseng et al.

Beyar et al., "The BeStent; The Parallel–Serial Jang Stents", *Handbook of Coronary Stents, Second Edition*, 158–171 &229–234 (1998).

Beyar et al., "Newer Stents: Materials and Designs", *IAGS Proceedings*, 9(5): 363–371 (Jun. 1997).

(Continued)

*Primary Examiner*—Vy Q. Bui
(74) *Attorney, Agent, or Firm*—Vidas, Arrett & Steinkraus

(57) ABSTRACT

In one embodiment of the invention, a stent may be provided comprising a first undulating band comprising a series of alternating first peaks and first troughs and a second undulating band comprising a series of alternating second peaks and second troughs. The first undulating band has a first wavelength and a first amplitude and the second undulating band has a second wavelength and a second amplitude where the second amplitude is different from the first amplitude and the second wavelength is different from the first wavelength. A plurality of longitudinally oriented first connectors extend between the first peaks and second peaks.

19 Claims, 50 Drawing Sheets

FOREIGN PATENT DOCUMENTS

| | | |
|---|---|---|
| EP | 0 606 165 A1 | 7/1994 |
| EP | 0 821 920 A1 | 2/1998 |
| EP | 0 876 806 A1 | 11/1998 |
| JP | 6-41745 | 3/1994 |
| WO | WO 94/17754 | 8/1994 |
| WO | 92/26689 | 9/1996 |
| WO | 97/04721 | 2/1997 |
| WO | 97/14375 | 2/1997 |
| WO | 97/25937 | 7/1997 |
| WO | 97/32543 | 9/1997 |
| WO | 97/32544 | 9/1997 |
| WO | 97/33534 | 9/1997 |
| WO | 97/40780 | 11/1997 |
| WO | 97/40781 | 11/1997 |
| WO | 97/40782 | 11/1997 |
| WO | 97/40783 | 11/1997 |
| WO | 97/40874 | 11/1997 |
| WO | 98/20810 | 5/1998 |

OTHER PUBLICATIONS

Roguin et al., Acute and 30–Day Results of the Serpentine Balloon Expandable Stent Implantation in Simple and Complex Coranary Arterial Narrowings, *The American Journal of Cardiology*, 80:1155–1162 (Nov. 1997).

Roguin et al., "beStent—the serpentine balloon expandable stent: review of mechanical properties and clinical experience", *Artif Organs*, 22(3):243–249 (Mar. 1998).

*Manufacturing Processes for Engineering Materials,* by Serope Kalpakjian, Illinois Institute of Technology, Addison–Wesley Publishing Company, pp. 340.

*A View of Vascular Stents,* by Richard A. Schatz, MD, from the Arizona Heart Institute Foundation, Phoenix, Arizina, *Circulation,* vol. 79, No. 2, Feb. 1989, pp. 445–447.

*The Self–Expanding Mesh Stent,* by Ulrich Sigwart, *Section IV,* Chapter 29, pp. 605–610.

*Engineering Fluid Mechanics, Third Edition,* John A. Roberson and Clayton T. Crowe, pp. 94 and pp. 414–421.

*Cambridge Dictionary of Science and Technology,* Cambridge University Pressp. 128.

*Improved Dilatation Catheter Balloons,* by Stanley B. Levy, Ph.D., *Journal of Clinical Engineering,* vol. 11, No. 4, Jul.–Aug. 1986, pp. 291–296.

*Self–expanding Stainless Steel Biliary Stents*, by Harold G. Coons, MD, *Radiology 1989,* vol. 170, No. 3, Part 2, pp. 979–983.

Technical Note Entitled *Modifications of Gianturco Expandable Wire Stents,* by Barry T. Uchida et al., *AJR,* vol. 150, May 1988, pp. 1185–1187.

Brochure from Cook Incorporated regarding Gianturco–Rosch Biliary Z–Stents™ (1989).

*Expandable Biliary Endoprosthesis: An Experimental Study,* by Carnasco et al.,*AJR,* vol. 145, Dec. 1985, pp. 1279–1282.

*Gianturco Expandable Metallic Biliary Stents: Results of a European Clinical Trial,* by Irving et al., *Interventional Radiology,* vol. 172, No. 2, Aug. 1989, pp. 321–326.

*Tracheobronchial Tree: Expandable Metallic Stents Used in Experimental and Clinical Applications, Work In Progress,* by Wallace et al., *Radiology,* Feb. 1986, pp. 309–312.

Brochure Entitled *AVE Micro Stent*™, Instructions for Use, by Applied Fascular Engineering, Inc., pp. 1–15.

Brochure Entitled *Micro Stent*™, by Applied Vascular Engineering, Inc.

Smart™ Stent Brochure, Cordis, A Johnson & Johnson company.

U.S. Appl. No. 09/197,278, filed Nov. 20, 1998, Brown et al.
U.S. Appl. No. 60/234,548, filed Sep. 22, 2000, Girtron et al.
U.S. Appl. No. 60/272,651, filed Mar. 1, 2001, Doran et al.
U.S. Appl. No. 60/272,906, filed Mar. 1, 2001, Doran et al.

* cited by examiner

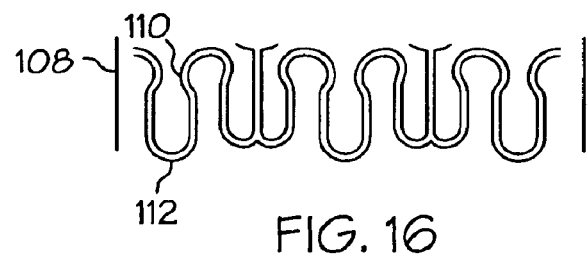
FIG. 16
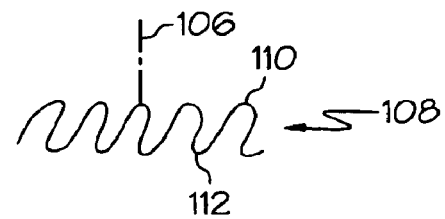
FIG. 17
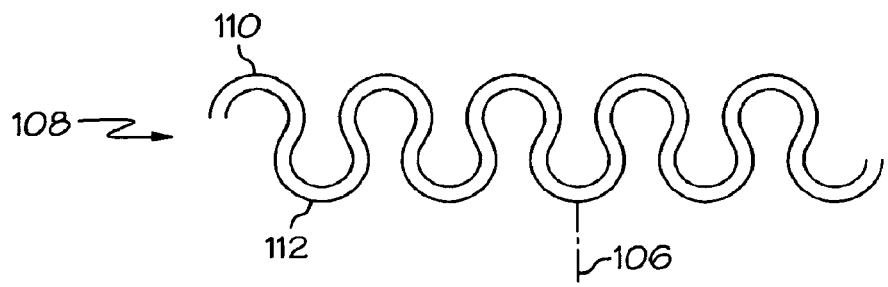
FIG. 18
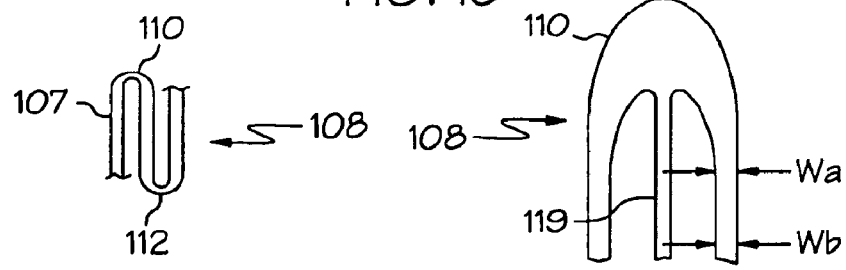
FIG. 19
FIG. 20
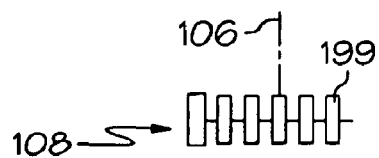
FIG. 21
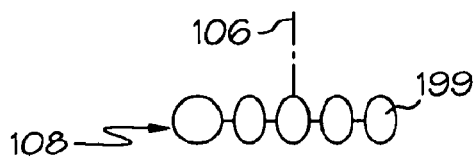
FIG. 22

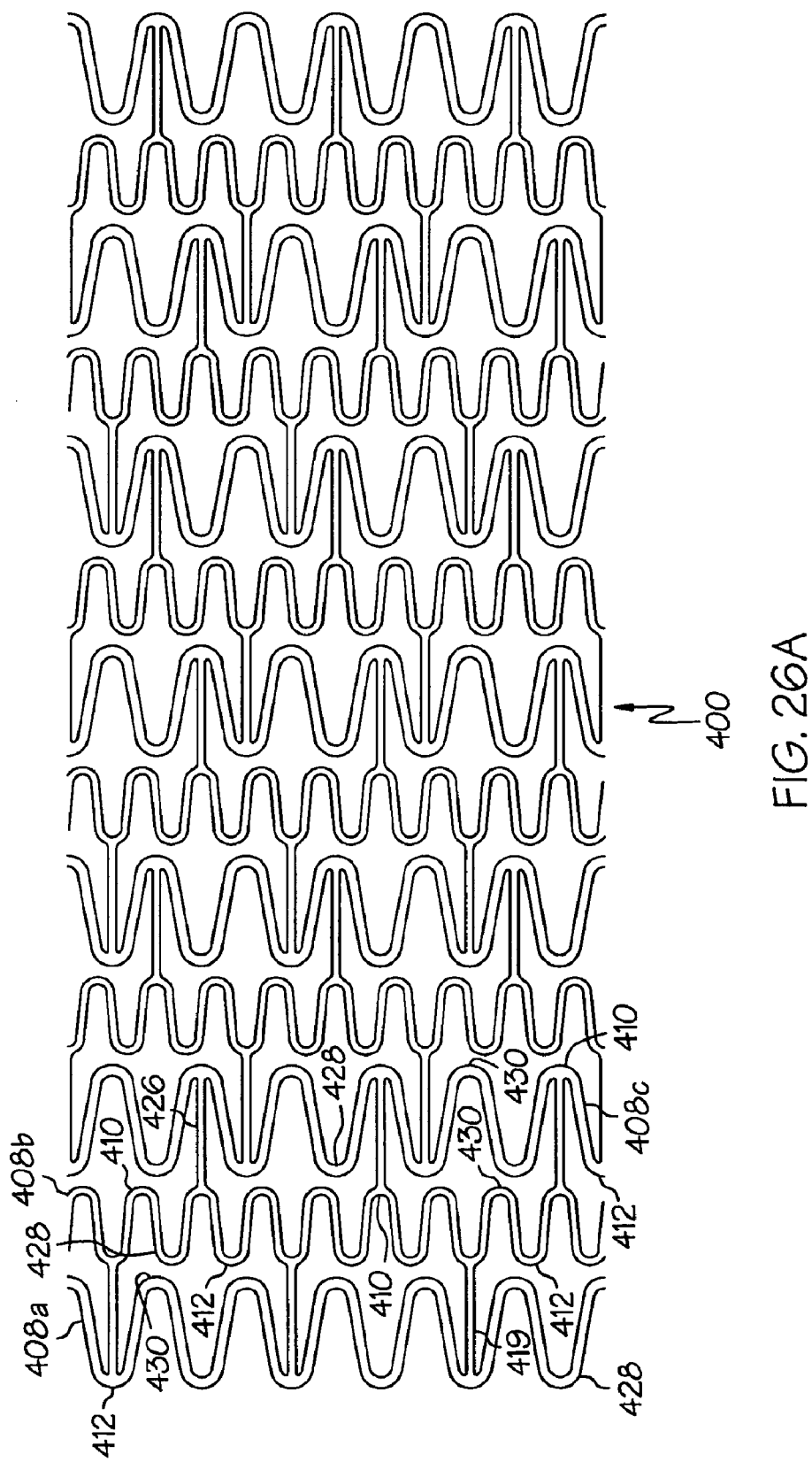

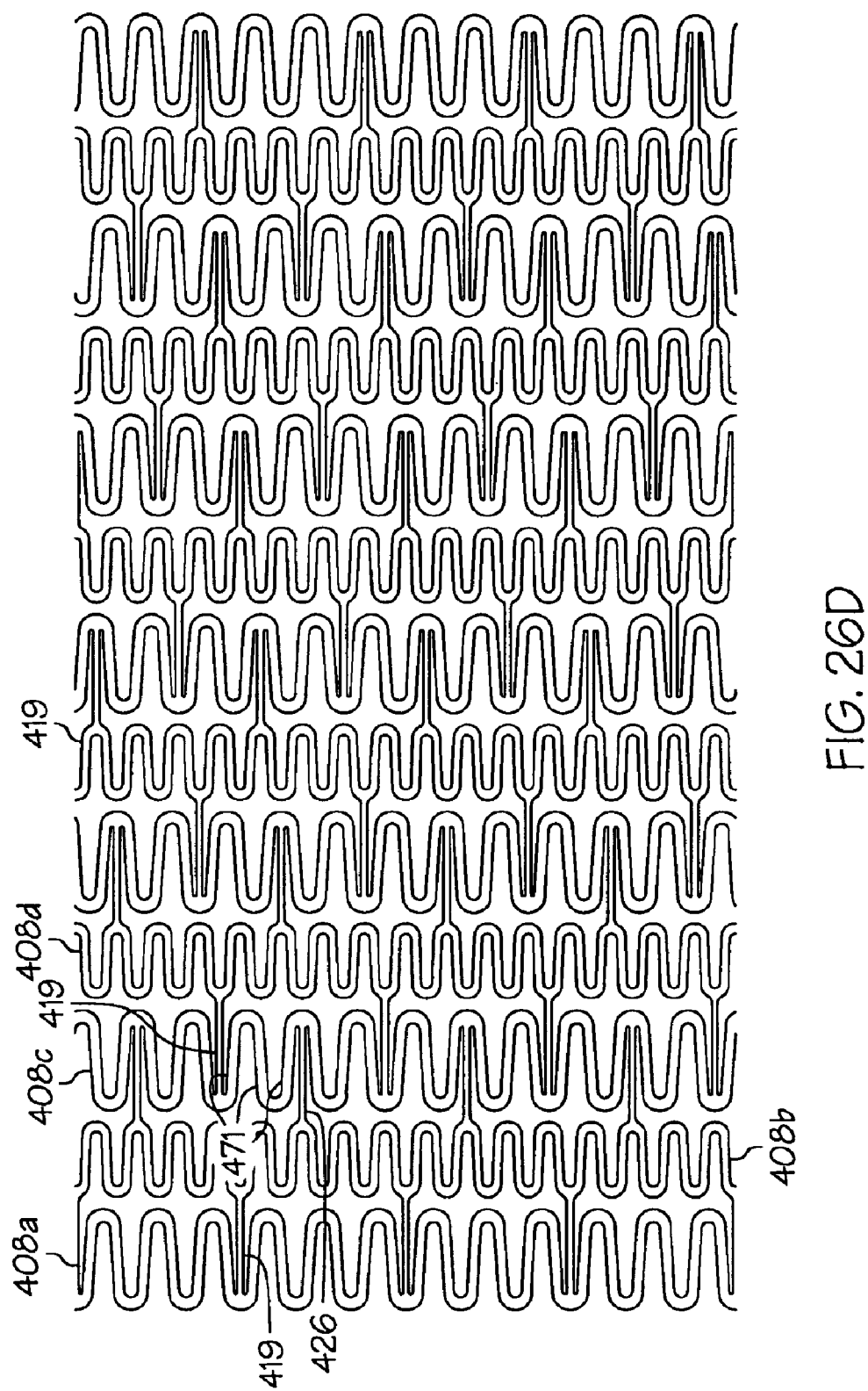

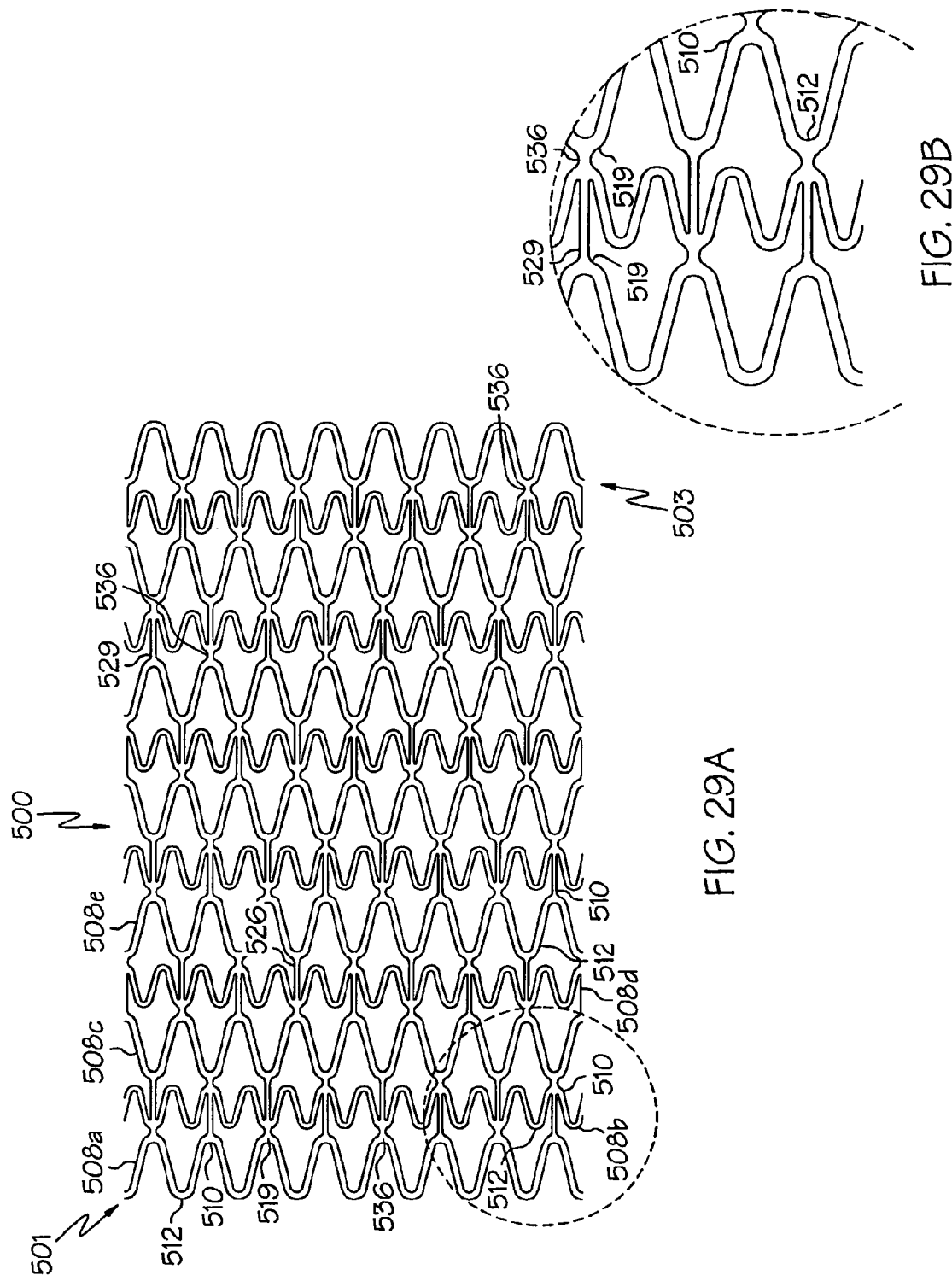

FLEXIBLE AND EXPANDABLE STENT

RELATED APPLICATIONS

The instant application is a continuation-in-part of U.S. application Ser. No. 09/197,278 filed Nov. 20, 1998, and claims the benefit of U.S. provisional application 60/234,548, filed Sep. 22, 2000, U.S. provisional application 60/272,651 filed Mar. 1, 2001 and U.S. provisional application 60/272,906 filed Mar. 1, 2001, all of which are incorporated herein in their entirety by reference.

BACKGROUND OF THE INVENTION

The use of stents in bodily lumen is well known. A stent is typically delivered in an unexpanded state to a desired location in a bodily lumen and then expanded. The stent may be expanded via the use of mechanical device such as a balloon or the stent may be self-expanding.

Because a stent often must be delivered through tortuous anatomy, it is desirable for the stent to be flexible. It is also desirable for the stent to exhibit high scaffolding in the expanded state. In general, however, as stent flexibility is increased, scaffolding is decreased and similarly, as scaffolding is increased, flexibility is decreased.

There remains a need for a stent having a high degree of flexibility in the unexpanded state and high scaffolding in the expanded state.

The contents of U.S. provisional applications 60/234,548, 60/272,651 and 60/272,906 as well as U.S. application Ser. No. 09/197,278 are incorporated herein in their entirety by reference.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the invention is directed to a stent having a proximal end and a distal end comprising a first undulating band and a second undulating band. The first undulating band comprises a series of alternating first peaks and first troughs, with the first peaks oriented in a distal direction and the first troughs oriented in a proximal direction. The first undulating band has a first wavelength and a first amplitude. The second undulating band comprises a series of alternating second peaks and second troughs with the second peaks oriented in a distal direction and the second troughs oriented in a proximal direction. The second undulating band has a second wavelength and a second amplitude, the second amplitude different from the first amplitude and the second wavelength different from the first wavelength. A plurality of longitudinally oriented first connectors extend between first peaks and second peaks. Optionally, the width of the first and second undulating bands may differ.

The stent may optionally comprise additional undulating bands. To that end, a third undulating band comprising a series of alternating third peaks and third troughs may be present. The third undulating band has a third wavelength and a third amplitude. The third wavelength and amplitude may be different from the first and/or second wavelengths and amplitudes. Desirably, the third wavelength is equal to the first wavelength and the third amplitude is equal to the first amplitude. More desirably, the third undulating band is identical in structure to the first undulating band. A plurality of longitudinally oriented second connectors may extend between second troughs on second undulating bands and third troughs on third undulating bands. A fourth undulating band having alternating fourth peaks and troughs may also be provided. Desirably the wavelength and amplitude of the fourth band is identical to that of the second band. More desirably, the structure of the fourth undulating band is identical to the structure of the second undulating band.

Desirably, the stent comprises a plurality of first and second undulating bands alternating along the length of the stent.

The invention is also directed to a stent comprising at least one first expansion cell. The first expansion cell has a proximal end, a distal end, a first side extending between the proximal and distal ends, and a second side opposite the first side and extending between the proximal and distal ends. The proximal end of the cell consists of an undulating segment having a first trough opening in a distal direction, a second trough opening in a distal direction, and a first peak opening in a proximal direction. The first peak is disposed between the first trough and the second trough. The distal end of the cell consists of an undulating segment having a first half peak and a second half peak, three troughs opening in a distal direction and two peaks opening in a proximal direction. The peaks and troughs alternate with one another and are disposed between the first and second half peaks. The first and second sides are substantially straight, longitudinally extending members. Desirably, the stent comprises a plurality of first expansion cells. The first expansion cells may be arranged in circumferential bands extending about the periphery of the stent. The stent may further comprise second expansion cells where the second expansion cells are mirror images of the first expansion cells. One of the proximal and distal ends of the first and/or second expansion cells may be of a different width than the other end of the cell.

Additional details and/or embodiments of the invention are discussed below.

BRIEF DESCRIPTION OF THE SEVERAL VIEWS OF THE DRAWING(S)

FIGS. 15–18 show undulating bands that may be used in the inventive stents.

FIGS. 19 and 20 show portions of undulating bands that may be used in the inventive stents.

FIGS. 21–22 show closed bands that may be used in the inventive stents.

FIGS. 26a–e are flat patterns of inventive stents.

FIGS. 27–29a are flat patterns of inventive stents.

FIG. 29b shows an enlarged portion of the inventive stent of FIG. 29a.

FIGS. 30a–c and 31–35a are flat patterns of inventive stents.

Figure 35B:
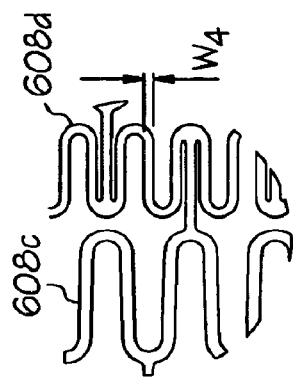
Figure 35C:
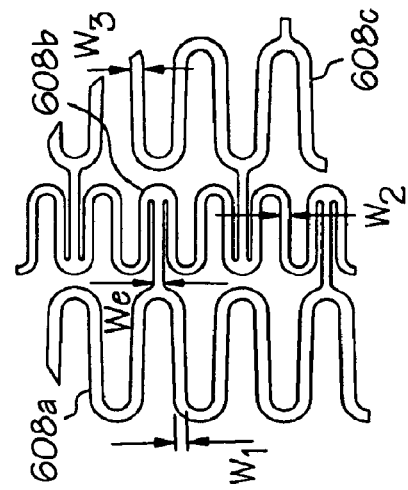
Figure 35A:
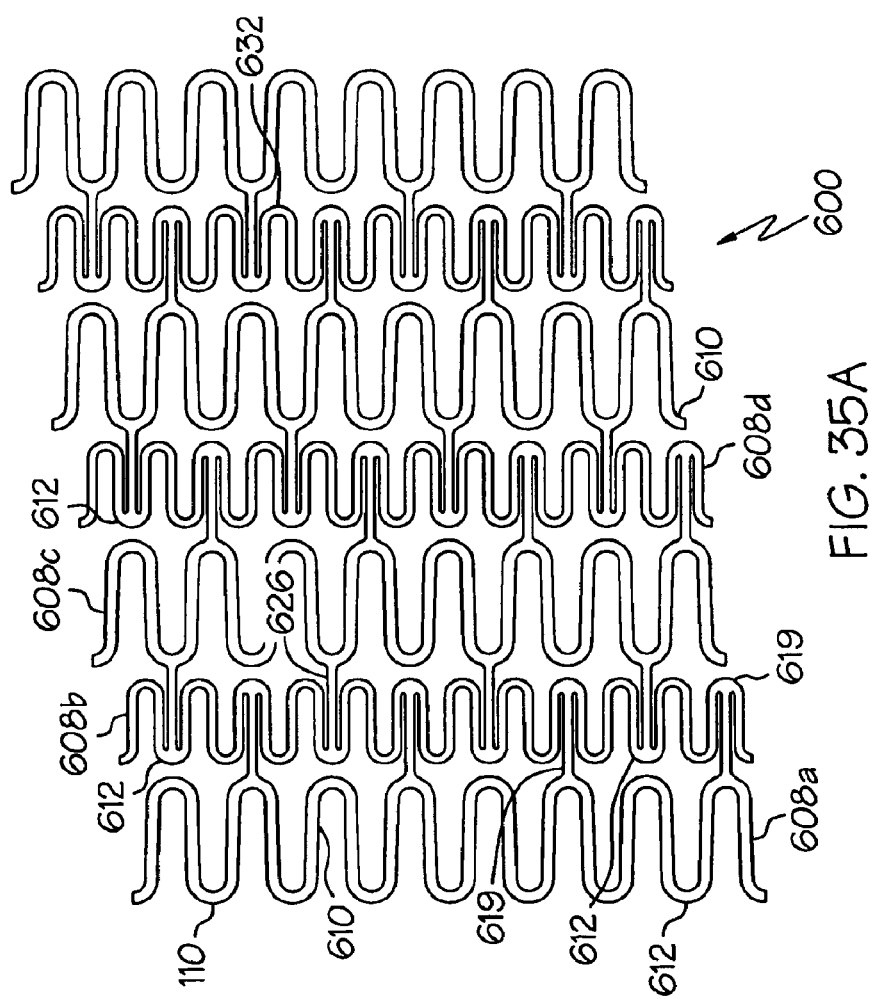

FIG. 35b shows enlarged portion B of the inventive stent of FIG. 35a.

FIG. 35c shows enlarged portion C of the inventive stent of FIG. 35a.

Figure 36B:
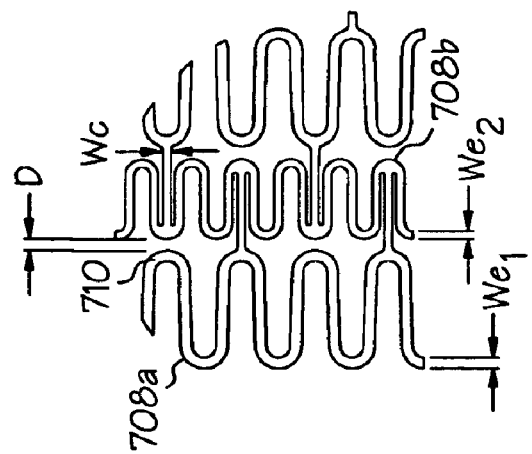
Figure 36A:
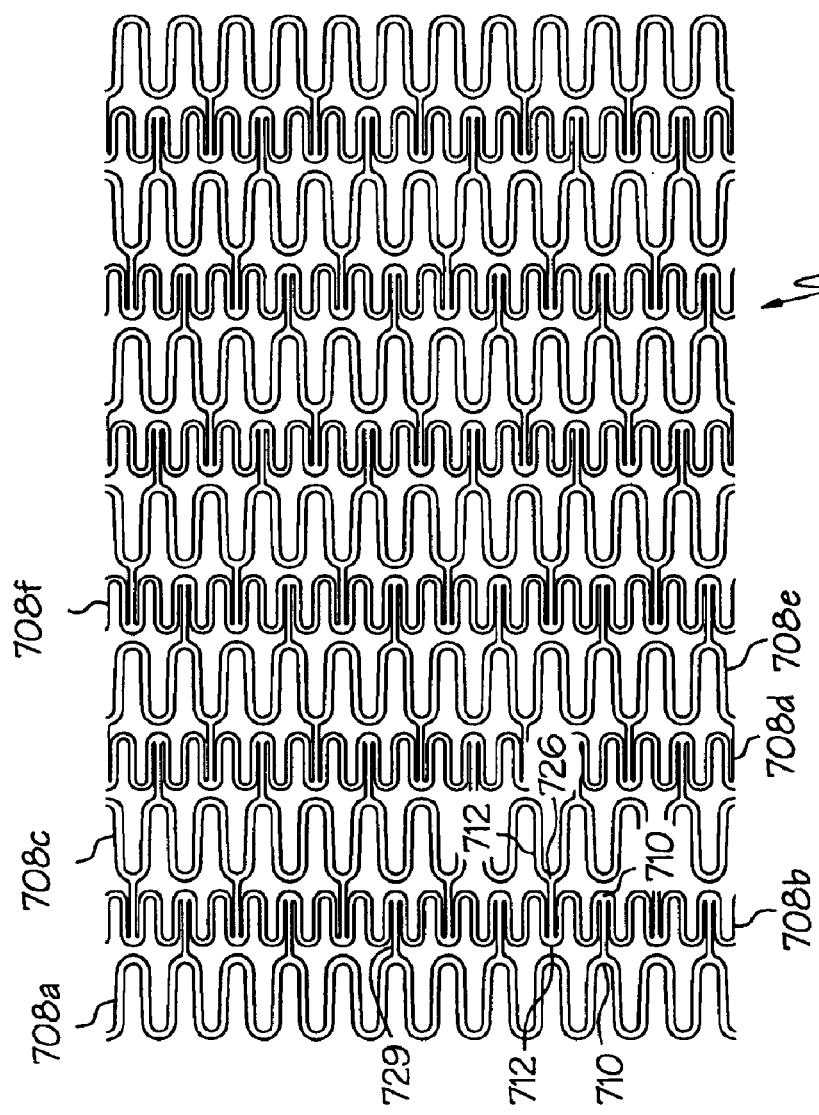

FIG. 36a is a flat pattern of an inventive stent.

FIG. 36b shows enlarged portion A of the inventive stent of FIG. 36a.

FIGS. 37–41a are flat patterns of inventive stents.

Figure 41B:
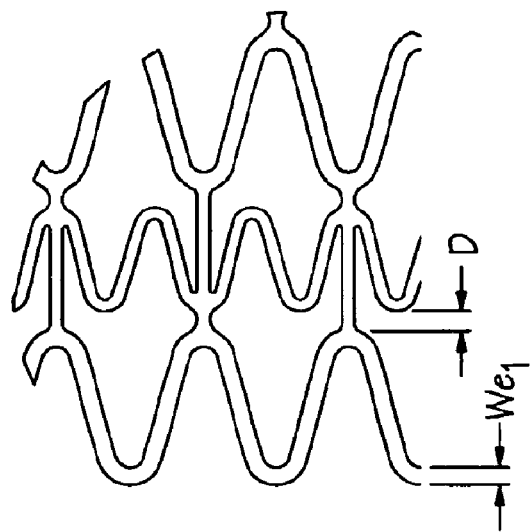
Figure 41A:
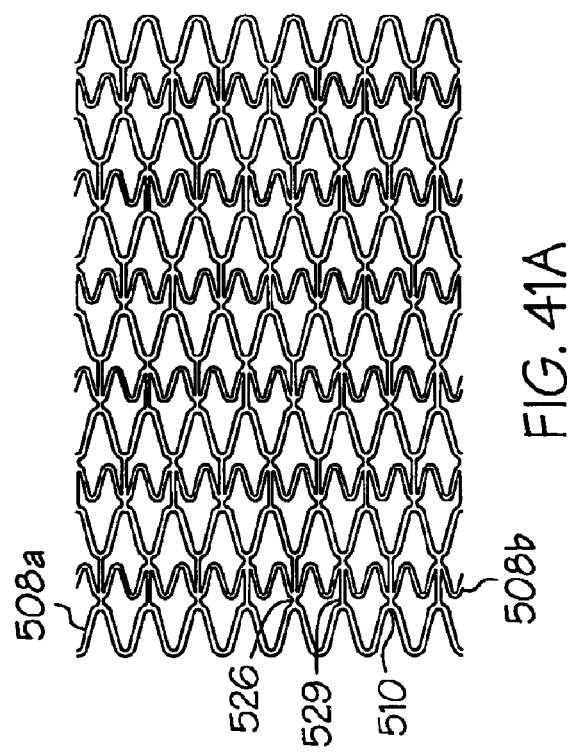

FIG. 41b shows enlarged portion A of the inventive stent of FIG. 41a.

FIGS. 42–47 are flat patterns of inventive stents.

Figure 48:
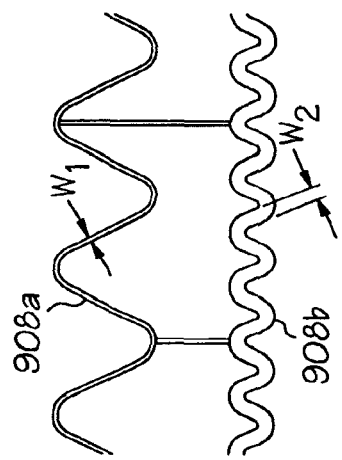

FIG. 48 shows a portion of an inventive stent.

FIGS. 49–53 show flat patterns of additional inventive stents.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

The present invention, in one embodiment, is directed to stents having patterns such as those shown generally at 100 in FIGS. 1–4. Stent 100 has a proximal end 102, a distal end 104 and a flow path therethrough along a longitudinal axis 106. Stent 100 comprises a first undulating band 108a comprising a series of alternating first peaks 110a and first troughs 112a. First peaks 110a are oriented in a distal direction and first troughs 112a are oriented in a proximal direction. First undulating band 108a is characterized by a first wavelength and a first amplitude.

Stent 100 further comprises a second undulating band 114a comprising a series of alternating second peaks 116a and second troughs 118a. Second peaks 116a are oriented in a distal direction and second troughs 118a are oriented in a proximal direction. Second undulating band 114a is characterized by a second wavelength and a second amplitude. The second amplitude is different from the first amplitude and the second wavelength is different from the first wavelength.

A plurality of longitudinally oriented first connectors 119a extend between first peaks 110a and second peaks 116a. Second peaks 116a from which connectors extend optionally have an enlarged outer radius as compared to second peaks from which no connectors extend.

Stent 100 further comprises a third undulating band 108b comprising a series of alternating third peaks 110b and third troughs 112b and a fourth undulating band 114b comprising alternating fourth peaks 116b and fourth troughs 118b. Third peaks 110b and fourth peaks 116b are oriented in the distal direction and third troughs 112b and fourth troughs 118b are oriented in the proximal direction. The third undulating band has a third wavelength and a third amplitude. Desirably, the third wavelength is equal to the first wavelength and the third amplitude is equal to the first amplitude. More desirably, the third band is identical in structure to the first band as shown in FIGS. 1–4. A plurality of longitudinally oriented second connectors 126 extend between second troughs 118a and third troughs 112b. Second troughs from which connectors extend optionally have an enlarged outer radius relative to second troughs from which no connectors extend. The fourth undulating band has a fourth wavelength and a fourth amplitude. Desirably, the fourth wavelength is equal to the second wavelength and the fourth amplitude is equal to the second amplitude. More desirably, the fourth band is identical in structure to the second band, as shown in FIGS. 1–4. Additional bands may be present. A plurality of longitudinally oriented third connectors 119b extend between third peaks 110b and fourth peaks 116b. Additional undulating bands may be present in the stent. Desirably, as shown in FIGS. 1–8, the undulating bands of the stent alternate between first undulating bands of the first wavelength and first amplitude and second undulating bands of the second wavelength and second amplitude. Other arrangements of undulating bands are also within the scope of the invention as discussed below. For example, one or more first undulating bands may be provided at the proximal and/or distal ends of the stent with the remaining bands being second undulating bands. Similarly, one or more second undulating bands may be provided at the proximal and/or distal ends of the stent with the remaining bands being first undulating bands.

Figure 5:
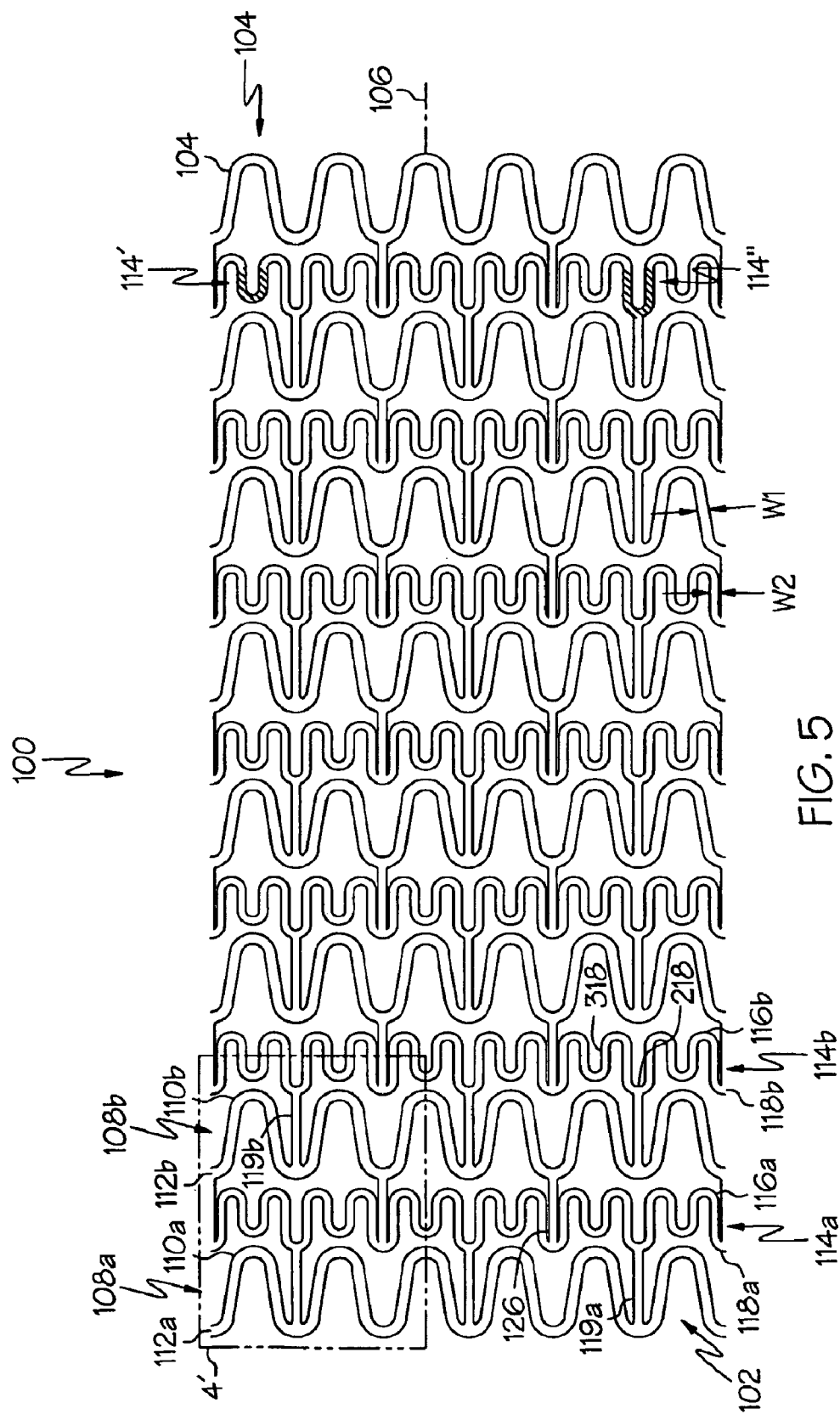

Another inventive stent is shown generally at 100 in FIG. 5. The stent of FIG. 5 comprises a first undulating band 108a with first peaks 110a and first troughs 112a, a second undulating band 114a with second peaks 116a and second troughs 118a, a third undulating band 108b with third peaks 10b and third troughs 112b and a fourth undulating band 114b with fourth peaks 116b and fourth troughs 118b. The first and second undulating bands are connected by three first connectors 119a which extend from first troughs 112a to second troughs 118a. The second and third undulating bands are connected by three second connectors 126 which extend from second troughs 118a to third troughs 112b. The third and fourth undulating bands are connected by third connectors 119b which extend from third troughs 112b to fourth troughs 118b. As shown in FIG. 5, all of the connectors between adjacent undulating bands extend from troughs to troughs. Troughs in each of undulating bands 114a and 114b alternate between longer troughs 218 and shorter troughs 318.

Figure 6:
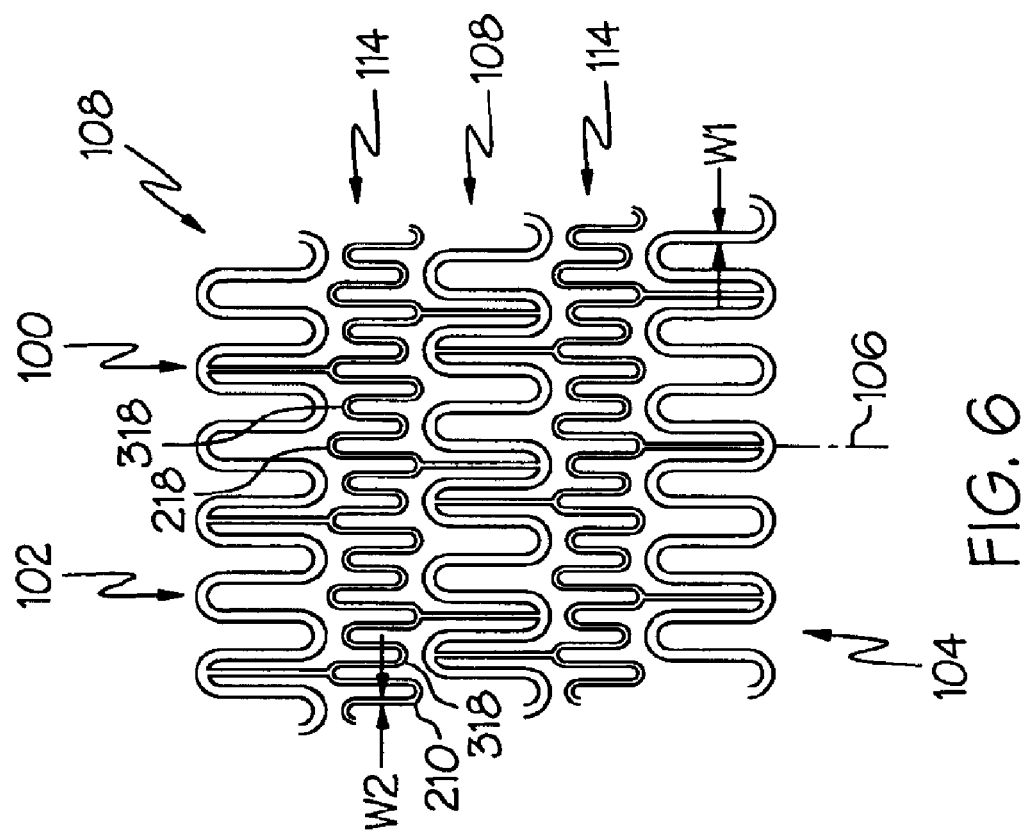

In another embodiment of the invention, as shown in FIG. 6, stent 100 comprises first undulating bands 108 of a first wavelength, width and amplitude and second undulating bands 114 of a second wavelength, width and amplitude. The first wavelength, width and amplitude exceed the second wavelength, width and amplitude. The stent may include both connectors extending from trough to trough and connectors extending from peak to peak as shown in FIG. 6 or may only include connectors extending from trough to trough (or peak to peak). As discussed below, stent 100 includes bands 114 of multiple frequency and amplitude. Troughs in each of undulating bands 114 alternate between longer troughs 218 and shorter troughs 318. Similarly, peaks in each of undulating bands 114 alternate between longer peaks 210 and shorter peaks 310.

Figure 7:
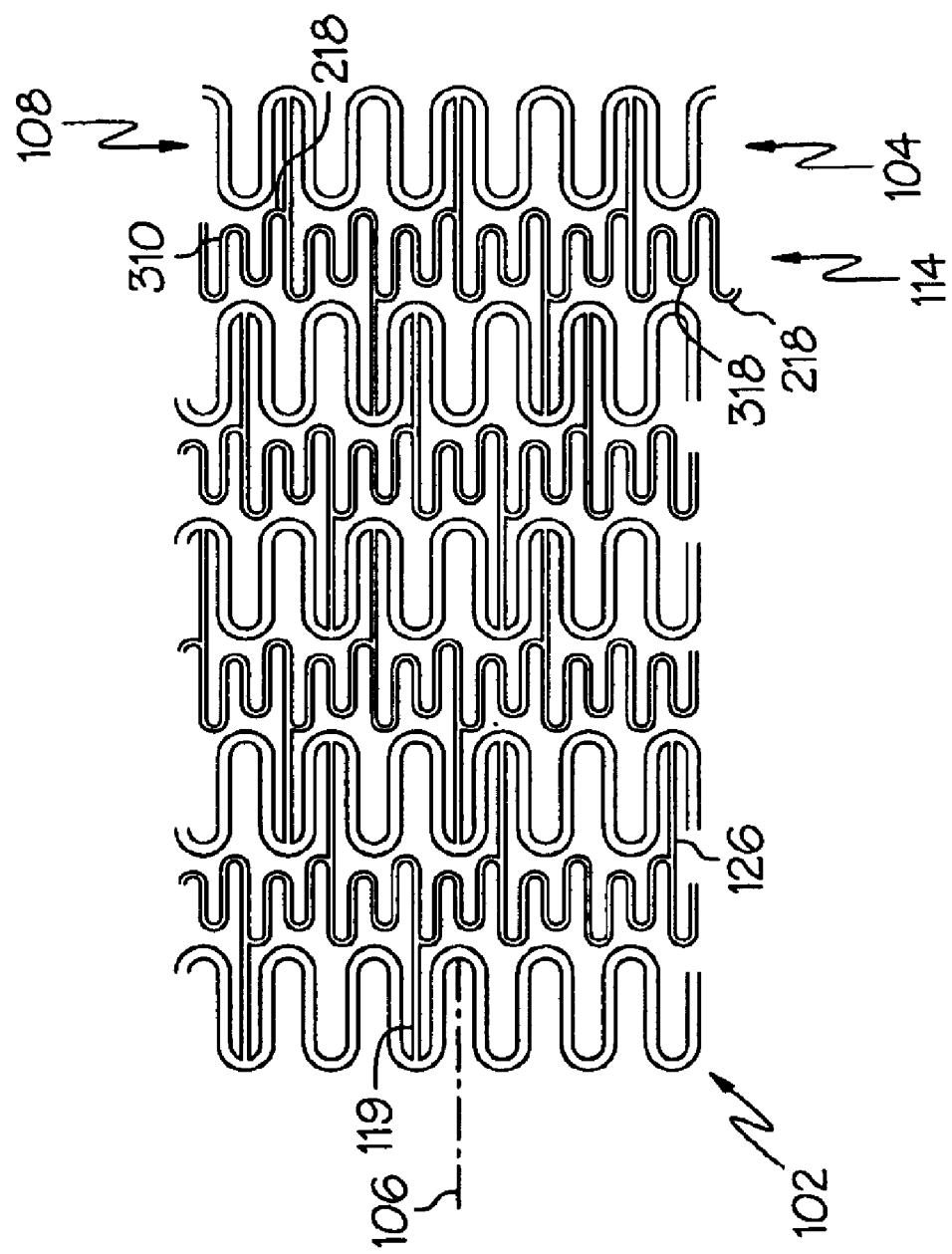

The inventive stent of FIG. 7 is similar to that of FIG. 6 differing in that first and second connectors 119 and 126 extend from the sides of peaks and troughs of undulating bands 114. As shown in FIG. 7, the first and second connectors are collinear with the longitudinally extending portion of the undulating bands from which they extend. The stent of FIG. 7 also is characterized by a different number of first connectors extending between adjacent undulating bands and second connectors extending between adjacent undulating bands. Specifically, adjacent bands which are connected by first connectors have two first connectors extending between the bands. Adjacent bands which are connected by second connectors have three connectors extending therebetween.

Figure 8:
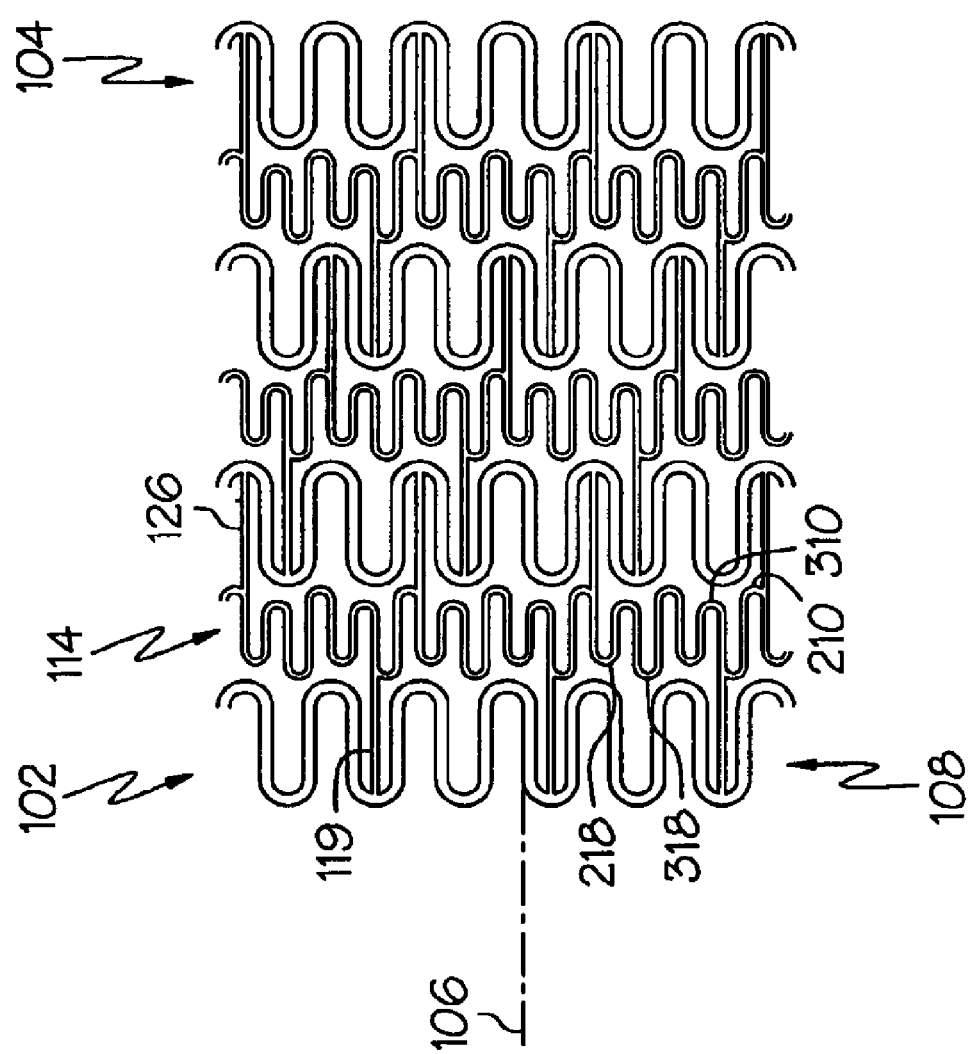

Another inventive stent similar to that of FIG. 7 having connectors extending from the sides of peaks is shown at 100 in FIG. 8. The stent of FIG. 8 differs from the stent of FIG. 7 in that three first connectors 119 connect adjacent first and second undulating bands together while four second connectors 126 connect adjacent second and first undulating bands together.

Figure 1:
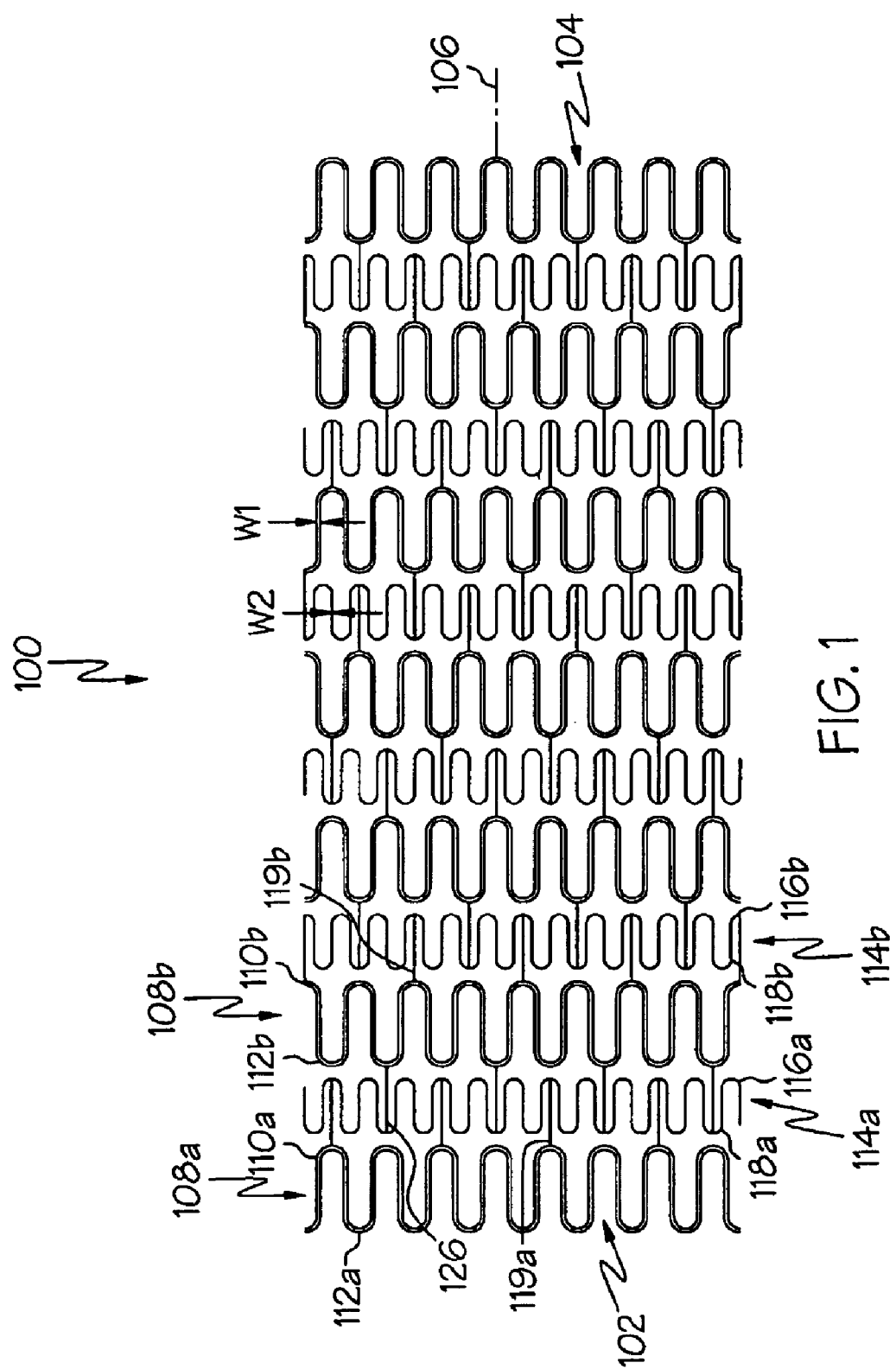
FIGS. 1–8 show flat pattern views of inventive expandable stents.

Desirably, the first and second undulating bands will be of the same total circumferential length, as shown for example, in FIG. 1. The invention also contemplates the use of first and second undulating bands of different total circumferential lengths. For example, the second undulating band may be have a greater total circumferential length than the first undulating band, as shown in FIG. 5. It is also within the scope of the invention for the first undulating band to have a greater circumferential length than the second undulating band.

Desirably, the first undulating band will exhibit the same radial rigidity as the second undulating band. The invention also contemplates embodiments in which the first undulating band exhibits greater radially rigidity as compared to the second undulating band. This may be achieved by making the first bands wider and/or thicker and/or from a stronger material than the undulating second bands. The invention further contemplates embodiments in which the second undulating bands exhibit greater radial rigidity than the first undulating bands.

Figure 2:
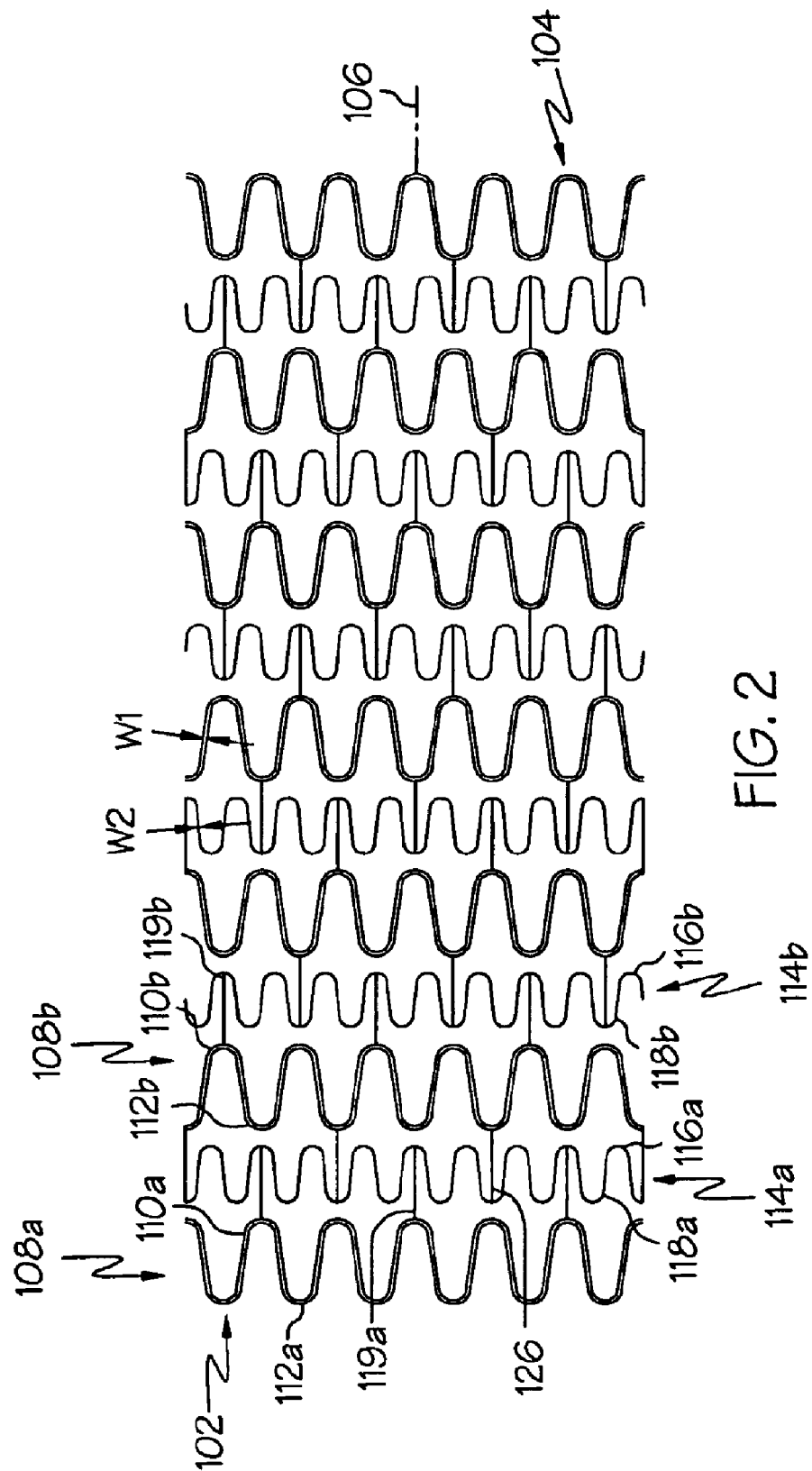
Figure 3:
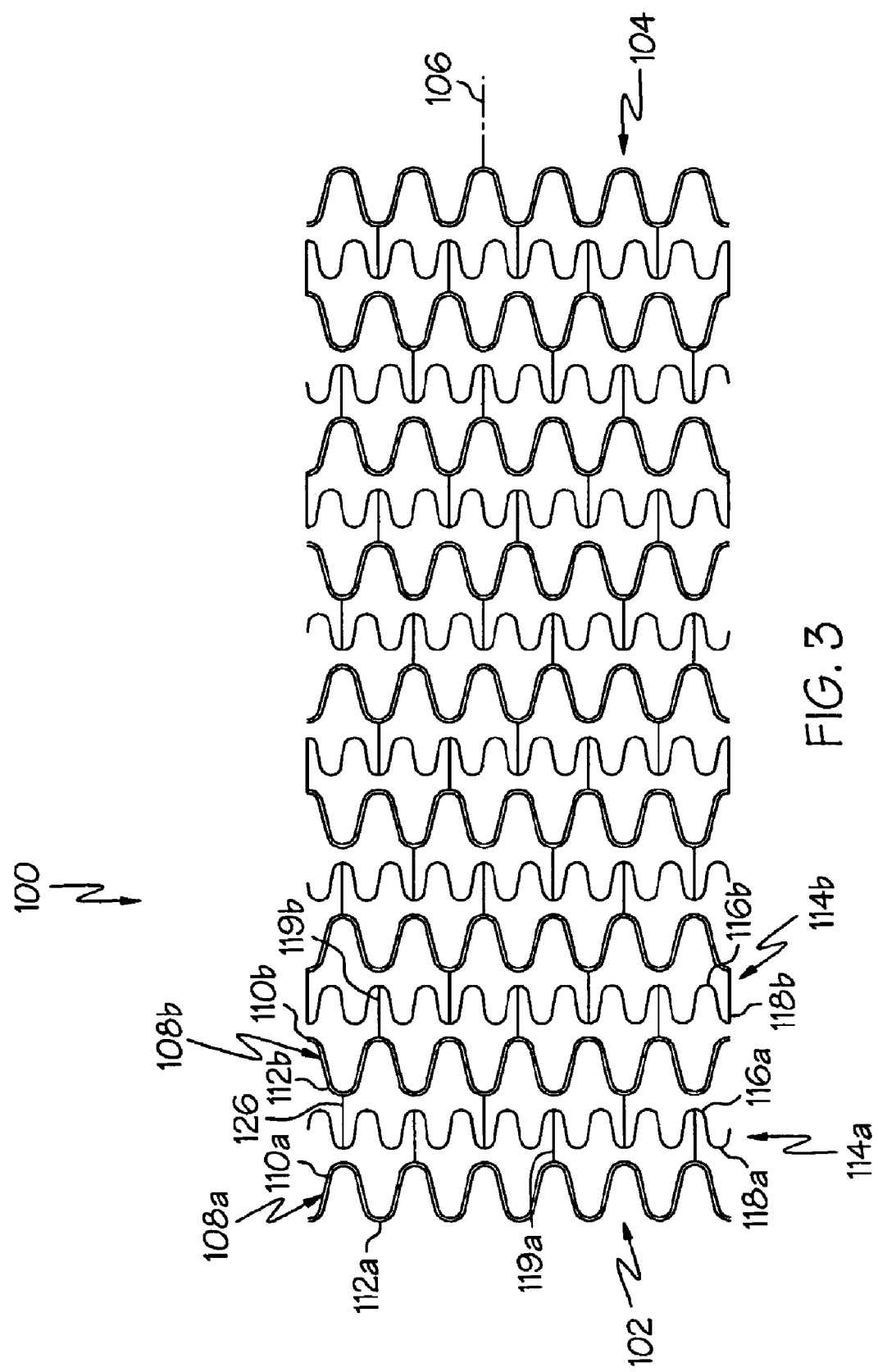

Desirably, as shown for example, in FIGS. 1–8 as well in many of the other figures, the first wavelength will be greater than the second wavelength. More desirably, the ratio of the first wavelength to the second wavelength in any of the embodiment disclosed herein will range from about 1.1:1 to about 5:1 and more desirably from about 1.25:1 to 2.5:1. More desirably still, the ratio will range 1.25:1 to 2:1. Another desirable ratio of wavelengths is about 1.3:1. Even more desirably, as shown in FIG. 1, the wavelength of the first undulating band will be 1.5 times the wavelength of the second undulating band. The ratio of first and second wavelengths of 1.5 corresponds to a ratio of 2 first peaks for every 3 second peaks. The first and second undulating bands of the stent of FIG. 1 contain 8 and 12 peaks, respectively. The invention more generally contemplates any number of peaks and troughs on the first and second bands so long as the wavelengths of the two bands differ. As shown in the stent of FIGS. 2 and 3, six first peaks are present and nine second peaks are present. In another embodiment of the invention, the ratio of the first wavelength to the second wavelength is 4:3 and in yet another embodiment, the ratio of the first wavelength to the second wavelength is 5:4. It is also within the scope of the invention for the first wavelength to be less than the second wavelength.

Also desirably, the first amplitude is greater than the second amplitude. More desirably, the ratio of the first amplitude to the second amplitude will range from about 1.1:1 to about 4:1 and more desirably from about 1.25:1 to about 2.5:1. More desirably still, the ratio will range from about 1.25:1 to about 2:1 Even more desirably, the ratio of amplitudes of first undulating bands to second undulating bands is 1.5:1 as shown in the stent of FIGS. 1–3. Exemplary amplitude ratios are approximately 1.21:1, 1.29:1, 1.3:1 and 1.5:1. The invention also contemplates a stent where the first amplitude is less than the second amplitude.

As shown in FIGS. 1–8, first undulating bands 108a,b have a width $W_1$ in excess of the width $W_2$ of second undulating bands 114a,b. Desirably, the ratio of the width of the first band to the width of the second band will range from about 1:1 to about 2.5:1. Even more desirably, the ratio of the width of the first band to the width of the second band is between about 3:2 to 4:3. In another embodiment of the invention, the first and second undulating bands may be of the same width resulting in bands of different strength. In yet another embodiment of the invention, the second undulating bands (the smaller amplitude bands) may be wider than the first undulating bands (the larger amplitude bands).

In another embodiment of the invention, the first undulating bands may be thicker or thinner than the second undulating bands.

Adjacent first and second undulating bands are connected by connectors extending therebetween. As shown in FIG. 1, four first connectors 119 equally spaced about the periphery of the stent extend between first undulating band 108a and second undulating band 114a. Additional first connectors may be present or fewer first connectors may be present. The stent of FIG. 3, for example, has three first connectors. Similarly, four second connectors 126 equally spaced about the periphery of the stent extend between second undulating band 114a and third undulating band 108b of the stent of FIG. 1. Additional second connectors may be present or fewer second connectors may be present. The stent of FIG. 3 has three second connectors between first undulating bands and second undulating bands. The stent of FIG. 7 has two first connectors first undulating bands and second undulating bands. The stent may have an equal number of first and second connectors. The invention also contemplates providing more or fewer first connectors between first and second undulating bands than second connectors between second and third undulating bands.

Desirably, as shown in FIGS. 1–4, first connectors 119 and second connectors 126 which are circumferentially adjacent are separated by at least one second peak 116 and one second trough 118. Also desirably, first connectors 119 and second connectors 126 which are circumferentially adjacent are separated by at least one first trough 112.

As shown in FIG. 1, the ratio of first peaks to first connectors is 2:1. The ratio of second troughs to second connectors is 3:1. Stents having other ratios of first peaks to first connectors and other ratios of second troughs to second connectors are within the scope of the invention as well. The ratio of first peaks to first connectors can equal or exceed 1:1 and more desirably equal or exceed 1.5:1 and the ratio of second troughs to second connectors will equal or exceed 1:1 and more desirably equal or exceed 3:1.

Figure 9A:
FIGS. 9a–9c show connectors that may be used in the inventive stents.
Figure 9B:
Figure 9C:
Figure 27:
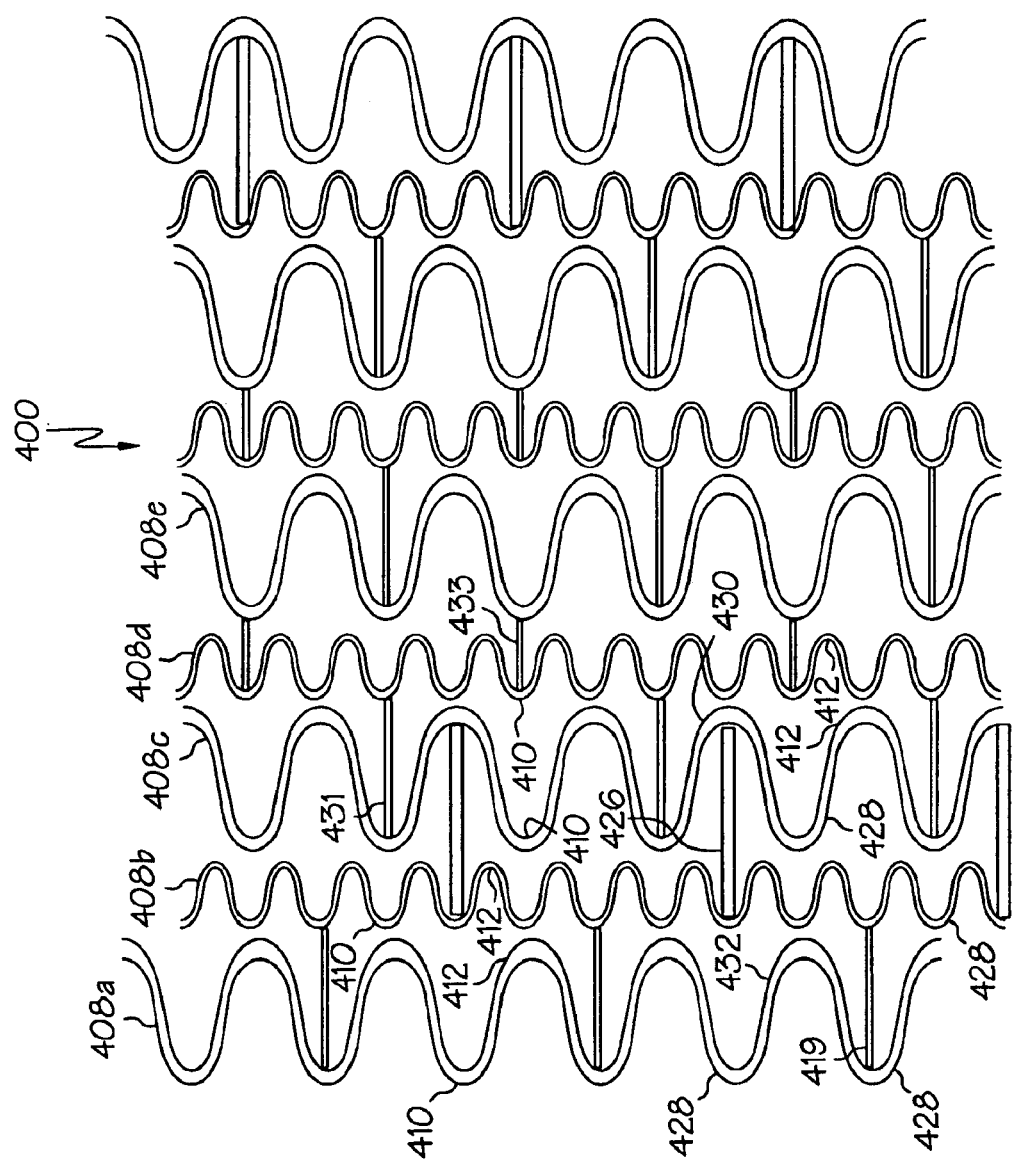

The first and second connectors are desirably straight and extend in a longitudinal direction, as shown in FIGS. 1–8. In another embodiment, the invention is directed to stents having curved first connectors and/or curved second connectors in addition to or in place of straight first and second connectors. To that end, any of the connectors shown in FIGS. 9a–c may also be used, depending on the desired characteristics of the stent. Moreover, the invention contemplates using connecting members whose first and second ends are circumferentially offset relative to one another. An example of such a connecting member is disclosed in WO9626689 and WO0030563. Such a connecting member may be linear or curved.

Where straight connectors are used, as in FIGS. 1–8, the desired gaps between adjacent undulating bands and the width of the bands will determine the length of the first and second connectors. Desirably, the first and second connectors will be of substantially the same length and slightly longer than the amplitude of the second undulating band. The invention also contemplates the first and second connectors being of the same length as the amplitude of the second band or substantially longer than the amplitude of the second band. The first and second connectors may also be provided in a length which differs from that of the first and second amplitudes. It is also within the scope of the invention to provide first and second connectors of different lengths from one another as shown. The first connectors may be longer than the second connectors. In another embodiment, the first connectors may be shorter than the second connectors. The inventive stents may include additional connectors of different lengths. The stent of FIG. 27 includes second connectors 426 which are longer than first connectors 419 and third connectors 431. The stent of FIG. 27 further comprises optional fourth connectors 433 which are shorter than the first, second and third connectors. The stent of FIG. 27 is discussed in greater detail below.

Other embodiments that fall within the scope of the invention include those in which the location of the first and second connecting members along the bands are varied. In the embodiments of FIGS. 1–4, each second connecting member 126 extends distally from a trough 118 on a undulating second band 114 to a trough 112 on an adjacent first undulating band 108 while each first connecting member 119 extends distally from a peak 110 on a undulating first band 108 to a peak 116 on an adjacent second band 114. The invention also contemplates other arrangements of the first and second connecting members between adjacent bands. For example, the second connecting members may extend distally from a peak on a band to a trough on adjacent band and the first connecting members may extend distally from a trough on a band to a peak on an adjacent band. In other embodiments of the invention, the first and second connecting members may extend from any other position along a band in-between a peak and a trough as well.

The invention contemplates stents having as few as one first undulating band and one second undulating band of different wavelength and amplitude and optionally, width, connected by connectors extending from peaks on the first undulating band to peaks on the second undulating band. Desirably, however, a plurality of first undulating bands and second undulating bands alternate with one another along the length of the stent.

The phase arrangement between adjacent bands may be that shown in FIGS. 1–4 or may be any other phase arrangement. Adjacent bands may be arranged so that the peaks of the first undulating bands are aligned with peaks of the second undulating band or may be arranged such that the peaks of the first undulating band do not align with peaks of the second undulating band.

Further as shown in FIGS. 1–8, both the proximal and distal ends of the stent terminate in first undulating bands. The stent may also terminate at both ends in second undulating bands or may terminate at one end with a first undulating band and at the other end with a second undulating band. Desirably, the proximal and distal ends of the stent will terminate in first undulating bands of increased radial rigidity relative to the second undulating bands. Where less radial rigidity at the ends is desired, the proximal and/or distal ends of the stent may have undulating bands exhibiting lower radial rigidity as compared with other undulating bands in the stent. Also desirably, the inventive stent will have a first undulating band in the center of the stent, as shown in FIG. 1.

Figure 4:
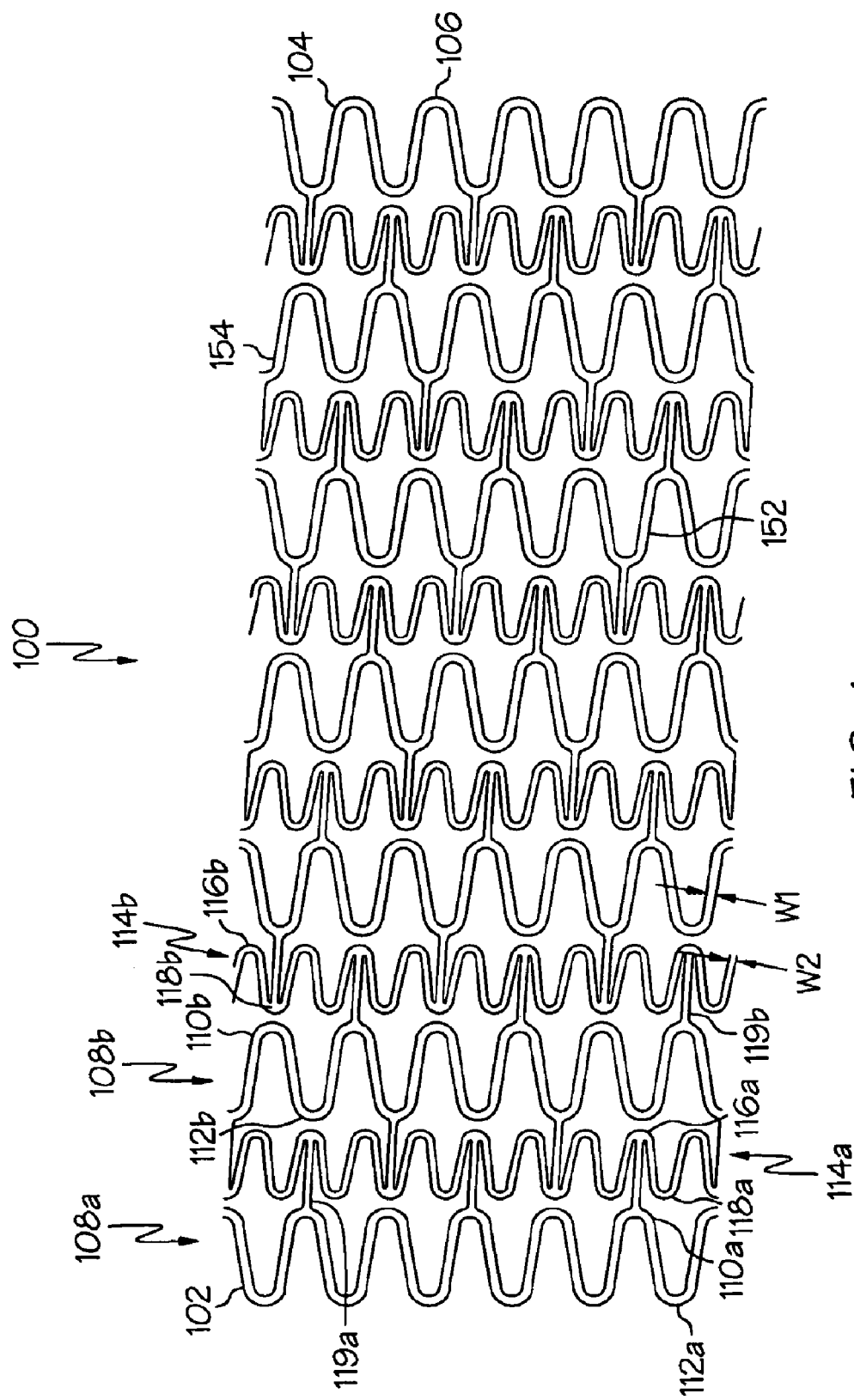
Figure 10:
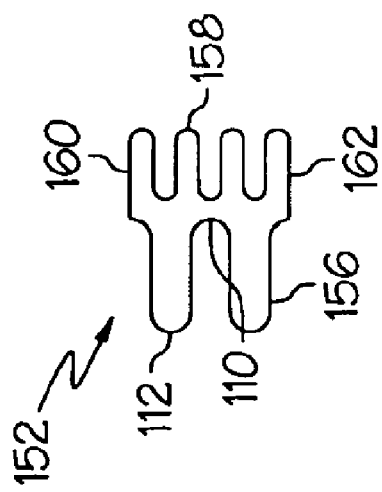

The invention is also directed to a stent comprising at least one and desirably a plurality of first expansion cells 152 and/or second expansion cells 154 as shown in FIGS. 1–4 and highlighted in FIG. 4. First expansion cell 152, shown in greater detail in FIG. 10, has a proximal end 156 and a distal end 158. A first side 160 extends between proximal end 156 and distal end 158 and a second side 162 opposite first side 160 extends between proximal end 156 and distal end 158. The first and second sides are desirably straight. Proximal end 156 comprises an undulating segment having two troughs 112 opening in a distal direction and a peak 110 opening in a proximal direction. Peak 110 is disposed between troughs 112. Distal end 158 comprises an undulating segment having two peaks 116 and three troughs 118, the peaks and troughs alternating with one another and disposed between the first and second sides of the cell. Desirably, first expansion cells are disposed side-by-side in circumferential bands.

Figure 11:
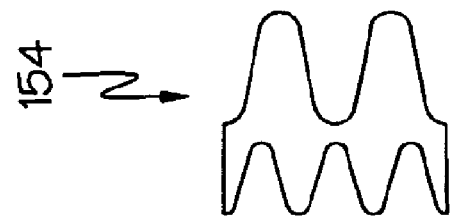
FIGS. 10 and 11 show cells from an inventive stent.

Desirably, the stent further comprises second expansion cells 154 as shown in FIGS. 1–4 and in greater detail in FIG. 11. Second expansion cells 154 will be recognized as mirror images of the first expansion cells 152. The second expansion cells are also disposed side-by-side in circumferential bands. Circumferential bands of first and second expansion cells may desirably alternate along at least a portion and more desirably, the entire length of the stent. As shown in FIGS. 1–4, the first and second cells are staggered about the periphery of the stent relative to one another.

Figure 12:
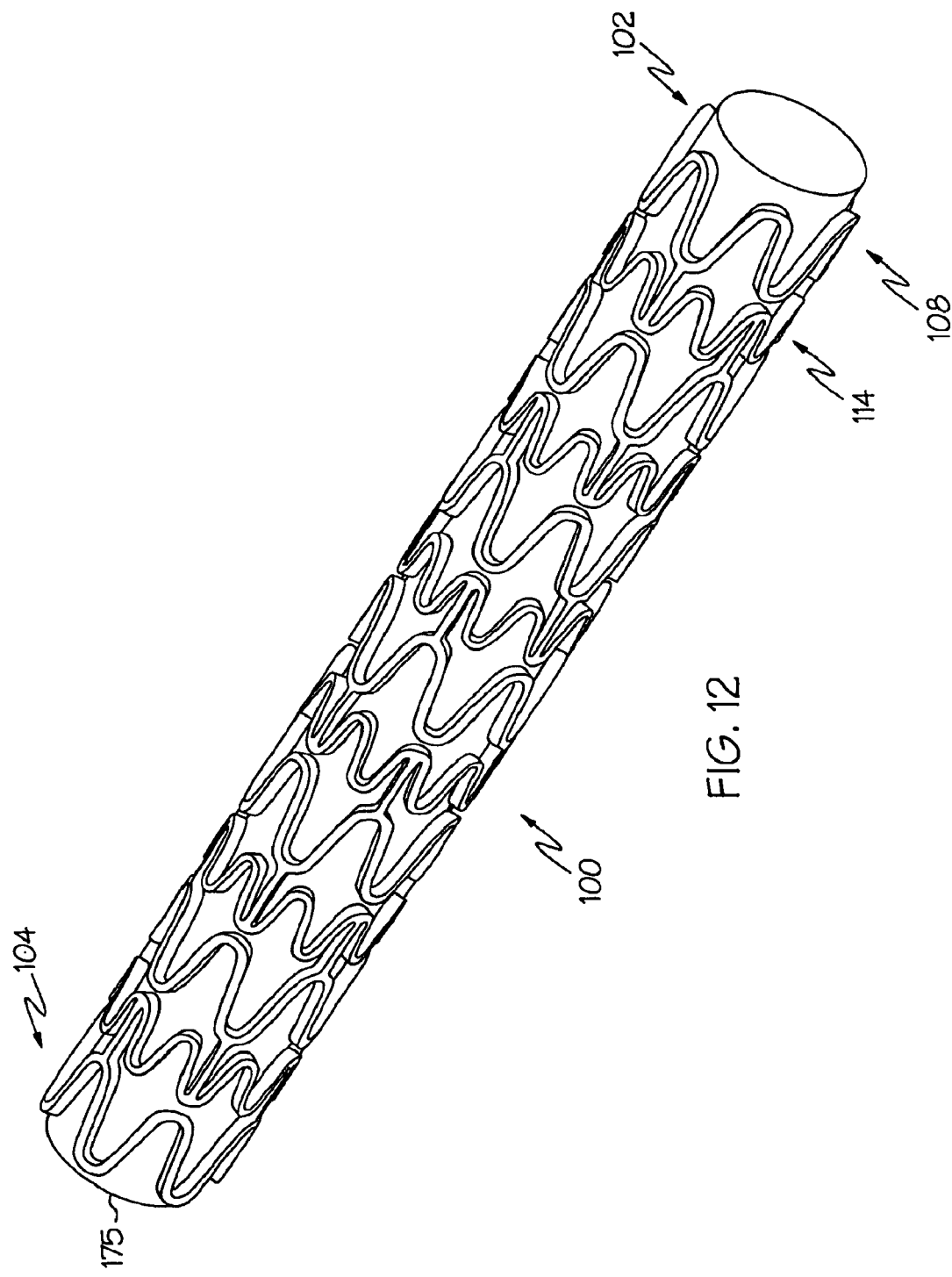
FIGS. 12–13 show an unexpanded and an expanded stent, respectively, disposed about a support.
Figure 13:
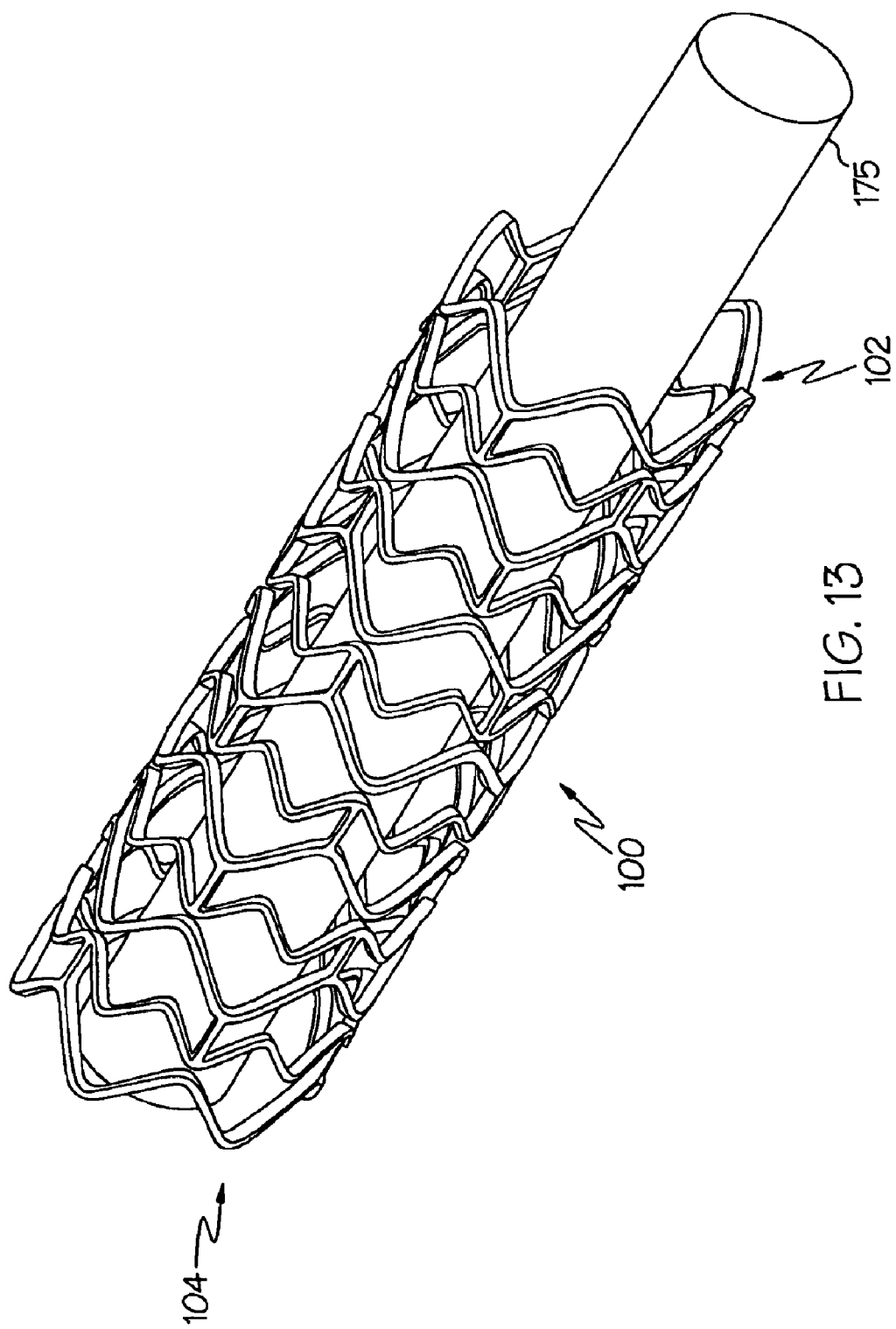
Figure 14:
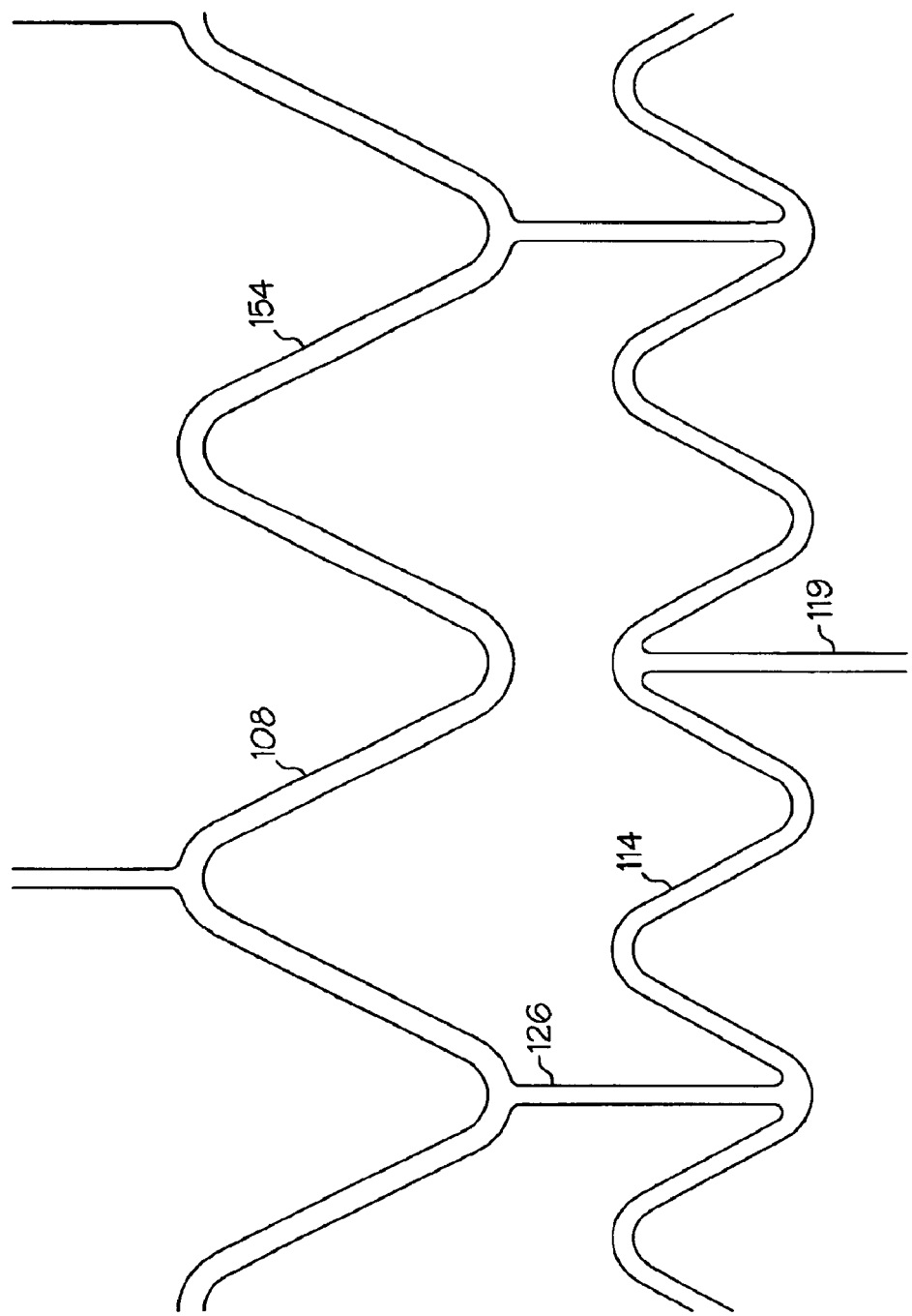
FIG. 14 shows a flat pattern of a cell of an expanded inventive stent.

The invention is directed to stents such as those described above in an unexpanded state as well as in an expanded state. An inventive stent in an unexpanded state is shown at 100 in FIG. 12. Stent 100 is disposed about support 175. The stent of FIG. 12 is shown in an expanded state in FIG. 13. A portion of an inventive stent in an expanded state including expanded second cell 154 is shown in FIG. 14.

The rigidity of the inventive stents in the expanded state may be controlled by suitably arranging the connecting members. For example, where a stent with rigid ends and a more flexible middle portion is desired, more connecting members may be provided at the ends. Similarly, a stent with more flexible ends may be achieved by providing fewer connectors at the ends. A stent with increasing rigidity along its length may be provided by increasing the number of connectors along the length of the stent or by providing increasingly rigid undulating bands.

Any suitable undulating bands may be used in the inventive stents. The undulating bands 108 of FIGS. 1–4 are of a single wavelength and amplitude. Undulating bands having multiple amplitudes and/or wavelengths may also be used in the inventive stents.

The inventive stent of FIG. 5 includes bands 114 which are characterized by multiple amplitudes. Undulating bands 114 may be characterized as having regions of smaller amplitude 114' and regions of larger amplitude 114". The stent of FIG. 5 includes undulating bands 114 whose peaks are all longitudinally aligned with one another and for which every other trough is in longitudinal alignment. As shown in FIG. 5, the troughs in regions of larger amplitude are aligned with troughs in adjacent undulating bands. The invention also contemplates the possibility of having undulating bands with regions of larger amplitude and regions of smaller amplitude where the troughs are all longitudinally aligned but the peaks are not all in longitudinal alignment.

FIG. 6 illustrates another inventive stent with undulating bands 114 of multiple amplitudes. In the embodiment of FIG. 6, every other trough of undulating band 114 is in longitudinal alignment and every other peak of undulating band 114 is in longitudinal alignment. Adjacent troughs in undulating bands 114 are longitudinally displaced from one another and adjacent peaks in undulating bands 114 are displaced from one another.

Figure 15:
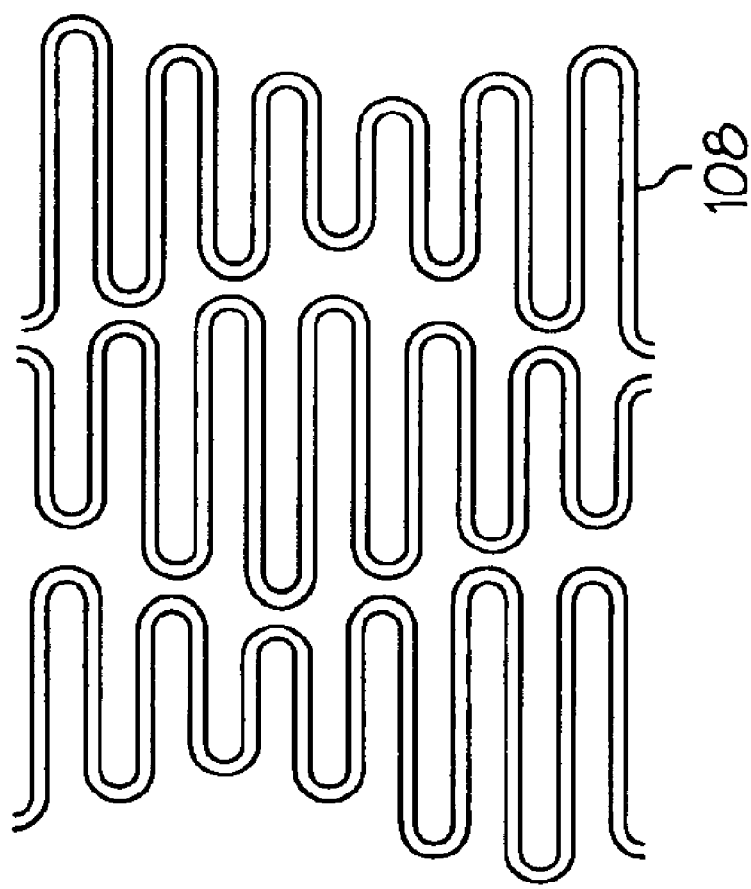

FIG. 15 illustrates another band 108 having multiple amplitudes that may be used in the inventive stents. The band shown in FIG. 108 has an increasing and then decreasing amplitude.

Undulating bands characterized by a plurality of frequencies may also be used in the inventive stents. Bands 114 shown in FIG. 6 are characterized by a wavelength of the individual peaks and by a wavelength of the repeat pattern of two peaks. Band 108 in FIG. 15 is similarly characterized by a plurality of different wavelengths.

Other examples of band patterns that may be used in any of the inventive stents disclosed herein are shown in FIGS. 16–20. Undulating band 108 of FIG. 16 is characterized by the presence of peaks 110 having varying radii of curvature which provide a generally uniform radial expansion of the undulating band. Additional details of such a band may be found in U.S. Pat. No. 5,569,295. Undulating bands 108 which slant relative to the longitudinal axis 106, as shown in FIG. 17 may also be used in the inventive stents. FIG. 18 illustrates another example of a suitable undulating band 108 for use in the inventive stents. A portion of yet another suitable undulating band is shown in FIG. 19. Peak 110 and trough 112 of undulating band 108 are thinner than struts 107. Some or all of the peaks and/or troughs of the bands may be thinner than the struts or thicker than the struts. A portion of an undulating band having a thicker peak and thinner struts is shown at 108 in FIG. 20 as well as in FIG. 27. The width of the band tapers as the band as traversed from peak 108 toward the trough with $W_a$ exceeding $W_b$. Desirably, portions of undulating bands adjacent peaks and/or troughs from which connectors extend taper. Also desirably, the ratio of the maximum width along an undulating band to a minimum width along the undulating band will range from 1:1 to 1.5:1. Any of the undulating bands disclosed in WO0030563 may also be used in the inventive stents.

The undulating bands discussed in this disclosure are all open at the distal end and at the proximal end. It is also within the scope of the invention to use bands which are closed at the proximal and distal ends. Examples of such a band are shown at 108 in FIGS. 21 and 22. Bands 108 of FIGS. 21 and 22 have fully enclosed openings therein.

The bands may have regular patterns or may have irregular patterns.

The invention is also directed to helical stents having connected first and second undulating bands. The stent of FIG. 1 or any of the other figures disclosed herein, may be provided in helical form by modifying the undulating first and second bands to extend helically about the longitudinal axis of the stent. Any of the features discussed above or below with respect to non-helical stents may be provided in a helical stent as well.

Figure 23:
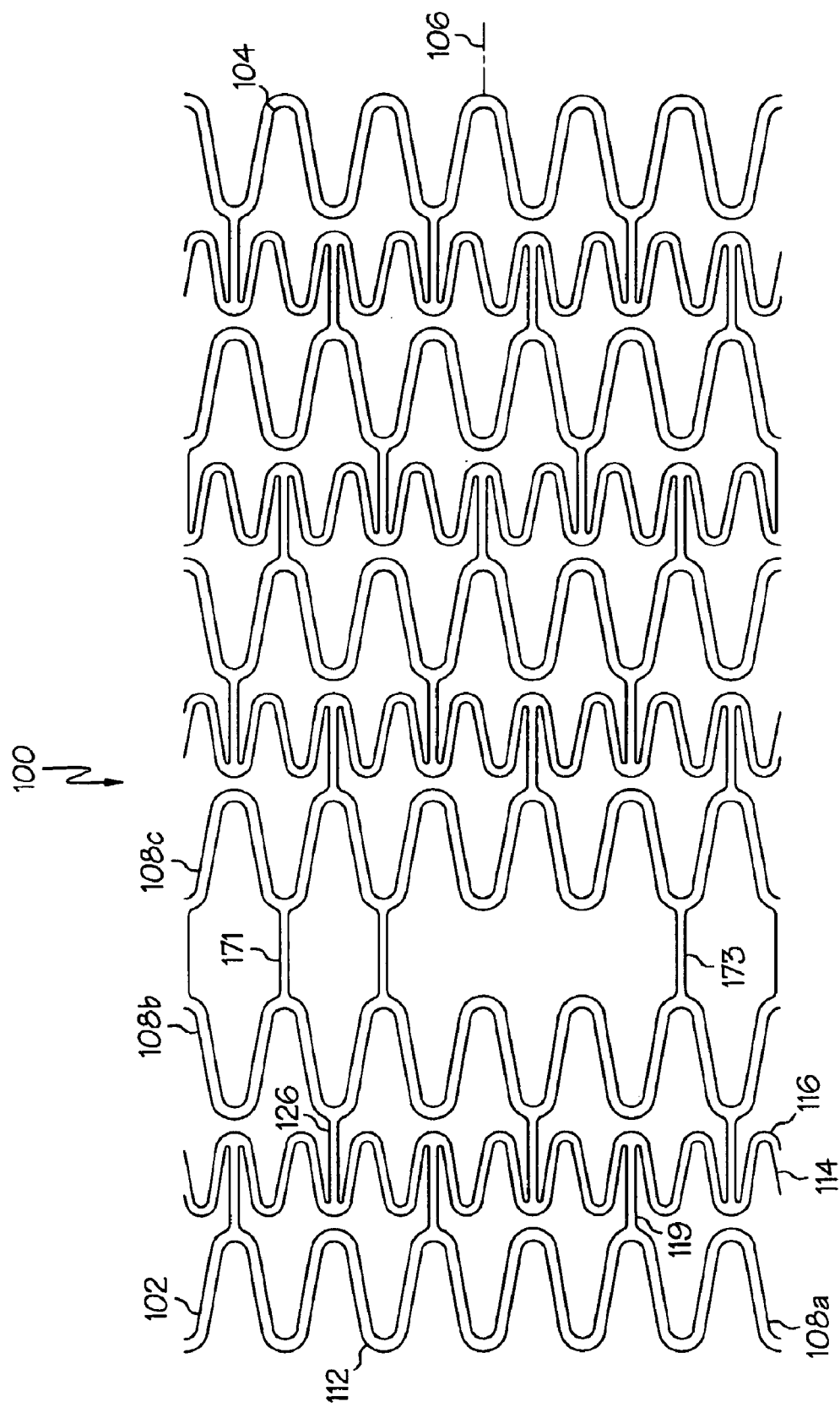
FIGS. 23–25 are flat patterns of inventive stents having side branch access.

The invention is also directed to stents with sidebranch access. Such a stent may be provided by omitting one more first and/or second undulating bands. An example of such a stent is shown generally at 100 in FIG. 23. Stent 100 is similar to that shown FIG. 4, differing in that an undulating second band has been omitted and adjacent undulating first bands are connected across the region of the omitted undulating second band via side-branch connectors 171. A plurality of peaks and facing troughs on adjacent first undulating bands on either side of the location for sidebranch access are connected via side-branch connectors 171 and at least one of peak and facing trough is not connected thereby resulting in an enlarged opening providing for sidebranch access. Sidebranch opening 173 is highlighted in FIG. 23. Increased side branch access may be achieved by providing for several adjacent unconnected peaks and troughs as shown in FIG. 23. Even greater sidebranch access may be achieved by providing an undulating band with a larger wavelength in place of first undulating band 108b and/or first undulating band 108c.

Figure 24:
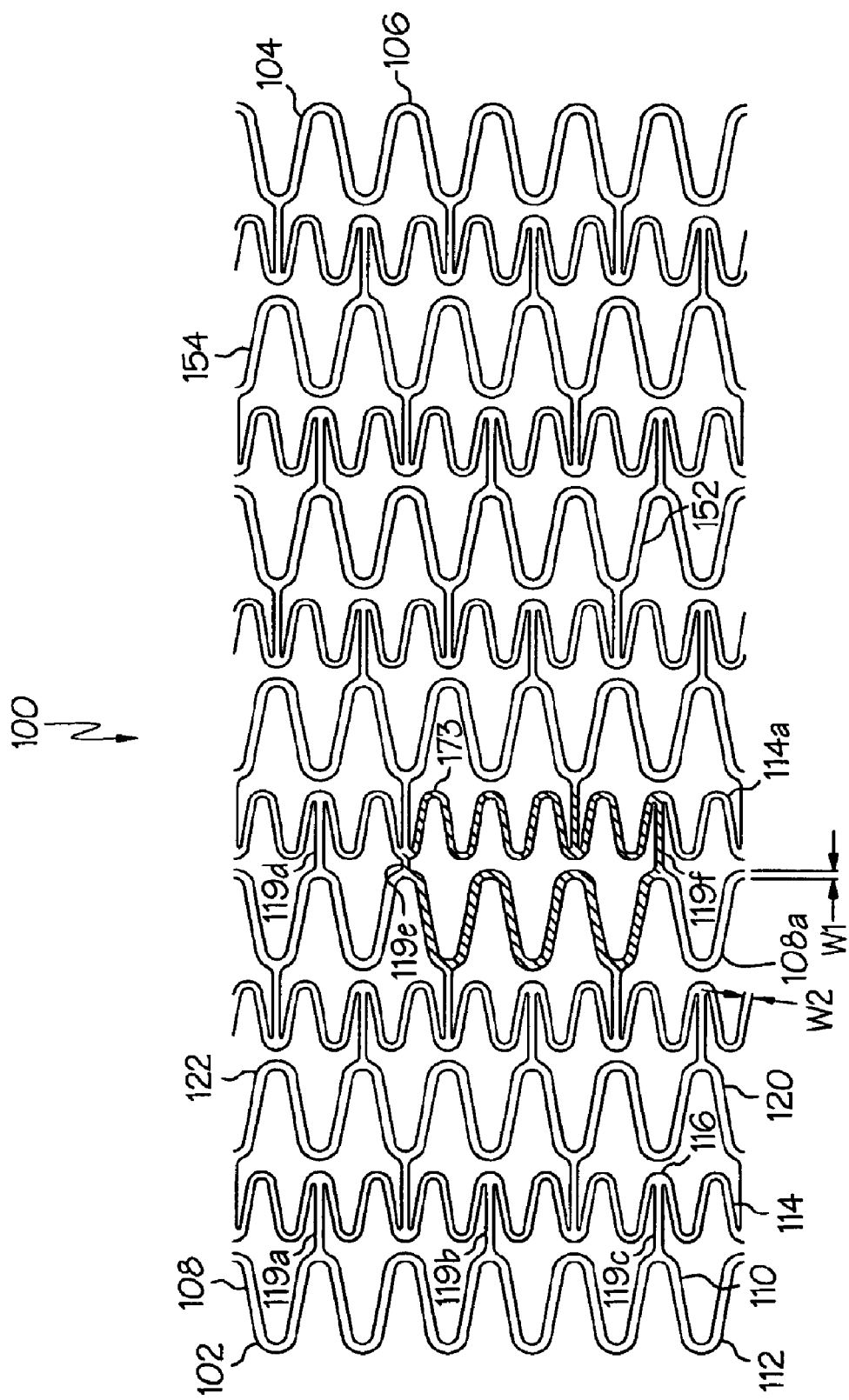

Sidebranch access may also be provided by omitting a first undulating band and providing connectors between some, but not all of the peaks and troughs of the resulting adjacent second undulating bands. Sidebranch access may further be achieved in any of the inventive stents disclosed herein by alternating the location of connectors between adjacent undulating bands. For example, an inventive stent may be provided with undulating first and second bands where there are N connectors between adjacent bands except in the region where sidebranch access is desired. In that region of the stent, M connectors, where M<N may be provided. As shown in FIG. 24, sidebranch access may also be attained by maintaining a constant number of connectors between first and second undulating bands throughout the stent while spacing some of the connectors 119d–f that join the first undulating band 108a and second undulating band 114a which define sidebranch opening 173 closer together (e.g. 119d and 119e) and some of the connectors (e.g. 119e and 119f) further apart as compared with the spacing of the connectors (e.g. 119a–c) between any other pair of adjacent first and second undulating bands. Connector 119e is a very short connector connecting togther a peak of one undulating band and a trough of an adjacent undulating band which faces the peak.

Figure 25:
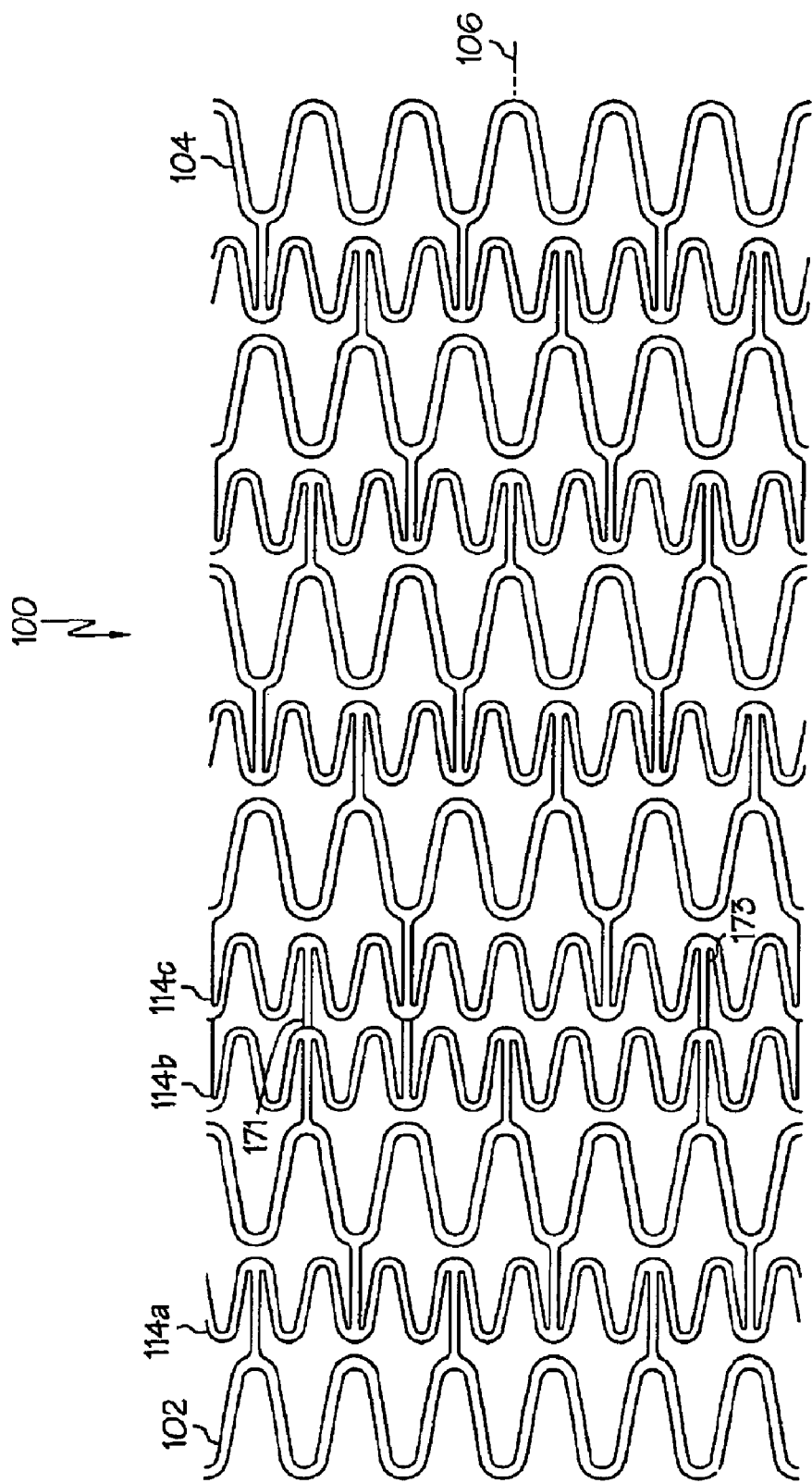

Another inventive stent which provides for sidebranch access is shown in FIG. 25. Stent 100 includes two adjacent second undulating bands which are connected in several locations. Sidebranch opening 173 is shown highlighted in FIG. 25. Adjacent second undulating bands 114b and 114c on either side of the sidebranch opening are in phase with one another and are connected peak to peak and trough to trough via connectors 171, as shown in FIG. 25. Adjacent second undulating bands 114a and 114b may also be out-of phase with one another and connected peak to peak. As shown in FIG. 25, adjacent connectors 171 are separated by four peaks to define the sidebranch opening. Adjacent connectors may be spaced closer together to define a smaller sidebranch opening or larger apart to define a larger sidebranch opening. Additional information about side branch openings may be found in the copending, commonly assigned U.S. application Ser. No. 09/659,571.

The invention is also directed to a stent having at one or more first undulating bands and one or more second undulating bands, the first and second undulating bands having different wavelengths and amplitudes. The first undulating bands and second undulating bands may be distributed in any order so long as at least one first undulating band is connected to a second undulating band. Desirably, at least one first undulating band will be connected peak to peak or trough to trough with an adjacent second undulating band. In one embodiment of the invention, the stent comprises a grouping of M first undulating bands adjacent one another where M≧1 and a grouping of N second undulating bands adjacent one another where the grouping of M first undulating bands is adjacent to and connected to the grouping of N second undulating bands of and adjacent and where N≧1. Adjacent bands are connected peak to peak and/or trough to trough. For example, an inventive stent may comprise three coupled first undulating segments connected peak to peak and/or trough to trough and two coupled second undulating bands connected peak to peak and/or trough to trough. The adjacent first and second undulating bands are also connected peak to peak and/or trough to trough.

The invention is also directed to a stent such as that shown generally in the flat at 400 in FIG. 26*a*. Stent 400 comprises a plurality of undulating bands including a first undulating band 408*a* of a first amplitude and wavelength and a second undulating band 408*b* of a second amplitude and wavelength. Each undulating band comprises alternating peaks 410 and troughs 412. As shown in FIG. 26*a*, the first wavelength exceeds the second wavelength and the first amplitude is greater than the second amplitude. More generally, the first wavelength may be larger than the second wavelength and/or the first amplitude may be greater than the second amplitude. First undulating band 408*a* is connected to second undulating band 408*b* via first longitudinal connectors 419 which extend from troughs 412 on first undulating band 408*a* to troughs 412 on second undulating bands 408*b*.

The stent desirably further comprises a third undulating band 408*c* having alternating peaks 410 and troughs 412. Desirably, the third undulating band is of the same wavelength and amplitude as the first undulating band. Second undulating band 408*b* and third undulating band 408*c* are connected via second connectors 426 which extend from peaks 410 of second undulating bands 408*b* to peaks 410 of third undulating bands 408*c*.

The stent pattern of undulating bands 408*a–c* and connectors 419 and 427 may be repeated throughout the stent, as shown in FIG. 26*a* or may be present in only a portion of the stent.

The invention is also directed to a stent, such as that shown in the flat at 400 in FIG. 26*a*, comprising a first undulating band 408*a* of a first wavelength and a second undulating band 408*b* of a second wavelength less than the first wavelength. The first undulating band 408*a* has a first end 428 and a second end 430 and the second undulating band 408*b* has a first end 428 and a second end 430. At least one and desirably a plurality of substantially longitudinal connectors 419 extend between the first and second undulating bands. The one or more substantially longitudinal connectors 419 extend from first end 428 of first undulating band 408*a* to second end 430 of first undulating band 408*a* and beyond to first end 428 of second undulating band 408*b*.

Desirably, the stent further comprises a third undulating band 408*c* of a third wavelength and amplitude and having a first end 428 and a second end 430. First, second and third undulating bands 408*a–c* are arranged sequentially. The third wavelength is desirably equal to the first wavelength and the third amplitude is desirably equal to the first amplitude. At least one substantially longitudinal connector 426 extends from second end 430 of third undulating band 408*c* to first end 428 of third undulating band 408*c* and beyond to second end 430 of second undulating band 408*b*.

The stent shown in FIG. 26*a*, with connectors which extend from one end of a larger wavelength band to the other end of the larger wavelength band and beyond to a smaller wavelength band, will crimp to a smaller diameter than a stent where the connectors extend from one end of a smaller wavelength band to the other end of the smaller wavelength band and beyond to a larger wavelength band. Moreover, for a fixed separation between undulating bands, the connectors between adjacent bands of such a stent are longer than the connectors of a stent where the connectors extend the length of the smaller wavelength bands and beyond. The longer length of the connectors also provides for increased flexibility of the stent.

Additional stents having connectors which extend the length of the larger amplitude undulating bands and beyond are shown in FIGS. 26*b–e*.

Figure 26B:
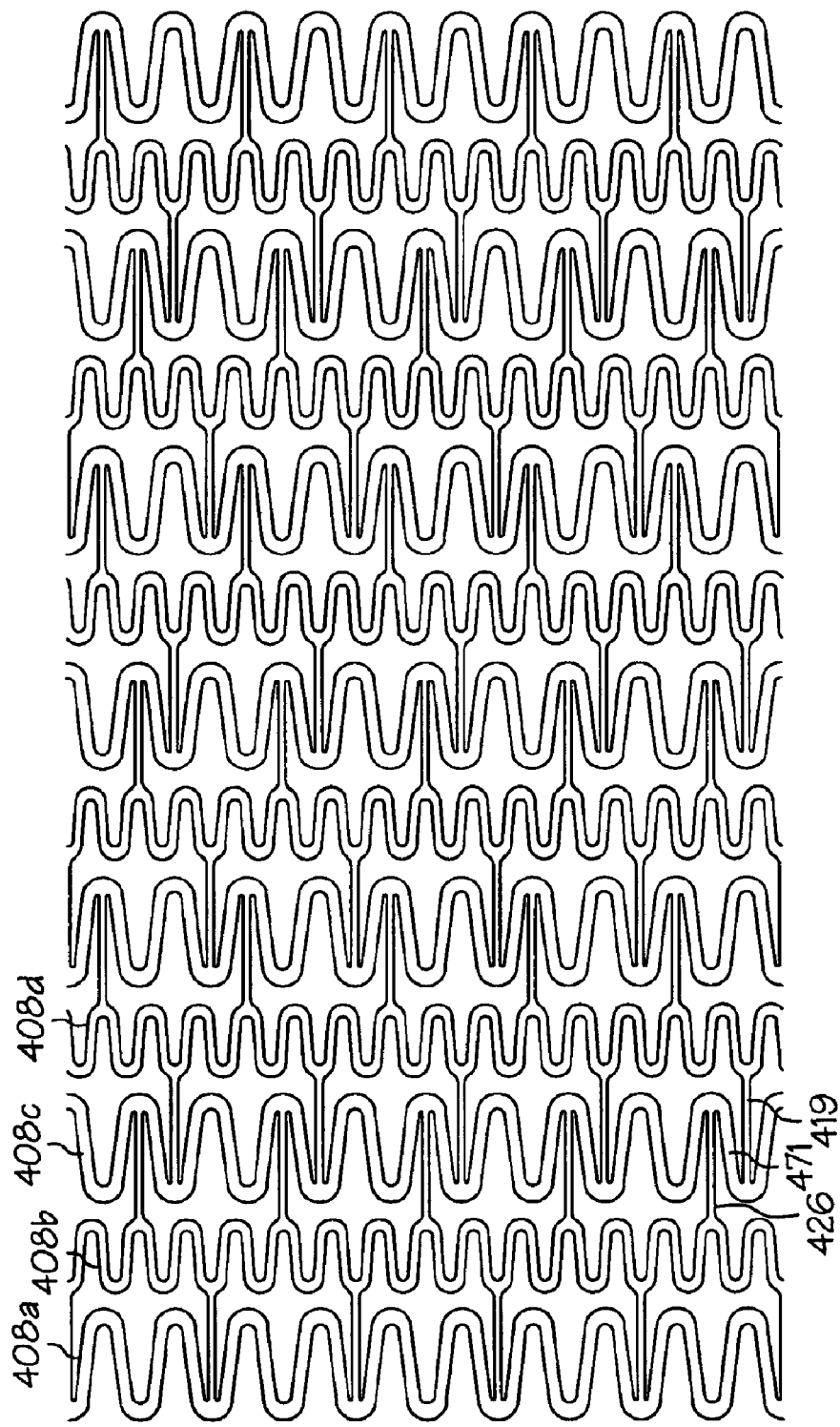

The stent of FIG. 26*b* includes second connectors 426 which extend proximally from first undulating band 408*c* to second undulating band 408*b* and first connectors 419 which extend distally from first undulating band 408*c* to second undulating band 408*d*. Nearest neighboring first and second connectors 419 and 426 are separated by one strut 471 along first undulating band 408*c*.

Figure 26C:
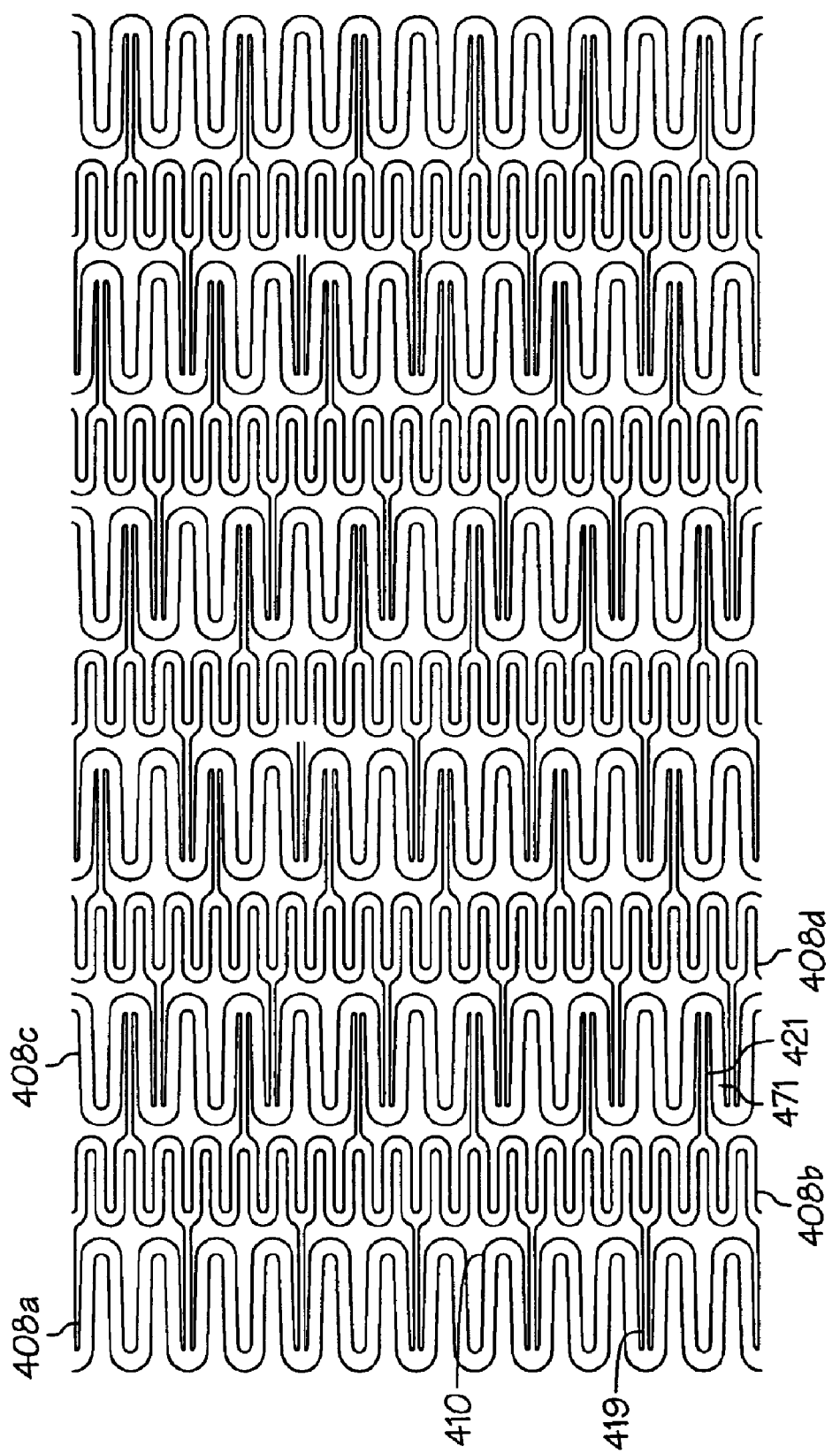

The stent of FIG. 26*c* also includes nearest neighboring first and second connectors 419 and 426 which are separated by one strut 471 along first undulating band 408*c*. Circumferentially adjacent connectors 419 are separated by two peaks 410 along the first undulating bands.

In the stent of FIG. 26*d*, nearest neighboring first and second connectors 419 and 426 are separated by three struts 471 along first undulating band 408*c*. It is also within the scope of the invention for nearest neighboring first and second connectors two be separated by more than three struts. Separations of 4, 5, 6, 7 or more struts along a first undulating band are contemplated in this embodiment as well as in any of the other embodiments of the invention disclosed herein.

Figure 26E:
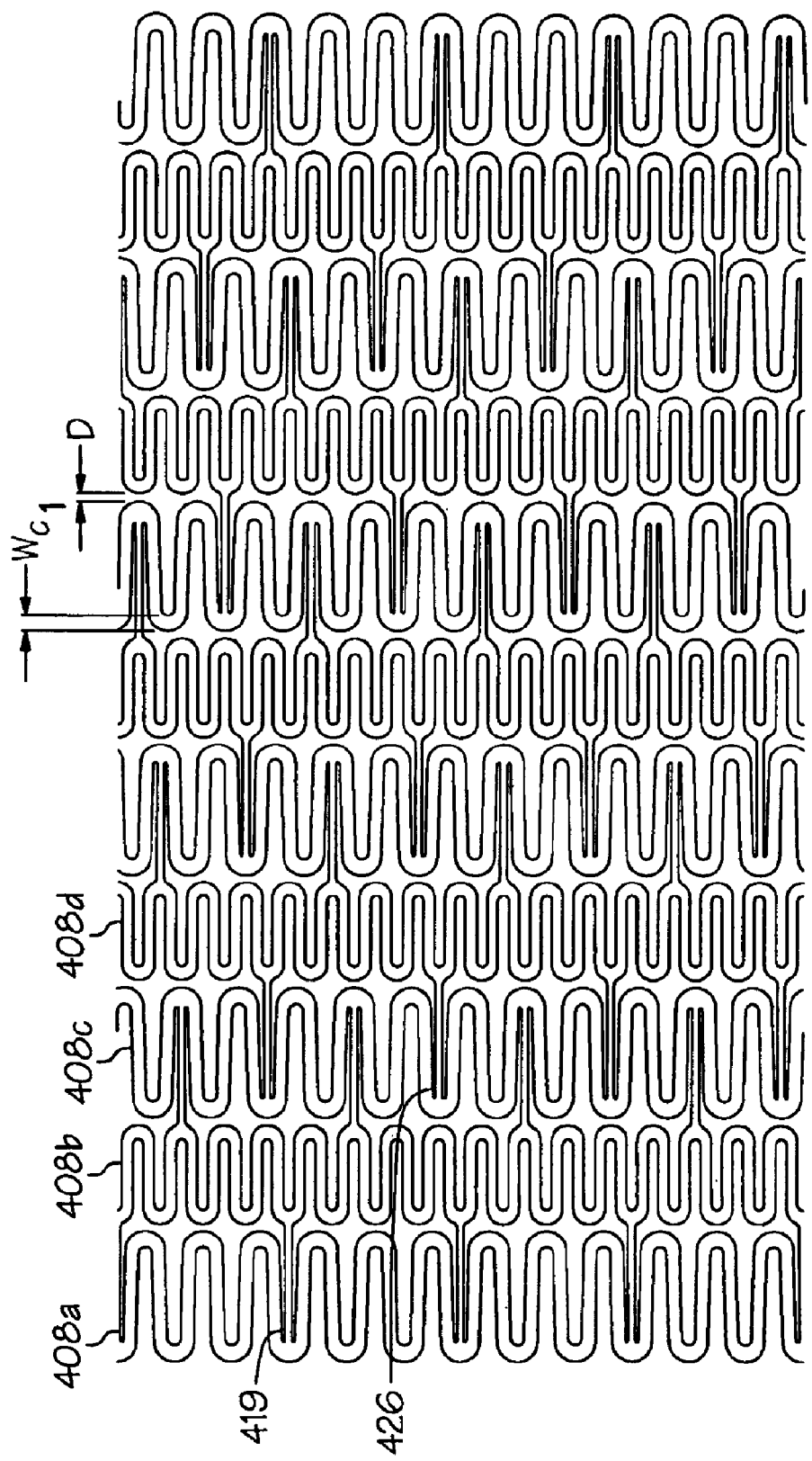

Another embodiment of the inventive stent is shown in FIG. 26*e*. Adjacent first and second undulating bands 408*a* and 408*b* are more closely spaced in the stent of FIG. 26*e* as compared with the stent of FIG. 26*d*. In the stent of FIG. 26*e*, the separation between adjacent undulating bands D is approximately 40 percent of the width $W_{e1}$ of the peaks and troughs of the first undulating band. In the stent of FIG. 26*d*, separation D is approximately equal to width $W_{e1}$.

The stents of FIGS. 26*d* and 26*e* have a ratio of first wavelength to second wavelength of 4:3 where the stent of FIGS. 26*a* and 26*b* have a ratio of first wavelength to second wavelength of 3:2. Circumferentially spaced connectors 419 in the stent of FIGS. 26*c* and 26*d* are separated by a larger number of first peaks than in the stents of FIG. 26*a* and 26*b*.

Yet another stent having large and small wavelength undulating bands and connectors which extend the length of the large wavelength bands and beyond is shown in the flat at 400 in FIG. 27. Connectors 419 of stent 400, as shown in FIG. 27 extend from first end 428 to second end 430 of first, larger wavelength undulating band 408*a* and beyond to first end 428 of second, smaller wavelength undulating band 408*b*.

The stent of FIG. 27 optionally further comprises a plurality of additional undulating bands. Third undulating band 408*c* is connected to second undulating band 408*b* via a plurality of connectors 426 extending from first end 428 of second band 408*b* to second end 430 of third undulating band 408*c*.

The pattern of undulating bands 408*a–c* and connectors 419 and 426 may be repeated throughout the stent (not shown) or other patterns of undulating bands and connectors may be provided in other sections of the stent, as shown in FIG. 27. For example, as shown in FIG. 27, stent 400 may further comprise an optional fourth undulating band 408*d* which is connector to third undulating band 408*c* via one or more third connectors 431. Third connectors 431 are desirably substantially the same length as first connectors 419. The invention also contemplates providing third connectors which are longer or shorter than first connectors 419. The stent of FIG. 27 optionally further comprises a fifth undulating band 408*e* and one or more optional fourth connectors 433 which extend between the fourth undulating band 408*d* and the fifth undulating band 408*e*. Optionally, fourth connectors 433 are shorter than the first, second and third connectors.

It is within the scope of the invention to modify any of the embodiments disclosed herein so that the longitudinal connectors extend from a first side of the larger amplitude undulating bands to the second side of the larger amplitude bands and beyond to the first side of a smaller amplitude undulating band.

Figure 28:
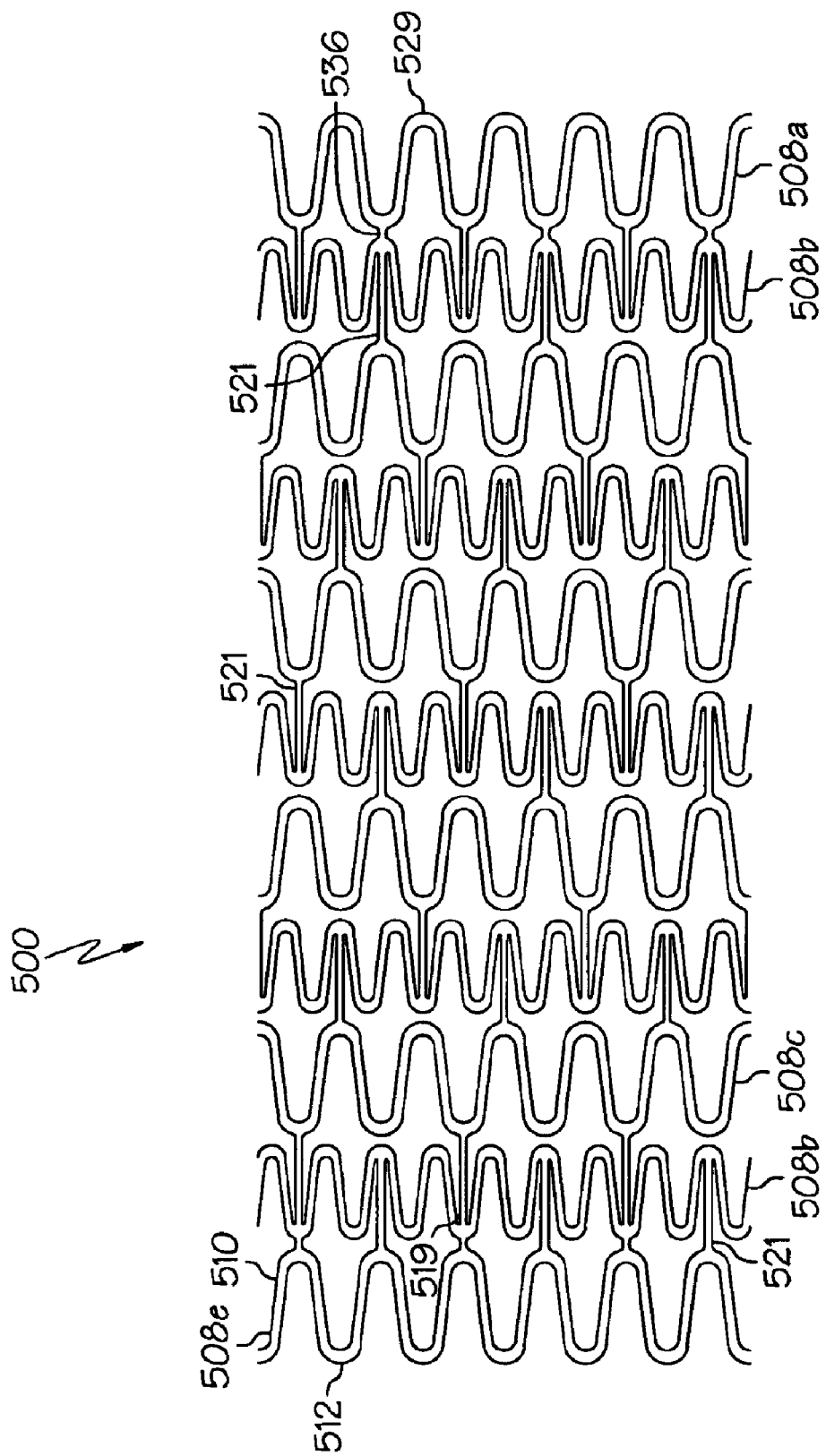

The invention is also directed to a stent such as that shown in the flat at 500 in FIG. 28. Stent 500 comprises at least three undulating bands 508 including first (508*a*), second (508*b*) and third (508*c*) undulating bands arranged sequentially along the length of stent. Each undulating band 508 has a plurality of alternating peaks 510 and troughs 512. First undulating band 508*a* and third undulating band 508*c* are 180 degrees out of phase with one another. A first set of longitudinally extending connectors 519, one of which is shown shaded in FIG. 28, extend from at least some of the peaks 510 of first undulating band 508*a* to some of the troughs 512 of third undulating band 508*c*. It is noted that connectors 519 include a very short connection 536 between adjacent undulating bands 508*a* and 508*b* and a long connector 521 extending between adjacent undulating bands 508*b* and 508*c*. The very short connection 536 adds to the stiffness of the stent while the very long connector 521 lends flexibility to the stent.

The stent may comprise additional undulating bands as shown in FIG. 28 as well as additional connectors between adjacent undulating bands. The stent of FIG. 28 includes connectors 521 which extend only between adjacent bands.

In accordance with the invention, there may be fewer connectors 519 than peaks 510 on first undulating band 508*a* so that some of the peaks are not directly connected to longitudinally adjacent troughs on the third undulating band. In one embodiment of the invention (not shown), only a single connector 519 is present.

In the embodiment of FIG. 28, the proximal and distal ends of the stent are provided with additional stiffness because of the additional, very short connections 536. The invention also contemplates embodiments in which only one of the proximal and distal ends of the stent is provided with very short connections 536 so that one end of the stent is stiffer than the other end.

The invention also contemplates embodiments in which all of the peaks of first undulating band 508*a* are connected to troughs on third undulating band 508*c* as shown in FIG. 29.

The embodiment of FIGS. 29*a,b* comprises at least three and desirably, at least five undulating bands including first (508*a*), second (508*b*), third (508*c*), fourth (508*d*) and fifth (508*e*) undulating bands arranged sequentially along the length of stent. First undulating band 508*a* and fifth undulating band 508*e* are in phase with one another. First undulating band 508*a* and third undulating band 508*c* are connected by one or more substantially longitudinal first connectors extending therebetween. Adjacent undulating bands are connected by very short connections 536 and via longitudinal connectors 529. The very short connections 536 provide the stent with stiffness and the longitudinal connectors 529 provide the stent with flexibility. Each very short connection 536 is circumferentially aligned with a longitudinal connector 529.

Desirably, as shown in FIG. 29, the stent further comprises a second set of longitudinally extending connectors 526 extending from at least some of peaks 510 of third undulating band 508(*c*) to some of troughs 512 of fifth undulating band 508(*e*). First connectors 519 are circumferentially offset from second connectors 526. Desirably, first connectors 519 intersect second undulating band 508*b* at troughs 512 along second band 508*b* and second connectors 526 intersect fourth undulating band 508*d* at troughs 512 along fourth band 508*d*. Other arrangements of the second and fourth undulating bands relative to the first, third and fifth undulating bands are also within the scope of the invention. For example, the first connectors may intersect the second undulating bands at peaks along the second band or between peaks and troughs along the second band. Similarly, the second connectors may intersect the fourth undulating bands at peaks along the fourth band or between peaks and troughs along the fourth band.

In the embodiment of FIGS. 28 and 29, the first, third and fifth undulating bands 508*a,c,e* are of a first wavelength and amplitude and the second and fourth undulating bands 508*b,d* are of a second wavelength and amplitude less than the first wavelength and amplitude. The invention also contemplates embodiments in which the first wavelength and amplitude are less than the second amplitude and wavelength as well as embodiments in which the first and second wavelengths and amplitudes are the same.

The stent may optionally comprise additional undulating bands and longitudinal connectors, as shown in FIGS. 28 and 29.

The invention is also directed to stents such as those shown in FIGS. 30–34 comprising a first undulating band 508*a* having alternating peaks 510 and troughs 512 and a second undulating band 508*b* having alternating peaks 510 and troughs 512. Desirably, the first undulating band is of a larger wavelength and amplitude than the second undulating band. Optionally, however, the first and second undulating bands may be of the same wavelength and/or amplitude. One or more first substantially longitudinal connector 529 of uniform strength extend between first undulating band 508*a* and second undulating band 508*b*. One or more very short connectors 536 of uniform strength extend between the first undulating band 508*a* and the second undulating band 508*b*. The first connector 529 is substantially longer than the very short connectors 536. The length of first connector 529 may be at least equal to the amplitude of the second undulating band 508*b* and the length of very short second connector 536 is desirably no more than twice the width of the second undulating band 508*b* and most desirably, approximately equal to the width of the second undulating band. Any of the other embodiments disclosed herein may also be provided with first longitudinal connectors and very short connectors extending between adjacent first and second undulating bands where the first longitudinal connectors are substantially longer than the second very short connectors.

Figure 30A:
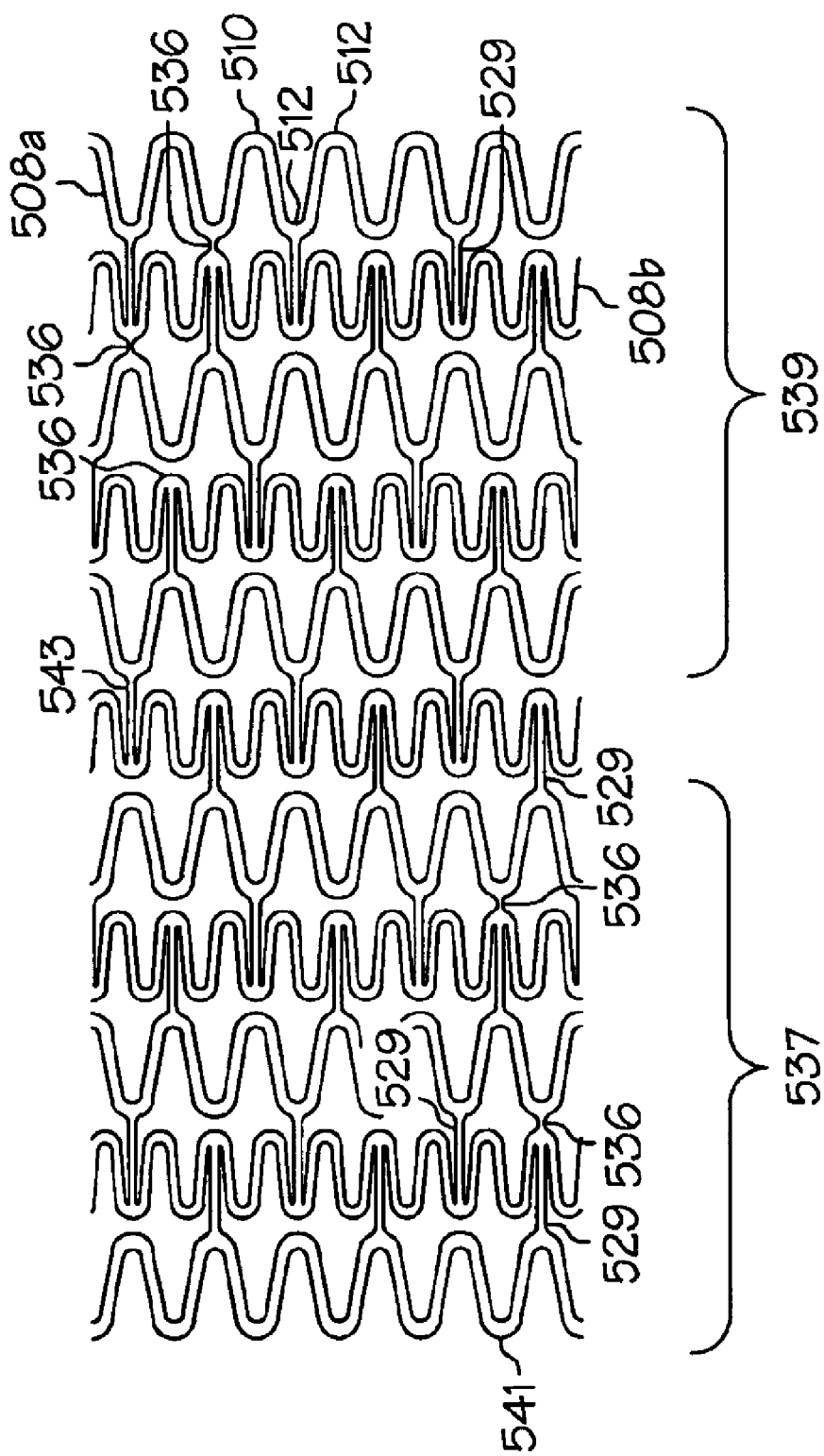

In the embodiment of FIG. 30*a*, very short second connectors 536 and first connectors 529 are arranged relative to one another to form a reinforcement member 541 (shown hatched) in first half 537 of stent 500 and to form a reinforcement member 543 (shown hatched) in second half 539 of stent 500.

Figure 30B:
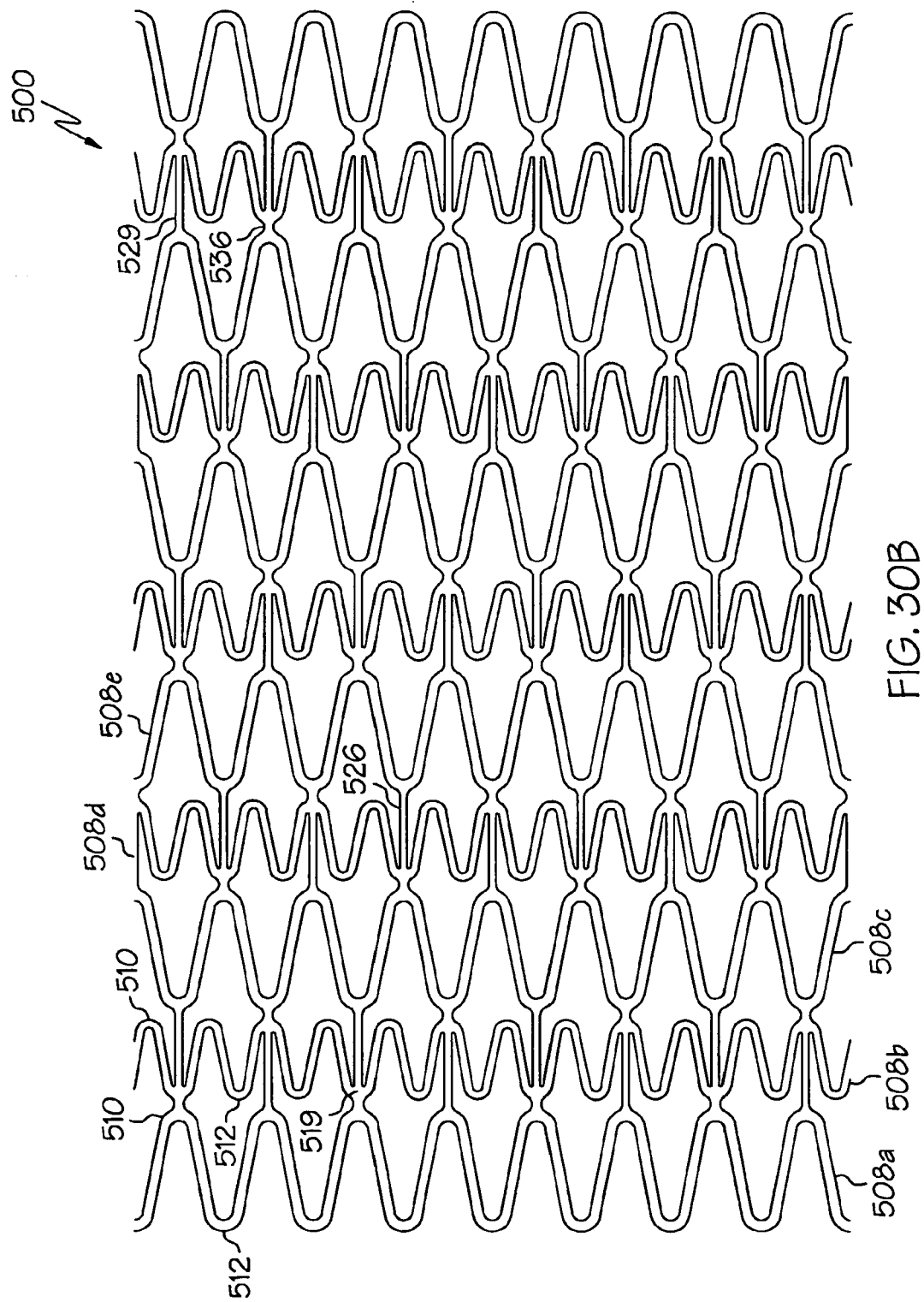
Figure 30C:
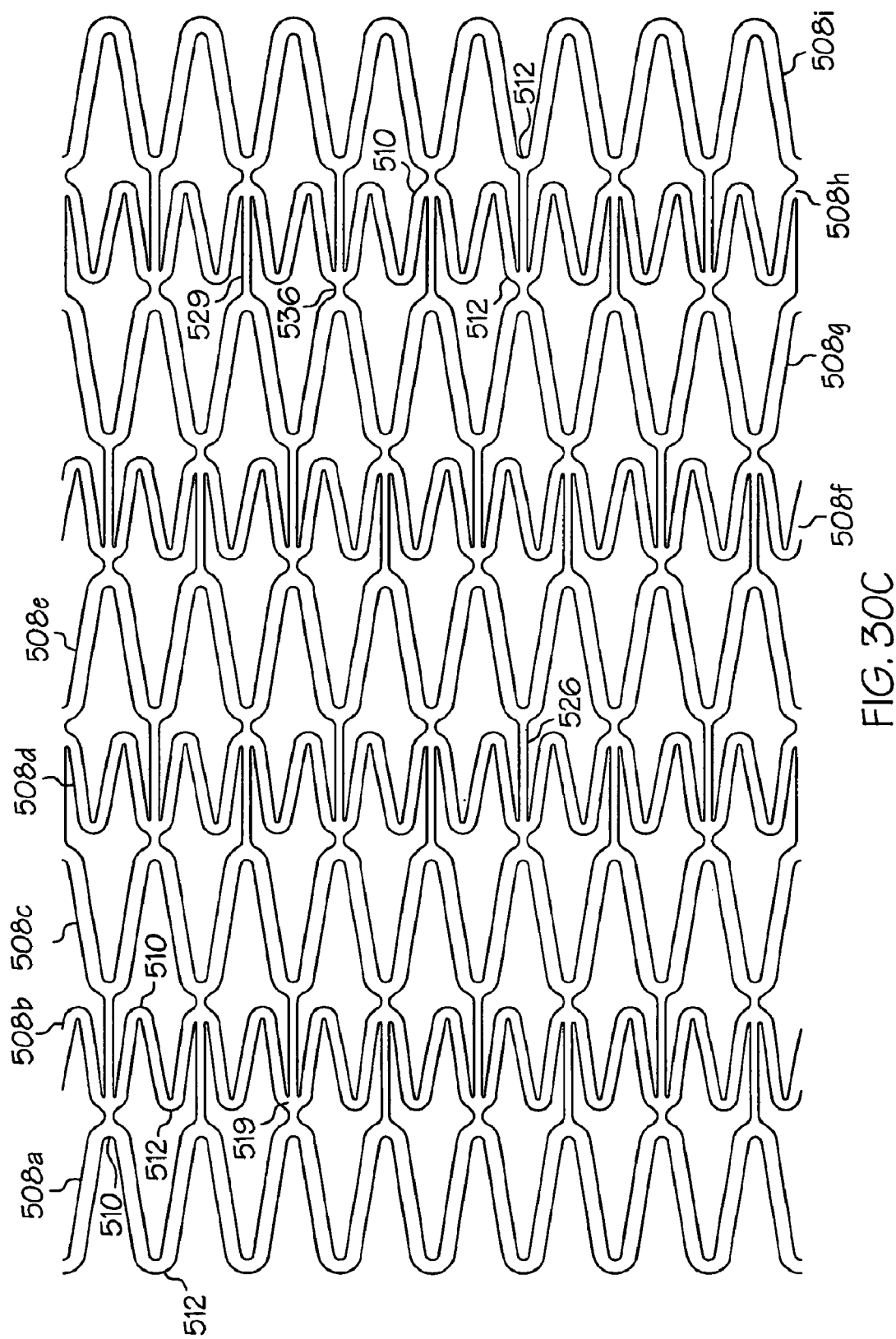

In the embodiments of FIGS. 30b and 30c, every peak 510 of proximal first undulating band 508a is connected via a longitudinal connector (to a peak 510 or a trough 512 on second undulating band 508. Every second peak 510 on first undulating band 508a is connected via longitudinal connector 519 to third undulating band 508c. Every trough 512 on distal-most first undulating band 508i is connected to a peak 510 or a trough 512 on second undulating band 508h. Longitudinal connectors 519 include a very short connection 536 between two adjacent undulating bands and a long, longitudinal connection 526 between adjacent undulating bands. Very short connection 536 adds stiffness to the stent while connections 526 add flexibility to the stent.

Figure 31:
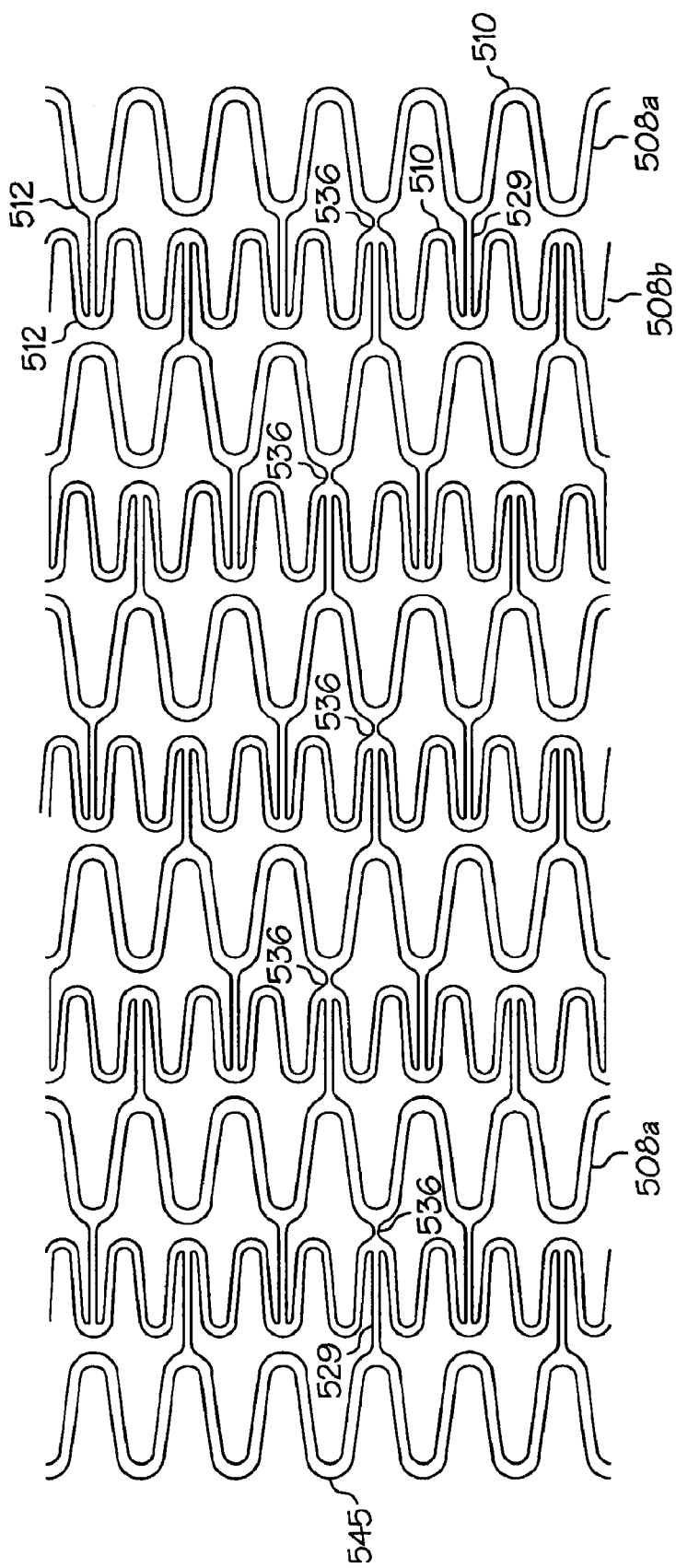

In the embodiment of FIG. 31, very short second connectors 536 and first connectors 529 are arranged relative to one another to form a reinforcement member 545 (shown hatched) which extends from the proximal end of the stent to the distal end of the stent.

Figure 32:
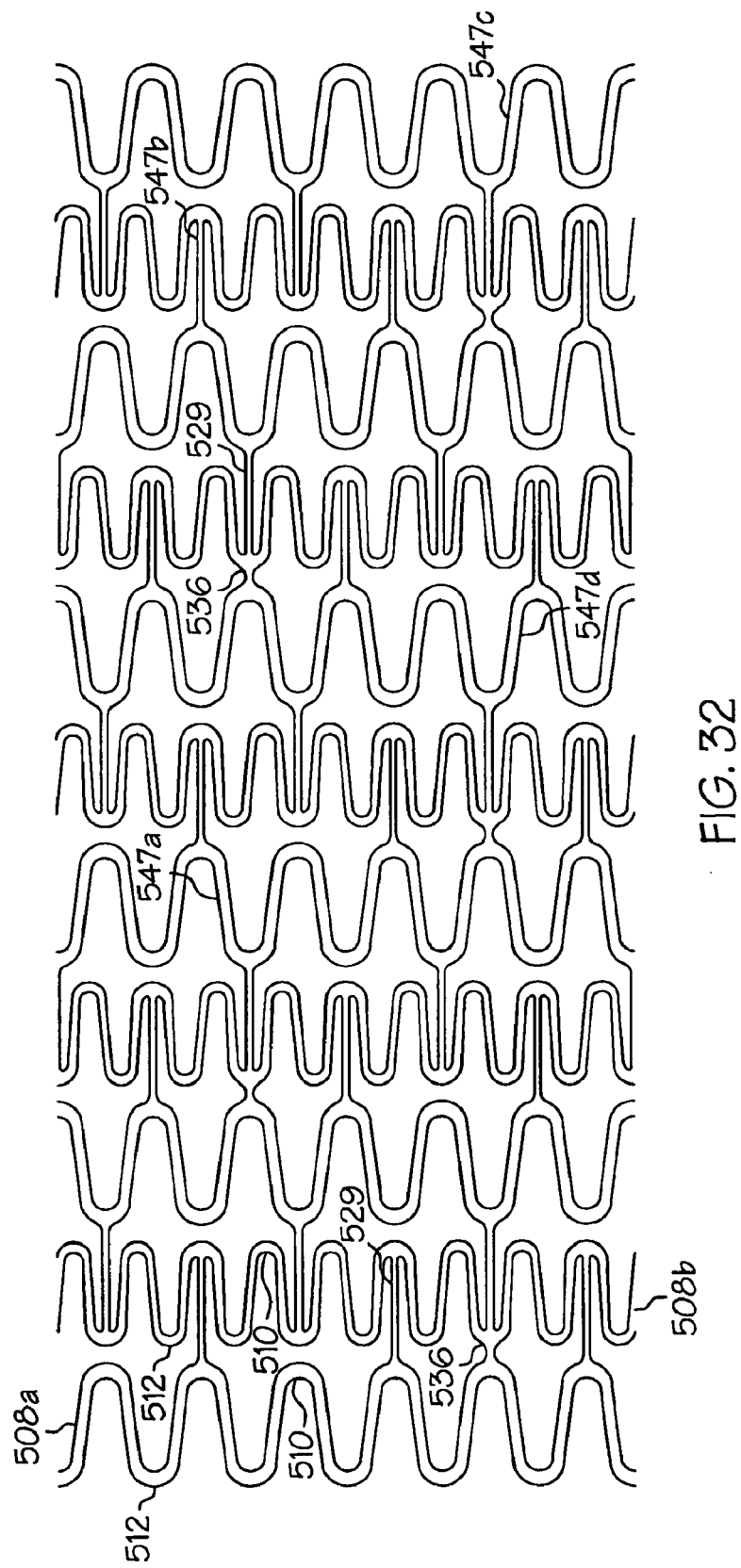

In the embodiment of FIG. 32, very short second connectors 536 and first connectors 529 are arranged relative to one another to form reinforcing members 547a–d (shown hatched). Reinforcing members 547a and 547b spiral in a first direction about a portion of the stent and reinforcing members 547c and 547d spiral in a second, opposite direction about a portion of the stent.

Figure 33:
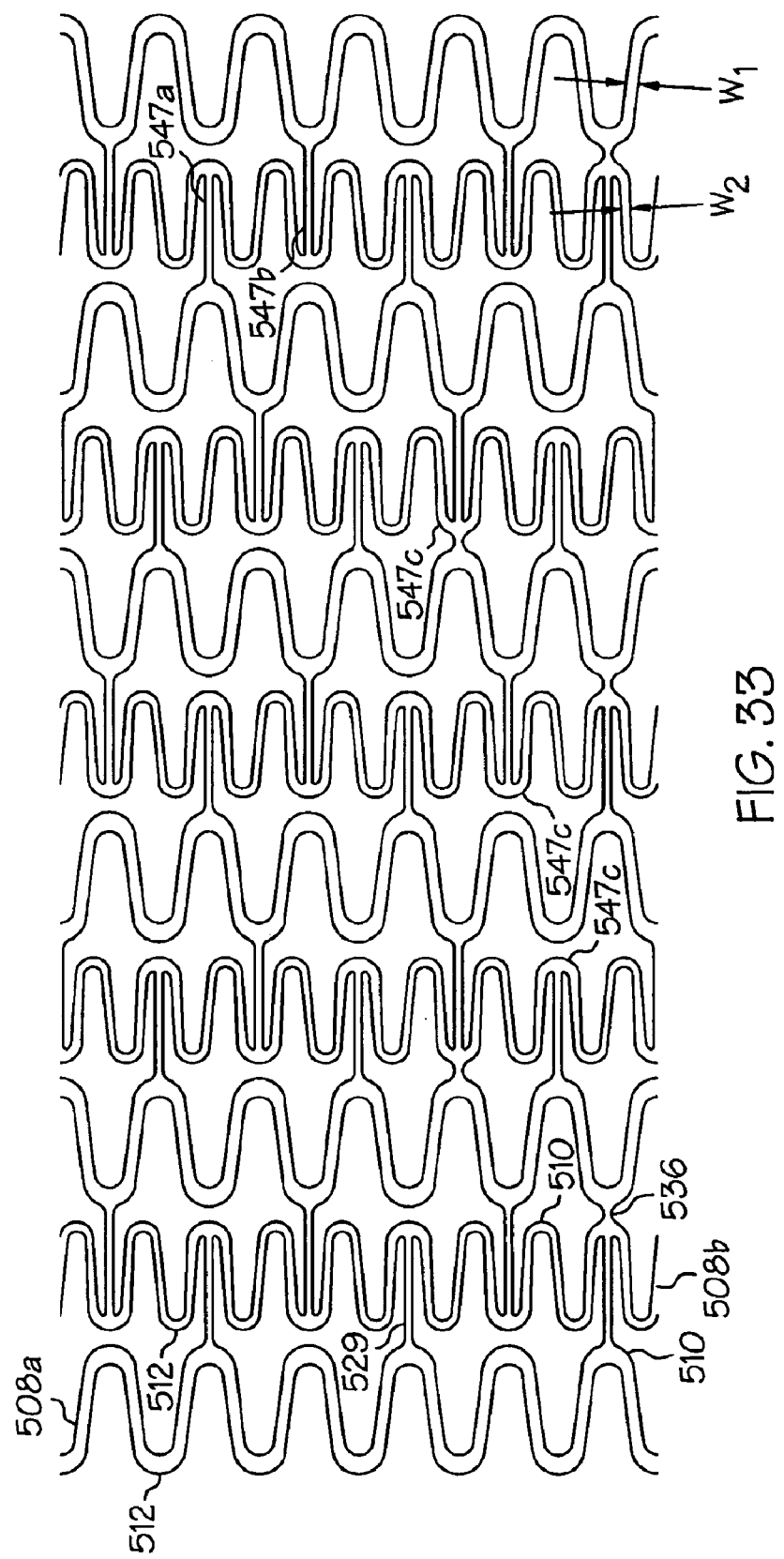

In the embodiment of FIG. 33, very short second connectors 536 and first connectors 529 are arranged relative to one another to form reinforcing members 547a–c (shown hatched). Reinforcing members 547a–c spiral in a first direction about a portion of the stent and are parallel to one another.

Figure 34:
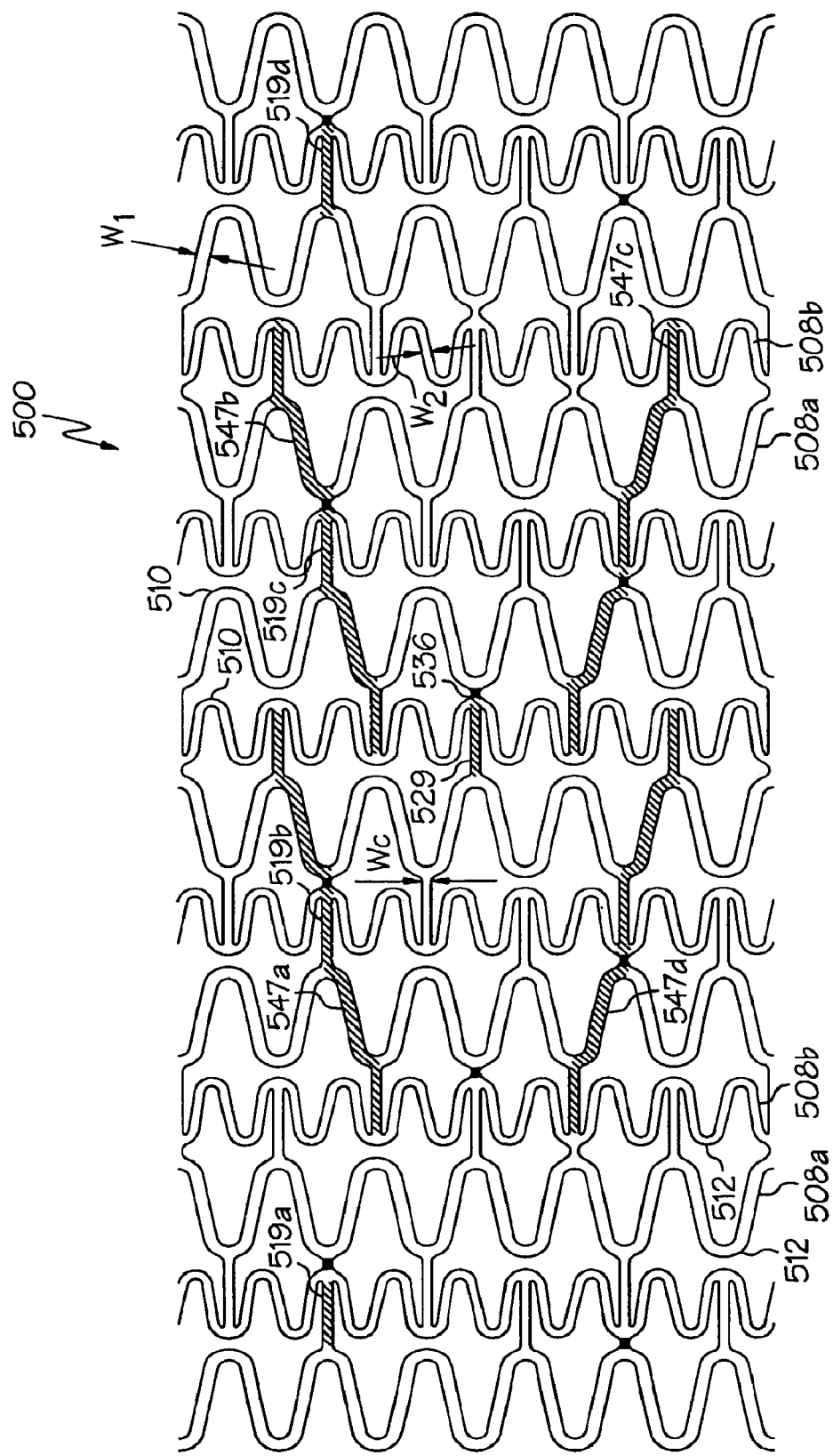

In the embodiment of FIG. 34, very short second connectors 536 and first connectors 529 are arranged relative to one another to form a plurality of reinforcing members including reinforcing members 547a–d (shown hatched). Reinforcing members 547a and 547b spiral in a first direction about a portion of the stent and reinforcing members 547c and 547d spiral in a second, opposite direction about a portion of the stent.

Figure 53:
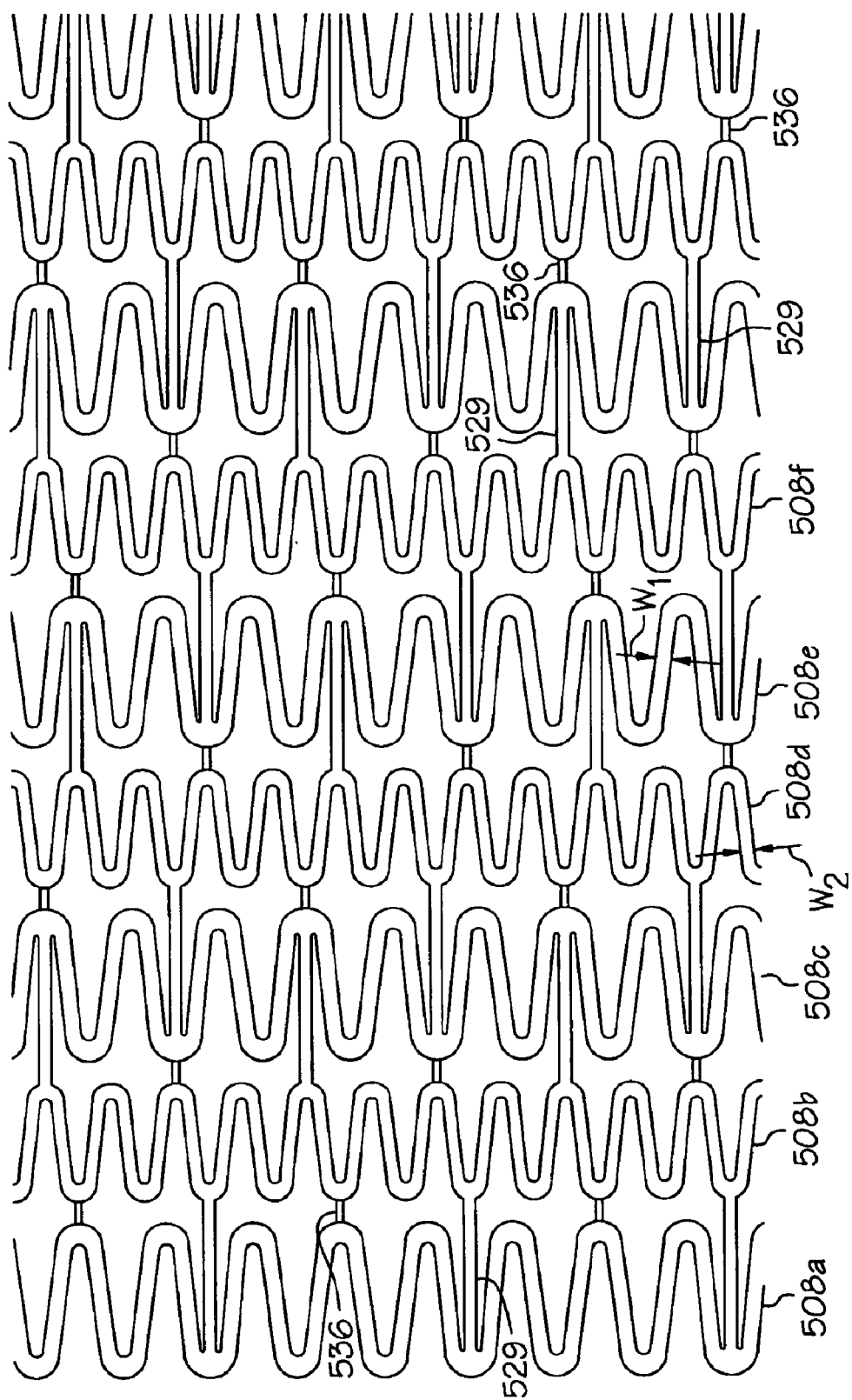

In the embodiment of FIG. 53, longitudinal first connectors 529 extend between troughs of first undulating bands 508a,c,e etc. and troughs of second undulating bands 508b, d,f etc. Very short connectors 536 extend between some of the peaks and troughs of adjacent undulating bands. As shown in FIG. 53, very short connectors extend between every pair of adjacent undulating bands. In other embodiments of the invention, very short connectors may extend between only some of the adjacent undulating bands. For example, in one embodiment of the invention, very short connectors extend between the proximal and/or distal most adjacent undulating bands but not between adjacent undulating bands in the middle of the stent.

As shown in FIG. 53, the first undulating bands are of larger amplitude than the second undulating bands and are of greater wavelength than the second undulating bands. The first undulating bands are also desirably of greater width $W_1$ than the second undulating bands $W_2$. In the embodiment of FIG. 53, the total length of the first and second undulating bands is desirably identical as the periphery of the stent is traversed. In other embodiments of the invention, the first and second undulating bands may be of different total lengths.

It is noted that in the embodiments of FIGS. 30–34, each of the reinforcing members includes one or more connectors 519 which extend from a first undulating band 508a to another first undulating band 508a and intersect with a second undulating band 508b. In the embodiment of FIG. 34, connectors 519 are arranged in discontinuous lines which extend along the length of the stent. Connectors 519a–d form one such discontinuous line. As discussed above, connectors 519 include a very short component which adds stiffness to the stent and a long component lending flexibility to the stent.

Desirably, in the embodiments of FIGS. 26–34, the ratio of the width $W_1$ of the first undulating band to the width $W_2$ of the second undulating band will range from about 1:1 to about 2:1. Even more desirably, the ratio of the width $W_1$ of the first band to the width of the second band $W_2$ is about 4:3. Also desirably, the ratio of the first wavelength to the second wavelength will range from about 1.25:1 to about 2.5:1. Most desirably, the relative widths of the first and second undulating bands will be chosen in combinations with the relative wavelengths and amplitudes of the first and second undulating bands so that the first and second undulating bands are of equal strength. Typically, the larger amplitude undulating bands will be characterized by larger width relative to the smaller amplitude bands. Any other embodiment of the invention may also be provided with these relative dimensions.

The invention contemplates providing a first undulating band which is thicker than the second undulating band or a first undulating band which is thinner than the second undulating band. Any of the embodiments disclosed herein may be so constructed.

The invention further contemplates providing longitudinal connectors which are thinner or thicker than the first and/or second undulating bands and/or wider or narrower than the width of the first and/or second undulating bands. Any of the stents disclosed herein may be provided with such features. The longitudinal connectors are desirably narrow enough to fit within the peaks and/or troughs of the first and/or second undulating bands. Desirably, the longitudinal connectors will have a width WC no wider than the width $W_1$ of the first undulating bands. More desirably, the ratio of $W_1$ to $W_c$ will be between about 1:1 and 5:1. Even more desirably, the ratio of $W_1$ to $W_c$ will be between about 1.1:1 and 2.5:1. Also desirably, the longitudinal connectors will have a width $W_c$ no wider than the width $W_2$ of the second undulating bands. More desirably, the ratio of $W_2$ to $W_c$ will be between about 1:1 and 5:1. Even more desirably, the ratio of $W_2$ to $W_c$ will be between about 1.1:1 and 2.5:1. By providing narrower and/or thinner connectors, the flexibility of the stent may be increased.

In yet another embodiment, as shown in FIGS. 35a–c, the invention is directed to stent 600 comprising at least one first undulating band 608a with alternating peaks 610 and troughs 612 and having a first wavelength and a first amplitude and at least one second undulating band 608b with alternating peaks 610 and troughs 612 and having a second wavelength and a second amplitude. First connectors 619 extend between first undulating band 608a and second undulating band 608b.

The stent further comprises at least one and desirably a plurality of third undulating bands 608c having alternating peaks 610 and troughs 612 and at least one and desirably a plurality of fourth undulating bands 608d having fourth peaks 610 and fourth troughs 612. Third undulating band 608c is characterized by a third wavelength and amplitude. Desirably, the third wavelength and amplitude are equal to the first wavelength and amplitude, respectively. Fourth undulating band 608d is characterized by a fourth wavelength and amplitude. Desirably, the fourth wavelength and amplitude are equal to the second wavelength and amplitude, respectively.

At least one and desirably a plurality of second connectors 626 extend between second undulating band 608b and third undulating band 608c. At least one and desirably a plurality of third connectors 632 extend between second undulating band 608c and third undulating band 608d.

First undulating band 608a has a width $W_1$ which is wider than the width $W_3$ of third undulating band 608c. Second undulating band 608b has a width $W_2$ which is wider than the width $W_4$ of fourth undulating band 608d.

By providing proximal and/or distal undulating bands which are wider and stronger than the intermediate undulating bands (e.g. the third and fourth undulating bands), the middle portion of the stent may be deployed first upon expansion with a balloon which provides a substantially uniform expansion pressure along its body portion. Any of the other stents disclosed herein may be provided with such a feature.

Desirably, the relative widths of the first and second undulating bands will be chosen in combinations with the relative wavelengths and amplitudes of the first and second undulating bands so that the first and second undulating bands are of equal strength. Also desirably, the relative widths of the third and fourth undulating bands will be chosen in combinations with the relative wavelengths and amplitudes of the third and fourth undulating bands so that the third and fourth undulating bands are of equal strength.

The invention also contemplates embodiments in which the first undulating band is narrower than the third undulating band and the second undulating band is narrower than the fourth undulating band. Such a stent will deploy proximal and/or distal end first upon expansion with a balloon which provides a substantially uniform expansion pressure along its body portion. Any of the other stents disclosed herein may be provided with such a feature.

Connectors with other orientations and shapes are also within the scope of other embodiments of the invention including connectors having first ends and second ends which are longitudinally and circumferentially offset and/or connectors having one or more bends therein.

The inventive stent as shown in FIGS. 35a–c includes one first undulating band and one second undulating band at the proximal end of the stent and one first undulating band and one second undulating band at the distal end of the stent. The invention also contemplates providing a first undulating band and a second undulating band at only one of the proximal and distal ends of the stent.

The inventive stent of FIGS. 35a–c is shown with two third undulating bands 608c and one fourth undulating band 608d. Desirably, the stent will have 2n third undulating bands and 2n–1 fourth undulating bands where 'n' is an integer which is greater than or equal to 1.

It is within the scope of the invention for the first and third undulating bands to be weaker than the second and fourth undulating bands. To that end, any of the stents disclosed herein may have such a feature.

It is also within the scope of the invention for the first and third undulating bands to be of different thicknesses and for the second and fourth undulating bands to be of different thicknesses. Desirably, the first undulating band is thicker than the third undulating band and the second undulating band is thicker than the fourth undulating band. In such an embodiment, the first and third undulating bands may be of the same width and the second and fourth undulating bands may be of the same width. To that end, any of the stents disclosed herein may have such a feature.

The invention is further directed to stents such as those shown in the flat at 700 in FIGS. 36–39.

The stent of FIG. 36 comprises at least one first undulating band 708a and one second undulating band 708b. Desirably, first undulating band 708 is of a first wavelength and first amplitude which are larger than the wavelength and amplitude of the second undulating band 708b. One or more longitudinal first connectors 729 extend between the first and second undulating bands, desirably, from peaks 710 on first undulating band 708a to peaks on second undulating band 708b.

Desirably, the stent further comprises additional alternating first undulating bands 708c, 708e etc. and second undulating bands 708d, 708f etc. One or more longitudinal second connectors 726 extend between troughs 712 on second undulating bands 708b, 708d etc. to troughs on first undulating bands 708c, 708e etc., respectively.

The first undulating bands of the stent of FIG. 36 include 12 peaks and 12 troughs and the second undulating bands include 18 peaks and 18 troughs. The invention also contemplates providing first and second undulating bands with fewer peaks and troughs and first and second undulating bands with additional peaks and troughs. The first and second undulating bands are of the same length in the embodiment of FIG. 36. In other embodiments of the invention, the first and second undulating bands may be of different lengths. The ratio of amplitude of the first and second undulating bands is approximately 3:2. Other ratios of amplitude are within the scope of the invention, as discussed elsewhere in this description. The widths $W_1$ and $W_2$ of the first and second undulating bands are provided in a ratio of approximately 3:2. Other ratios of widths are within the scope of the invention, as discussed elsewhere in this description. The embodiment of FIG. 36 includes 7 first undulating bands and 6 second undulating bands. The length of the stent may be increased or decreased by providing additional or fewer first and second undulating bands.

In the embodiment of FIG. 36, adjacent first and second undulating bands are separated by a distance D approximately equal to the width $W_{e1}$ of the peaks 710 of first undulating bands 708a, 708c, etc. Distance D is also approximately 1.5 times $W_{e2}$ of the peaks 710 of second undulating bands 708b, 708d, etc.

Figure 37:
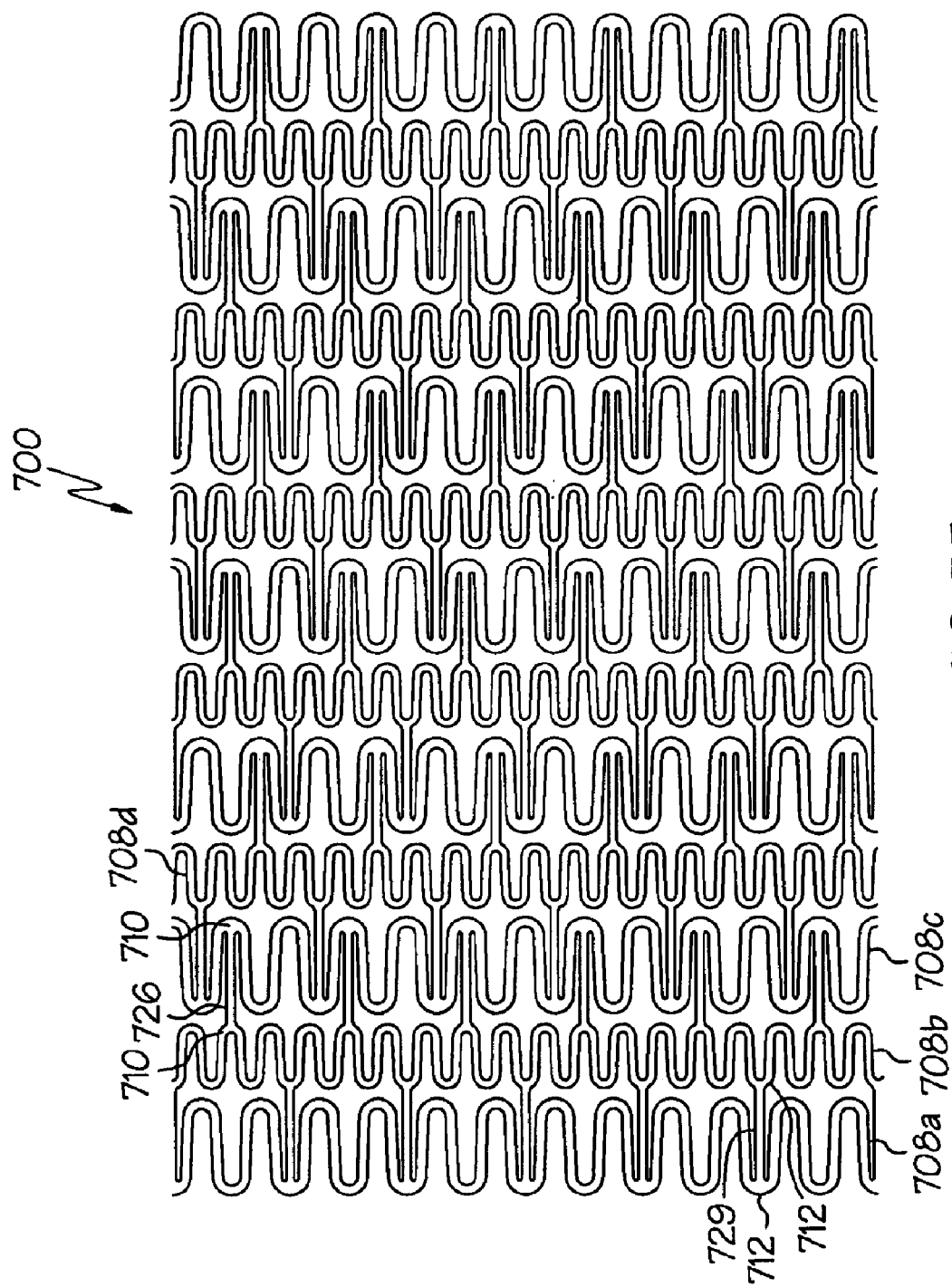

The inventive stent of FIG. 36 may also be provided in an embodiment in which long connectors are used. As shown in FIG. 37, connectors 729 extend from troughs 712 of first undulating band 708a to troughs of second undulating band 708b and connectors 726 extend from peaks 710 of second undulating band 708b to peaks of first undulating band 708c. Connectors 729 and 726 are desirably of the same length.

Figure 38:
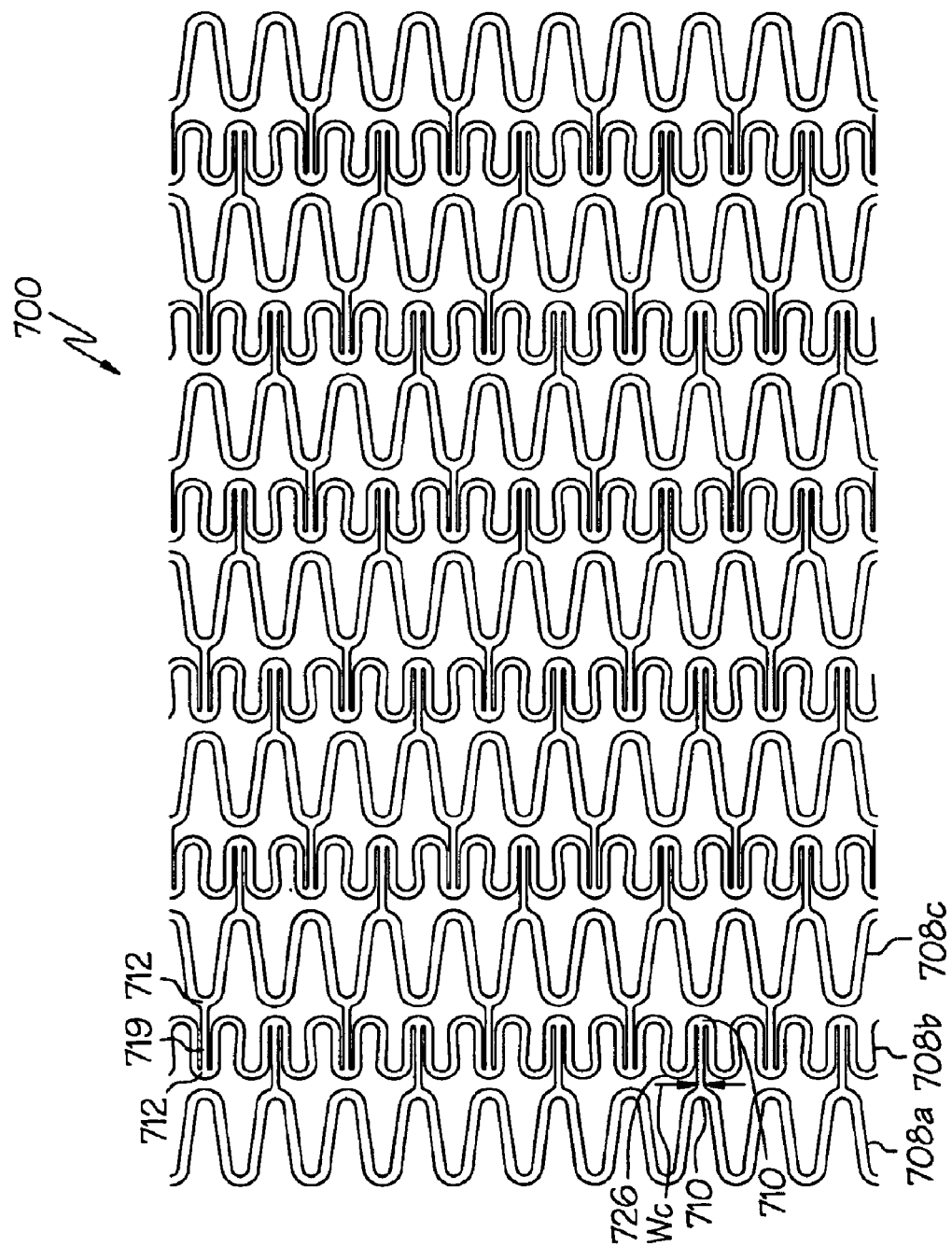

Another embodiment of the invention is shown generally at 700 in FIG. 38. The stent of FIG. 38 includes connectors 729 which extend distally from peaks 710 of first undulating band 708a to peaks of second undulating bands 708b and connectors 726 which extend distally from troughs on second undulating band 708b to troughs on first undulating band 708c. The first undulating bands include 10 peaks and 10 troughs and the second undulating bands include 15 peaks and 15 troughs and the second undulating bands. The peaks and troughs of the first and second undulating bands may be provided in other ratios as discussed in this description.

Stent 700 of FIG. 38 comprises 7 first undulating first bands and 6 undulating second bands. The length of the stent may be increased or decreased by providing additional or fewer first and second undulating bands, by altering the amplitudes of the undulating bands and/or by altering the separation of adjacent undulating bands.

Figure 39:
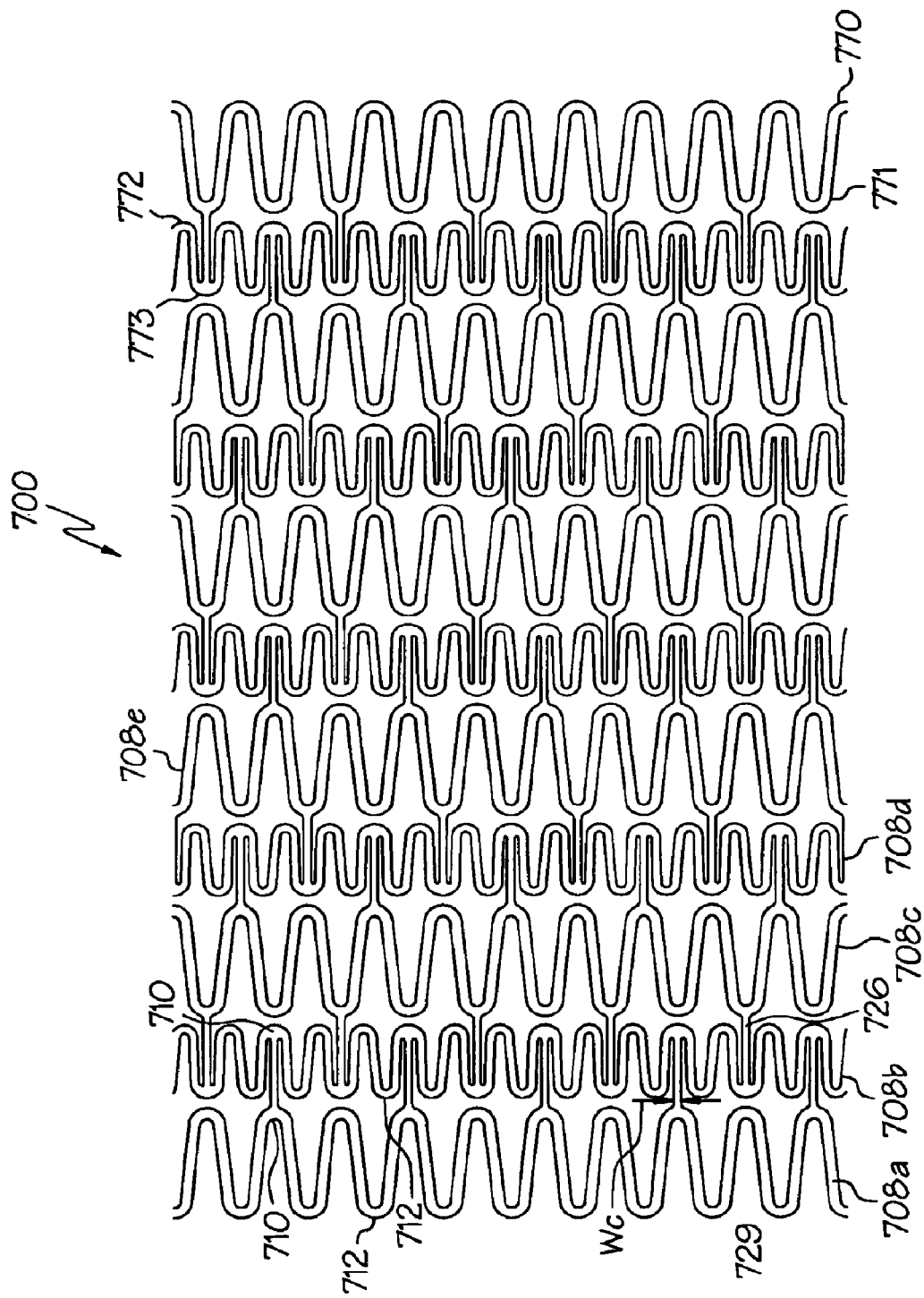

An example of a stent comprising fewer undulating bands is shown at 700 in FIG. 39. Stent 700 includes 6 first undulating bands 708*a*, 708*c*, etc. and 5 undulating second bands 708*b*, 708*d*, etc. As with the stent of FIG. 38, the stent is provided with a 3:2 ratio of peaks 710 of first undulating bands to peaks 710 of second undulating bands.

The invention is also directed to the stents shown in FIGS. 40–43 which all have at least one first undulating band 508*a* of a first wavelength and amplitude and at least one second undulating band 508*b* of a second wavelength and amplitude. Desirably, the first wavelength and amplitude exceeds the second wavelength and amplitude. At least one pair of adjacent first and second undulating bands 508*a* and 508*b* have one or more substantially longitudinal first connectors of a first length 529 extending therebetween and one or more very short second connectors 526 extending therebetween. Very short second connectors 526 extend between peaks and troughs which are circumferentially aligned and facing one another.

Figure 40:
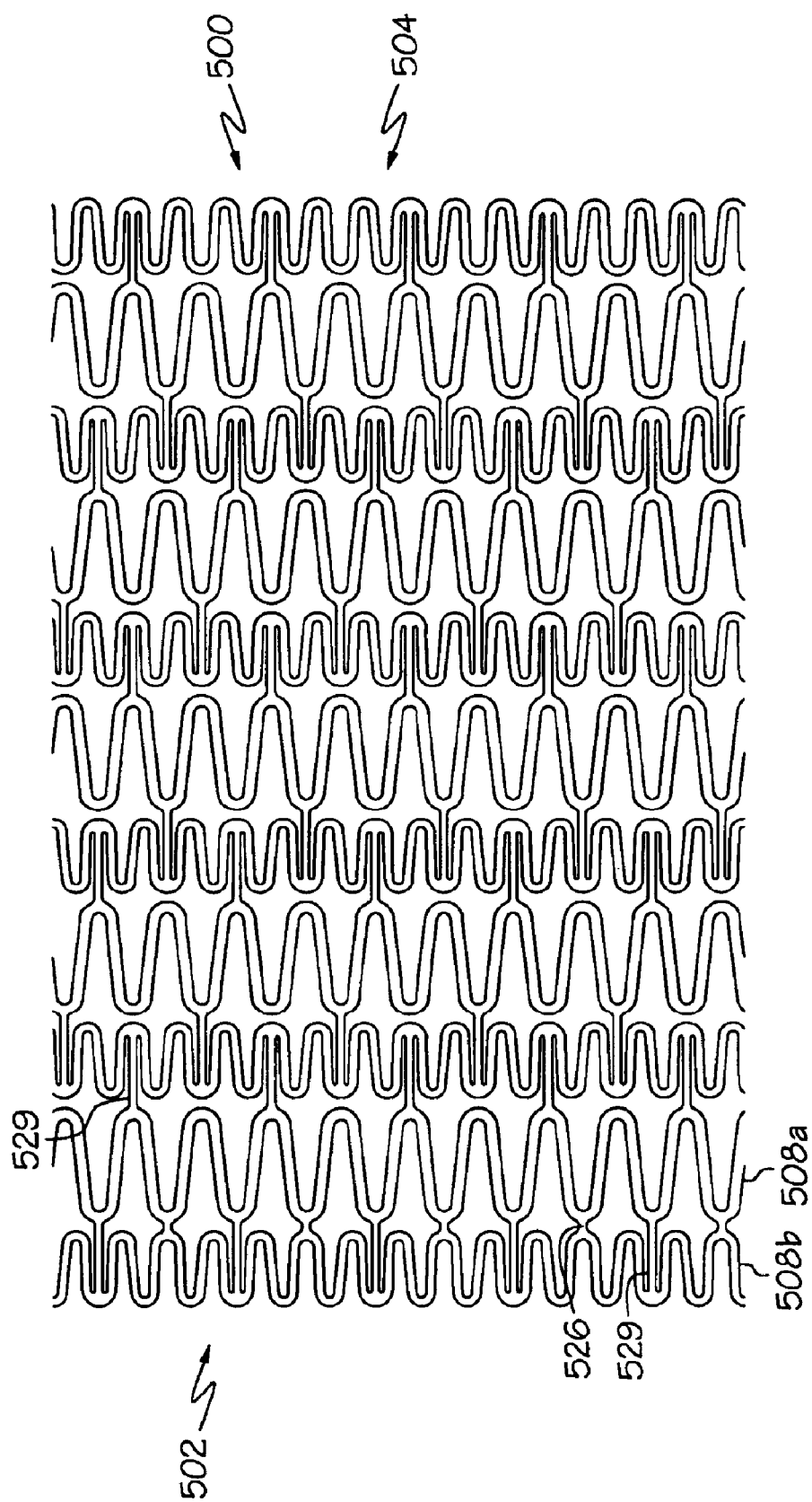

In the embodiment of FIG. 40, proximal end 502 and distal end 504 of stent 500 terminate in second undulating bands 508*b*. First connectors 529 and very short second connectors 526 extend only between the proximal-most second undulating band 508*b* and the proximal-most first undulating band 508*a*. All other adjacent first and second undulating bands are joined only by connectors 529 of the same length. The invention also contemplates stents in which both the proximal-most and distal-most first and second undulating bands have longer connectors 529 and very short connectors 526 extending therebetween. The wavelength of the first and second undulating bands are provided in a 3:2 ratio. Other ratios may also be employed.

In the embodiment of FIG. 41, longitudinal connectors extend from every peak 510 on a first undulating band 508*a* with first connectors 529 alternating around the circumference of the stent with very short second connectors 526. The stent is arranged such that every first connector 529 is longitudinally adjacent a very short second connector 526. In the embodiment of FIG. 41, the first and second undulating bands are separated by a distance D which is approximately 0.85 times the width $W_{e1}$ of the ends of the first undulating band. The ratios of the first and second amplitudes, the first and second wavelengths and are all approximately 3:2. The ratio of the first and second widths $W_1$ and $W_2$ is approximately 1.3:1.

In one embodiment of the invention, the ratio of widths of first and second undulating bands is desirably substantially equal to the ratio of amplitudes of first and second undulating bands and is also desirably equal to the ratio of wavelengths of the first and second undulating bands.

Figure 42:
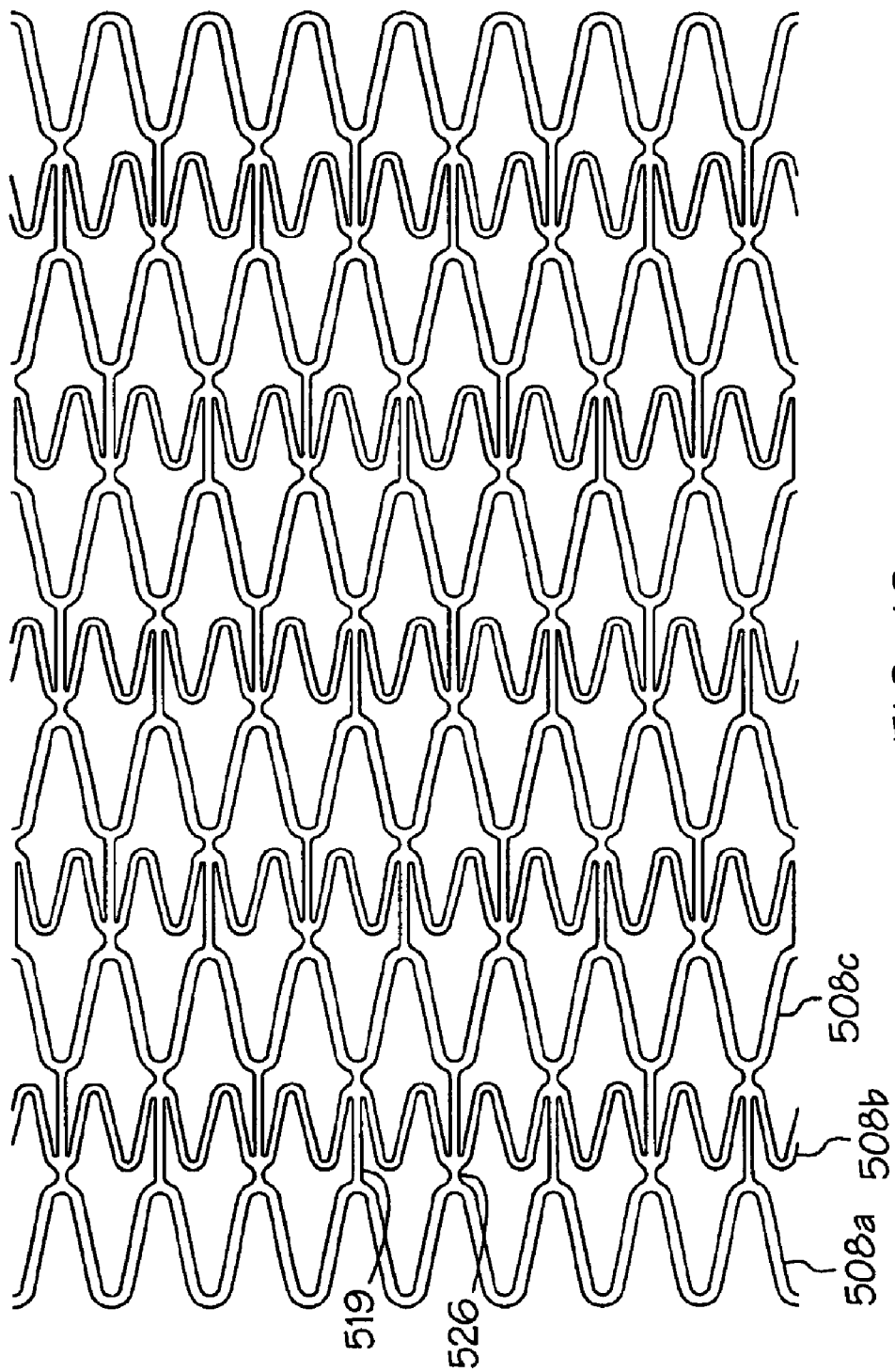

The embodiment of FIG. 42 is similar to that of FIG. 41 comprising 6 first undulating bands 508*a*, 508*c* etc. and 5 undulating second bands 508*b*, 508*d* etc. In the embodiment of FIG. 42, the ratio of the first and second widths $W_1$ and $W_2$ are all approximately 3:2.

Figure 43:
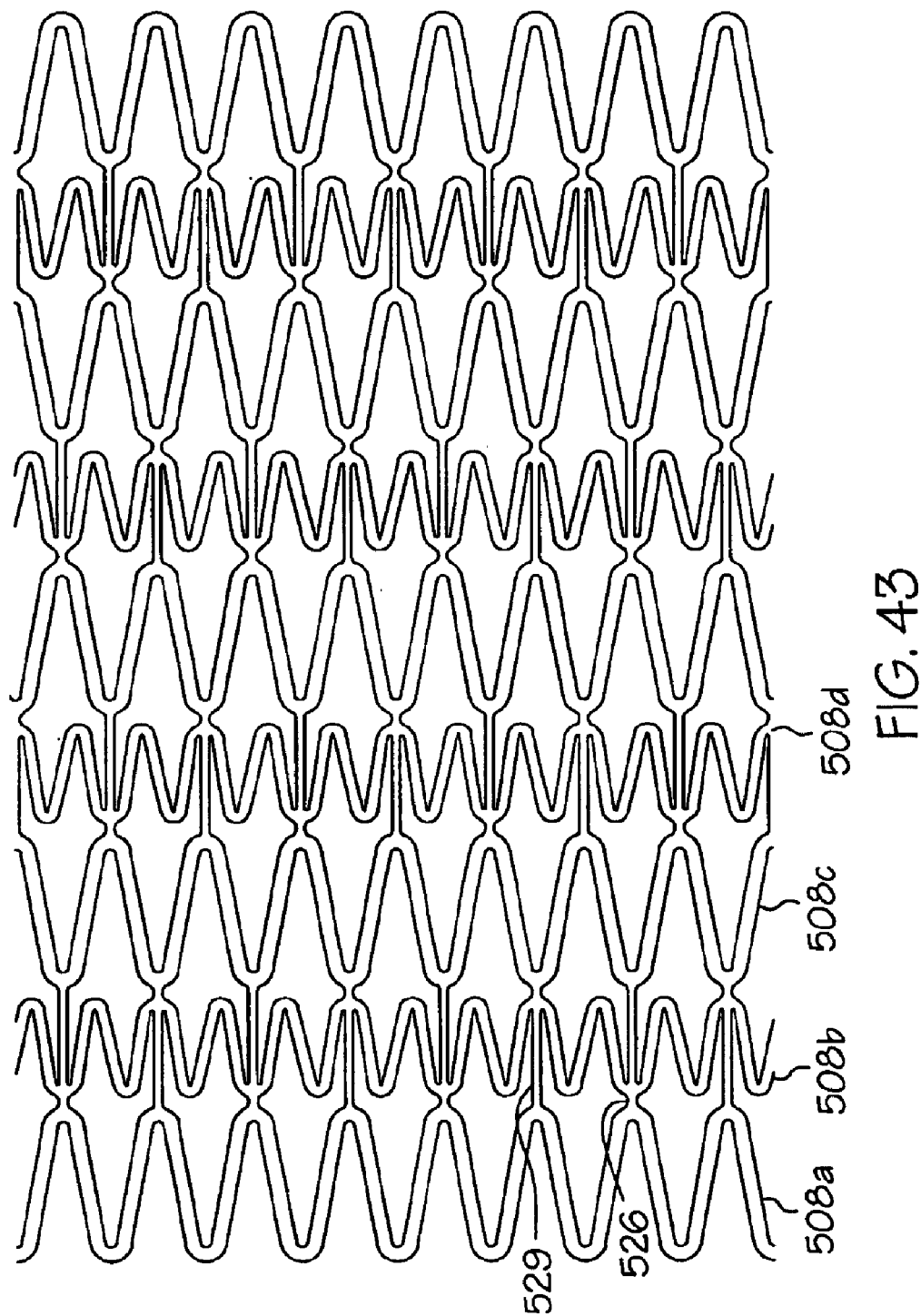

The embodiment of FIG. 43 is similar to that of FIGS. 41 and 42 comprising 5 first undulating bands 508*a*, 508*c* etc. and 4 second undulating bands 508*b*, 508*d* etc. In the embodiment of FIG. 42, the ratio of the first and second widths $W_1$ and $W_2$ are all approximately 3:2.

Figure 44:
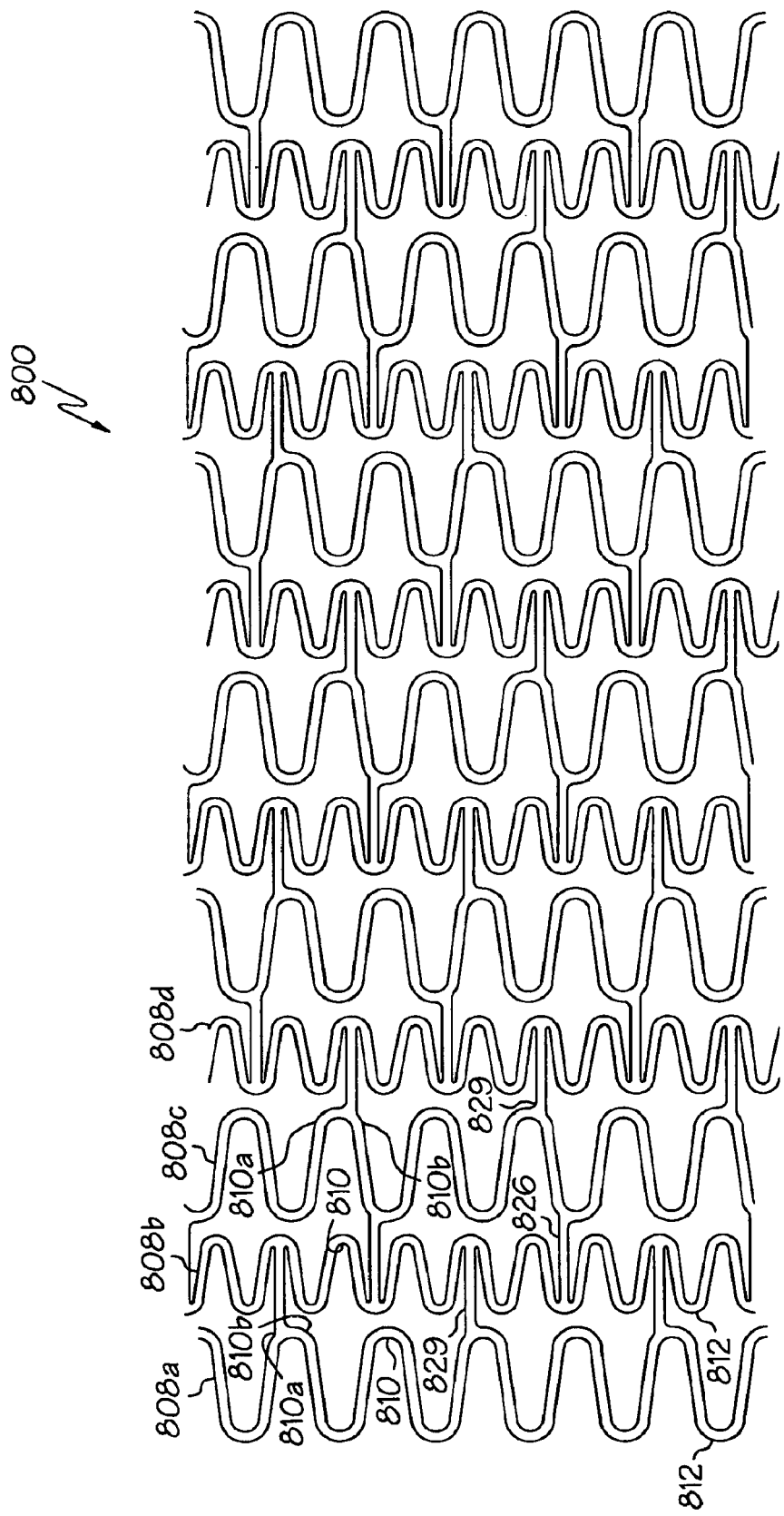

Any of the stents disclosed herein may be modified by providing connectors which extend from the sides of peaks and/or troughs or from positions between peaks and trough. An example of the former has been shown above in FIG. 7. Other examples of such stents are provided in FIGS. 44–47. As shown in FIG. 44, stent 800 comprises one or more first undulating bands 808*a* and one or more second undulating bands 808*b*. Desirably, the wavelength of amplitude of first undulating band 808*a* is greater than the wavelength of amplitude of second undulating band 808*b*. First connectors 829 extend asymmetrically from a side 810*a* of a peak 810 on first undulating band 808*a* to the peak 810 on second undulating band 808*b*. Desirably, first connectors 829 extend to the center of peaks 810 on second undulating bands 808*b*. It is also within the scope of the invention for the first connectors to extend to a side of peak 810 on second undulating band 808*b*.

Stent 800 of FIG. 44 further comprises one or more second connectors 826 which extend distally between a trough 812 on second undulating band 808*b* and a trough 812 on first undulating band 808*c*.

Stent 800 further comprises second undulating band 808*d*. One or more connectors 829 extend between sides 810*b* of peaks 810 of first undulating band 808*c* and peaks 810 of second undulating band 808*d*.

As shown in FIG. 44, longitudinally successive connectors 829 extend, alternately, from first sides 810*a* of peaks and second sides of peaks 810*b* of successive first undulating bands.

Figure 45:
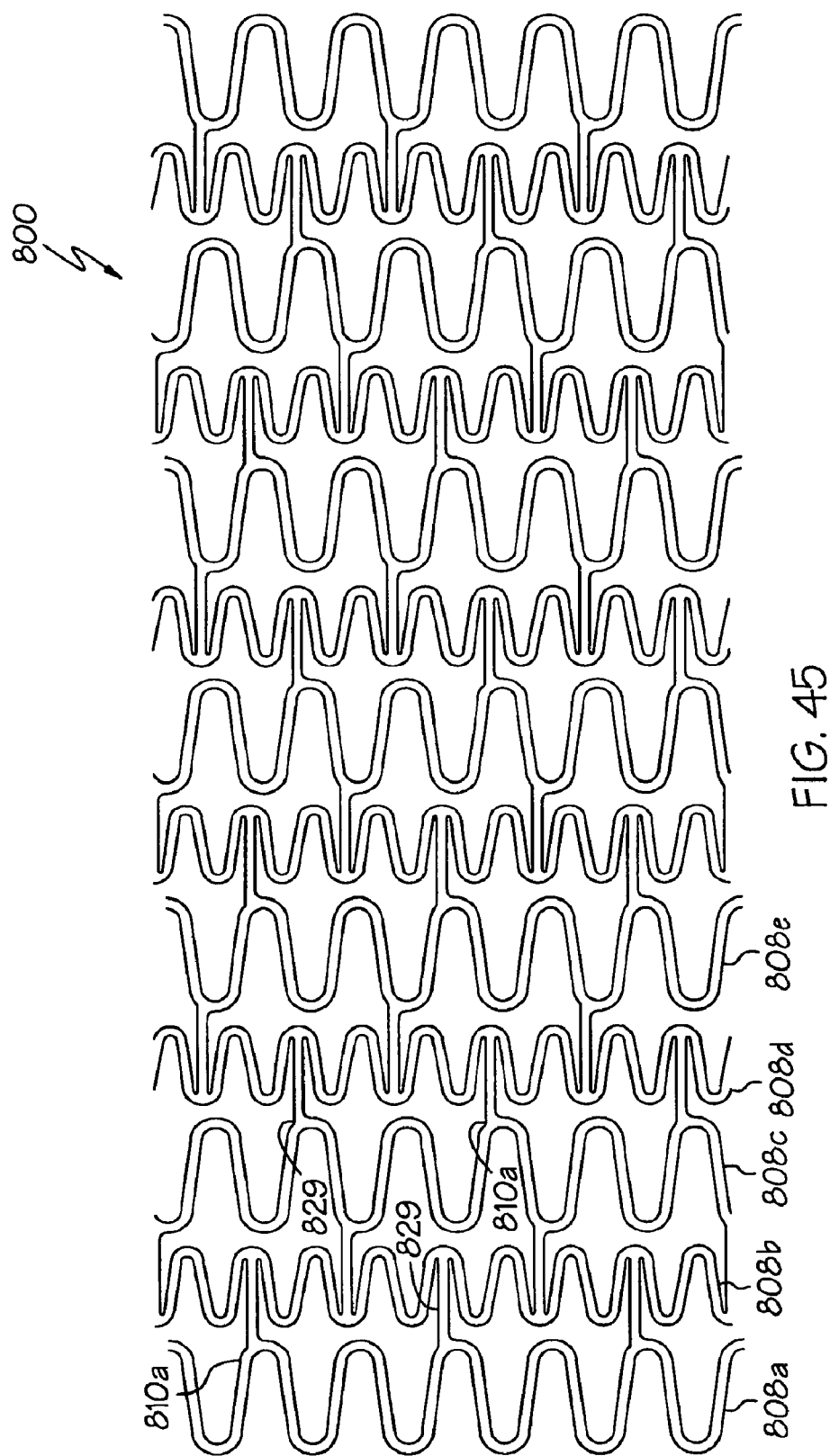

An embodiment of the invention in which longitudinally successive connectors 829 extend from the same side 810*a* of peaks of successive first undulating bands 808*a*, 808*c* etc. is shown generally at 800 in FIG. 45.

Figure 46:
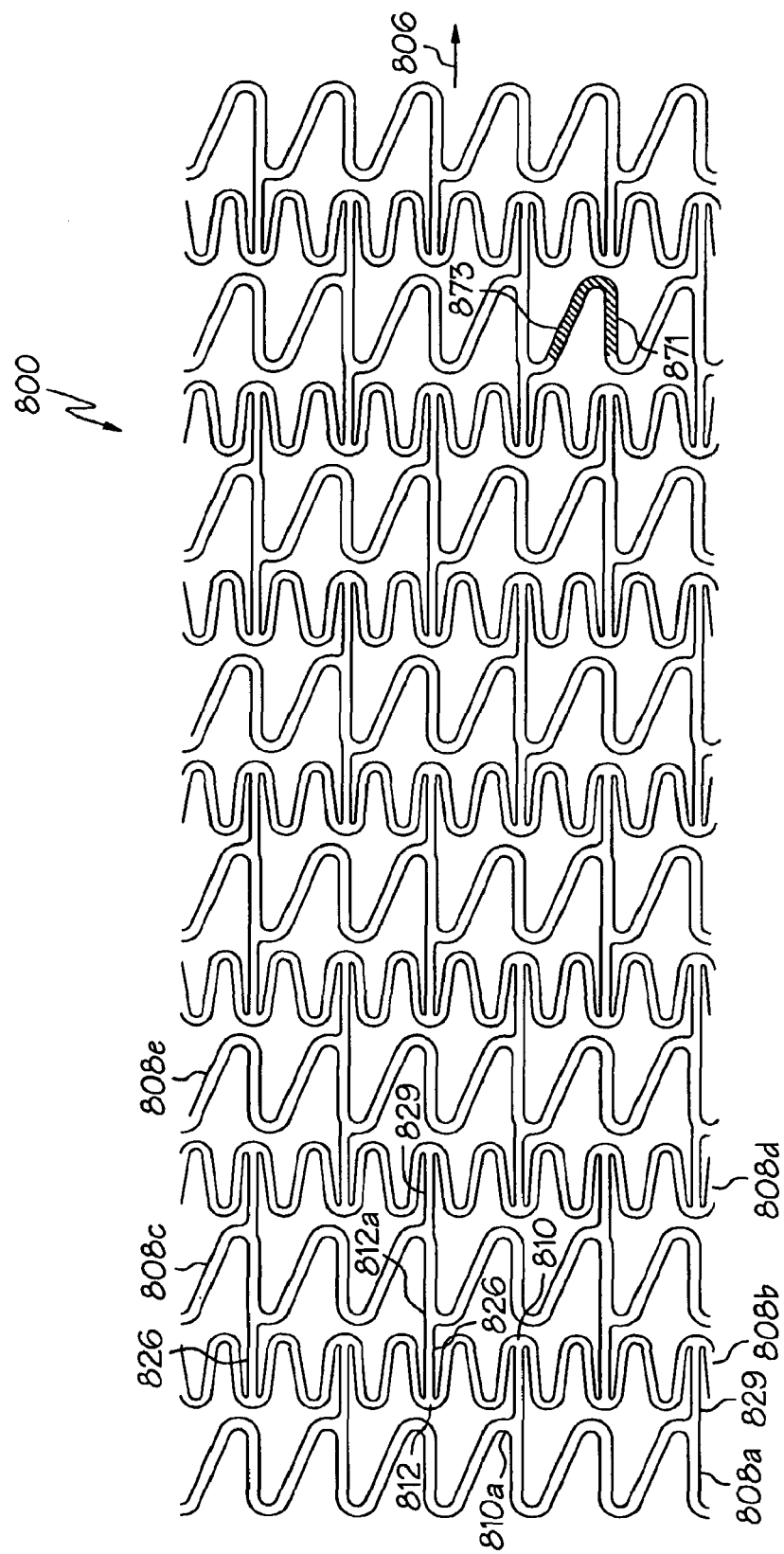

Additional examples of stents having connectors which extend from sides of peaks and/or troughs are shown in FIG. 46. Stent 800 of FIG. 47 comprises a first undulating band 808*a* which is connected to a second undulating band 808*b* via one or more connectors 829 which extend from side 810*b* of peak 810 to peak 810 of second undulating band 808*b*. Second undulating band 808*b* is connected to first undulating band 808*c* via one or more connectors 826 which extend from troughs 812 of second undulating band to sides 812*a* of troughs 812.

It is noted that in the embodiment of FIG. 46, successive second undulating bands are connected one to the other via longitudinal connectors which include longitudinally adjacent connectors 826 and 829 and a portion of a first undulating band.

It is also noted that in the embodiment of FIG. 46, first undulating bands 808*a*, 808*c*, etc. are formed of a plurality of interconnected alternating struts 871 which are parallel to longitudinal axis 806 of the stent and struts 873 which are a slanted at an oblique angle relative to the longitudinal axis of the stent. The invention also contemplates embodiments in which the second undulating bands include alternating parallel and obliquely oriented struts.

Figure 47:
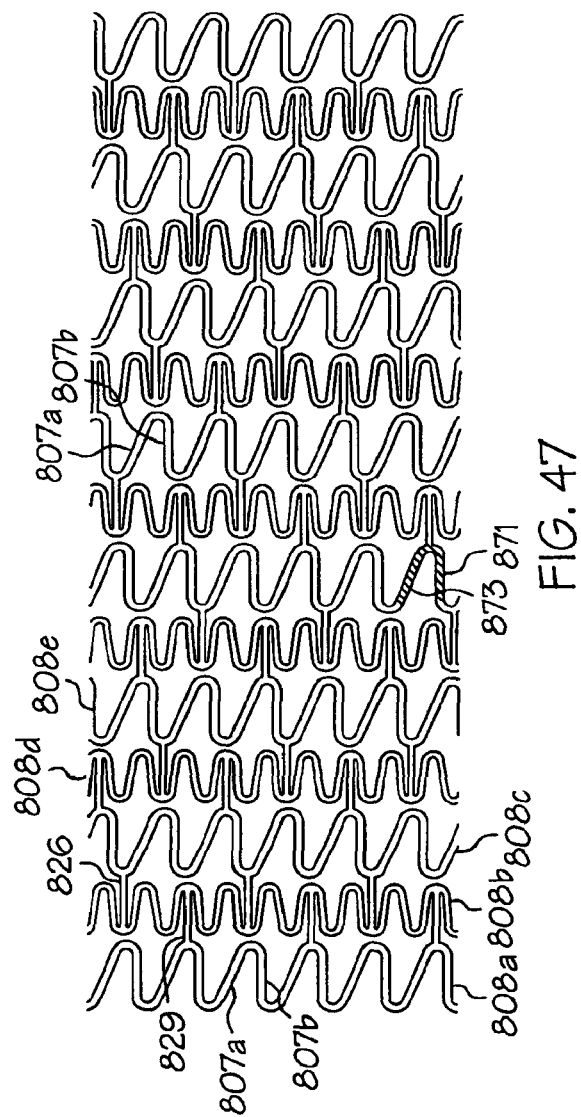

Another stent in accordance with the instant invention is shown generally at 800 in FIG. 47. The stent of FIG. 47 includes first undulating bands 808*a*, 808*c*, 808*e*, etc. which comprise struts 871 which are parallel to longitudinal axis 806 of the stent and struts 873 which are a slanted at an oblique angle relative to the longitudinal axis of the stent. Adjacent undulating bands are connected via one or more connectors 829 which extend distally from peaks 810 on first undulating bands 808*a* to peaks on second undulating bands 808*b* and from distally from troughs 810 on second undulating bands 808*b* to troughs 812 on first undulating bands 808*c*.

Any of the other inventive stents disclosed herein may be provided with first and/or second bands of any other geometry disclosed herein including the geometries shown in FIGS. 16–22.

In any of the above embodiments, by varying the amplitude and wavelength of the undulating bands as well as the thickness of the undulating bands rather than the widths of the undulating bands, it may also be possible to provide a stent having alternating bands of different wavelength and amplitude where the alternating bands are of like strength.

It is further within the scope of the invention for adjacent undulating bands to be made of a different materials or of materials which are treated differently from one another so that adjacent bands of different wavelength and amplitude may have the same strength. Examples of different treatments include differently annealing some of the undulating bands or subjecting some of the undulating bands to a different heat treatment.

In the embodiment of FIGS. 35a–c, the first undulating band is stronger than the third undulating band and the bands may be made of different materials or differently treated materials. Similarly, the second undulating band may be made of a different material or a material which is treated differently than the fourth undulating band so that the second undulating band is stronger than the fourth undulating band.

In any of the above embodiments, the separation between adjacent undulating bands will desirably be from approximately one half to three times the width of the wider of the two adjacent undulating bands and more desirably one to two times the width of the wider of the two adjacent undulating bands.

Also desirably, in any of the above embodiments, the width of the apices or turns of the undulating bands will range from 50% smaller to 100% wider than the width of the straight portions of the undulating bands. More desirably, the width of the apices or turns of the undulating bands will be approximately 0–50% wider than the width of the straight portions of the undulating bands and, most desirably, 15–40% wider.

The invention is also directed to a stent comprising a first undulating band of a first wavelength and amplitude and a second undulating band of a second wavelength and amplitude where the first wavelength and amplitude are larger than the second wavelength and amplitude and where the first and second undulating bands are characterized by the same total pathlength as the bands are traversed about the periphery of the stent. The stent may comprise additional undulating bands each of which is of the same total path length or of different path lengths. Desirably, the total path length about the periphery of the stent of each undulating band is substantially the same. Any of the embodiments disclosed herein may be provided with first and second undulating bands of the same pathlength, or with first undulating bands longer or shorter than the second undulating bands.

The invention is also directed to a stent comprising a first undulating band of a first wavelength and amplitude and a second undulating band of a second wavelength and amplitude where the first undulating band is of the same radial strength as the second undulating band. The stent may comprise additional undulating bands each of which is of the same radial strength as the first and second undulating bands or of different strengths. Desirably, the radial strength of each undulating band is substantially the same.

It is understood that any of the inventive stents disclosed herein may be modified so that larger wavelength and amplitude undulating bands are of a narrower width than the smaller amplitude undulating bands. An example of this is shown in FIG. 48. First undulating band 908a is of larger amplitude and wavelength than second undulating band 908b but is of narrower width $W_1$ than width $W_2$ of second undulating band 908b. The stent of FIG. 48 may include additional first and second undulating bands.

Figure 49:
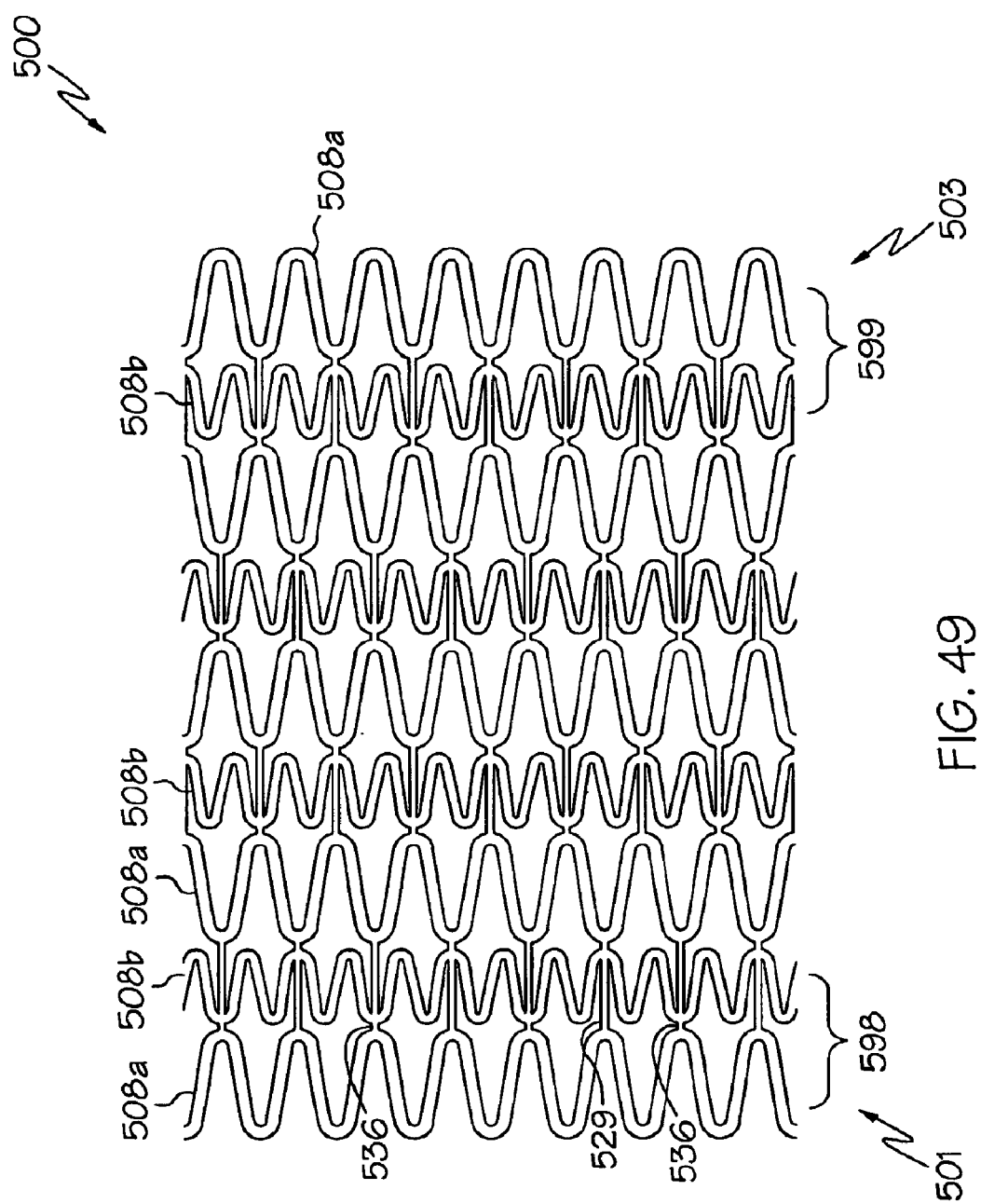

Another inventive stent is shown generally at 500 in FIG. 49. Stent 500 of FIG. 49 includes a plurality of first undulating bands 508a of a first wavelength and amplitude and a plurality of second undulating bands 508b of a second wavelength and amplitude. Desirably, as shown in FIG. 49, the first wavelength and amplitude exceeds the second wavelength and amplitude. Also desirably, as shown in FIG. 49, the first undulating band is wider than the second undulating band. At least one pair 598 of adjacent first and second undulating bands 508a and 508b have one or more substantially longitudinal first connectors of a first length 529 extending therebetween and one or more very short second connectors 526 extending therebetween. Very short second connectors 526 extend between peaks and troughs which are circumferentially aligned and facing one another and provide stiffness to the stent. At least another pair 599 of adjacent first and second undulating bands 508a and 508b have only substantially longitudinal first connectors of a first length 529 extending therebetween and no additional connectors extending between the two bands. By providing small connectors between some adjacent bands but not other bands, it is possible to provide a stent having varying stiffness characteristics. In the embodiment of FIG. 49, short connectors extend between the first four adjacent undulating bands at the proximal end of the stent. Thus, the proximal end of the stent is stiffer than the middle of the stent and the distal end of the stent. More specifically, the proximal-most two undulating bands of the stent are stiffer than the distal-most two undulating bands of the stent. Also, the proximal-most two undulating bands of the stent are stiffer than two adjacent undulating bands in the middle of the stent.

More generally, the invention in one embodiment is directed to a stent having a plurality of undulating bands where some of the undulating bands are interconnected by longitudinal connectors and second very short connectors and others of the undulating bands are interconnected only by longitudinal connectors to achieve greater stiffness in regions of the stent having the very short connectors and lesser stiffness in regions of the stent lacking shorter connectors. As an example of such a stent, the proximal end may be stiffer than the middle of the stent and/or the distal end. An inventive stent may also have a stiffer middle portion and less stiff end portions. Yet another inventive stent may have a stiffer distal end portion and a less stiff center and proximal end. Yet another inventive stent may have a stiffer proximal end (or distal end) and a stiffer center portion and a less stiff distal end (or proximal end).

Figure 50:
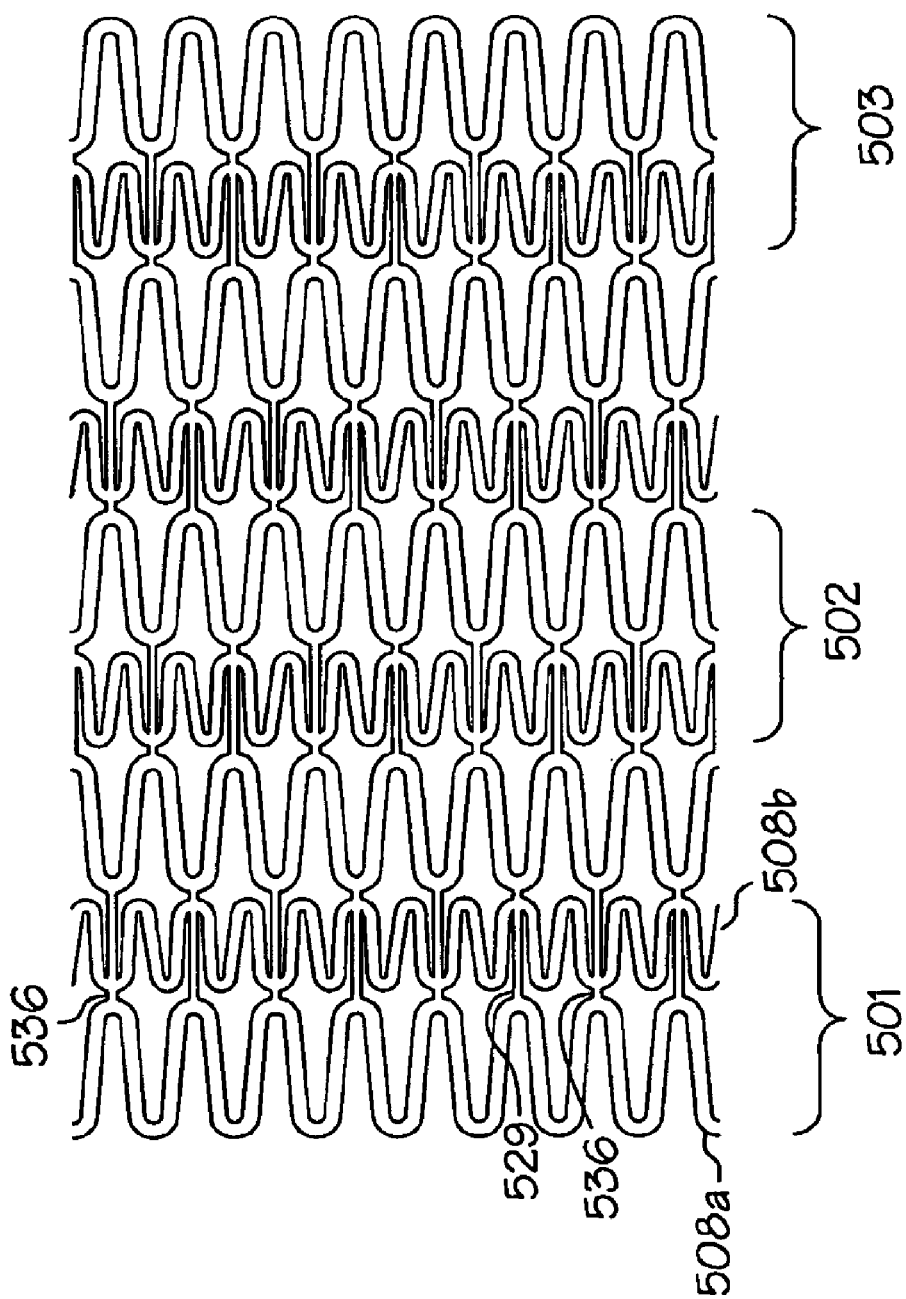

It is further within the scope of the invention to tailor the stiffness of the stent by varying the number of very short connectors extending between facing peaks and trough of adjacent undulating bands. As shown in FIG. 50, the number of very short connectors 526 between adjacent undulating bands diminishes from one end of the stent to the other end of the stent. The proximal-most two first undulating bands 508a and 508b of the stent have very short connectors extending from every other peak. The middle-most undulating band of the stent, a first undulating band, has fewer very short connectors than the proximal-most first undulating bands. As such, the proximal end 501 of the stent is stiffer than the middle portion 502 of the stent and the distal portion 503 of the stent.

The invention is also directed to a stent such as that shown by way of example in FIG. 39 as well as in other of the figures, comprising a plurality of undulating bands 708*a–e* having peaks 770, 772 and troughs 771, 773. The undulating bands including first and second undulating bands 708*a, c, e,* and 708*b,d,* which alternate with one another along the length of the stent. The second undulating bands 708*b,d* have more peaks 772 and troughs 773 than the first undulating bands 708*a,c,e*. The first undulating bands are of greater longitudinal extent than the second undulating bands. The stent further comprises a plurality of longitudinal connectors 726 and 729, some of which (729) extend in-between peaks of second undulating bands and peaks of first undulating bands which are proximally adjacent thereto and some of which (726) extend between troughs of second undulating bands and troughs of first undulating bands which are distally adjacent thereto. Desirably, the first undulating bands are wider than the second undulating bands. Desirably, as is the case with the stent of FIG. 39 as well as other of the stents disclosed herein, the proximal and distal ends are of substantially the same stiffness.

Optionally, as shown by way of example in FIG. 28 as well as in other figures, the stent further comprises a plurality of very short connectors 536, each very short connector extending between a peak on one of the undulating bands and a trough on another of the undulating bands which is adjacent thereto, the peak and the trough circumferentially aligned and facing one another. The very short connectors are provided between first and second undulating bands which are adjacent one another.

As shown in the embodiment of FIG. 28, the very short connectors 536 optionally are provided between some first and second undulating bands which are adjacent one another but not between all adjacent first and second undulating bands.

As shown in the embodiment of FIG. 50, the number of very short connectors 536 extending between the end-most first and second undulating bands 501 at the first end of the stent optionally exceeds the number of very short connectors extending between the end-most first and second undulating bands 503 at the second end of the stent. As further shown in in the embodiment of FIG. 50, The second end region 503 does not having any very short connectors. The first end region 501 of the stent is stiffer than the second end region 503.

As shown by way of example in FIG. 49, in one embodiment of the invention, the number of short connectors 536 may diminish from one end 501 of the stent to the other end 503 of the stent.

As shown by way of example in FIG. 29*a*, in another embodiment of the invention, the stent may have a first end region 501 and a second end region 503, the first end region including one first undulating band and one second undulating band with very short connectors 536 extending therebetween and the second end region including one first undulating band and one second undulating band with very short connectors 536 extending therebetween with the first end region having the same number of very short connectors as the second end region.

In another embodiment, as shown by way of example in FIG. 36*a*, the invention is directed to a stent, shown generally at 700, having a proximal end and a distal end, the stent comprising a plurality of undulating bands having peaks and troughs, the undulating bands including first 708*a,c,e* and second 708*b,d* undulating bands which alternate with one another along the length of the stent. The second undulating bands have more peaks 710 and troughs 712 than the first undulating bands and the first undulating bands are of greater longitudinal extent than the second undulating bands. The stent further comprises a plurality of longitudinal connectors extending from second undulating bands to first undulating bands which are adjacent thereto. Each second undulating band which is proximally adjacent to a first undulating band and distally adjacent to another first undulating band is connected to the proximally adjacent first undulating band via a plurality of longitudinal connectors 726 extending from the distal end of the second undulating band to the distal end of the proximally adjacent first undulating band and is connected to the distally adjacent first undulating band via a plurality of longitudinal connectors 729 extending from the proximal end of the second undulating band to the proximal end of the distally adjacent first undulating band. Desirably, as shown in FIG. 36*a,* the first undulating bands 708*a,c,e* are wider than the second undulating bands 708*b,d,f*. Also desirably, as shown in FIG. 36*a*, all undulating bands which are adjacent one another are spaced apart from one another by a constant distance.

In yet another embodiment of the invention, adjacent undulating bands are spaced apart from one another with the spacing between adjacent first and second undulating bands at at least one of the ends of the stent exceeding the spacing between adjacent first and second undulating bands in the middle of the stent. Optionally, the spacing between adjacent first and second undulating bands at both ends of the stent may exceed the spacing between adjacent first and second undulating bands in the middle of the stent.

In yet another embodiment, the invention is directed to a stent with adjacent first and second undulating bands, as described above, which are spaced apart from one another, with the spacing between adjacent first and second undulating bands at at least one of the ends of the stent less than the spacing between adjacent first and second undulating bands in the middle of the stent. Optionally, the spacing between adjacent first and second undulating bands at both ends of the stent may be less than the spacing between adjacent first and second undulating bands in the middle of the stent.

In the above-described embodiments having a non-constant spacing of the undulating bands, the undulating band which is proximal-most in the stent is optionally of greater longitudinal extent than one of the first undulating bands and has the same number of peaks and troughs as one of the first undulating bands and the undulating band which is adjacent thereto is of greater longitudinal extent than one of the second undulating bands and has the same number of peaks and troughs as one of the second undulating bands. Desirably, the undulating band which is distal-most in the stent is of greater longitudinal extent than one of the first undulating bands and has the same number of peaks and troughs as one of the first undulating bands and the undulating band which is adjacent thereto is of greater longitudinal extent than one of the second undulating bands and has the same number of peaks and troughs as one of the second undulating bands. More desirably, the undulating band which is proximal-most in the stent is of greater longitudinal extent than one of the first undulating bands and has the same number of peaks and troughs as one of the first undulating bands and the undulating band which is adjacent thereto is of greater longitudinal extent than one of the second undulating bands and has the same number of peaks and troughs as one of the second undulating bands. Also more desirably, the undulating band which is distal-most in the stent is of greater longitudinal extent than one of the first undulating bands and has the same number of peaks and troughs as one of the first undulating bands and the undulating band which is adjacent thereto is of greater longitudinal extent than one of the second undulating bands and has the same number of peaks and troughs as one of the second undulating bands. Any of the stents disclosed herein may easily be modified to provide such a stent.

Optionally, the stent may comprise at least one pair of undulating first and second bands which are adjacent one another and are further connected one to the other by a plurality of very short connections extending between circumferentially aligned peaks and troughs which face one another.

In yet another embodiment of the invention, the first and second undulating bands each comprise a plurality of alternating peaks and troughs with struts extending therebetween. At least some of the struts are non-parallel to the longitudinal axis of the stent.

Optionally, as shown by way of example in FIG. 47, every other strut 807a of every first undulating band 808a,c,e, is non-parallel to the longitudinal axis of the stent and the remaining struts 807b of the first undulating bands are parallel to the longitudinal axis of the stent.

Figure 51:
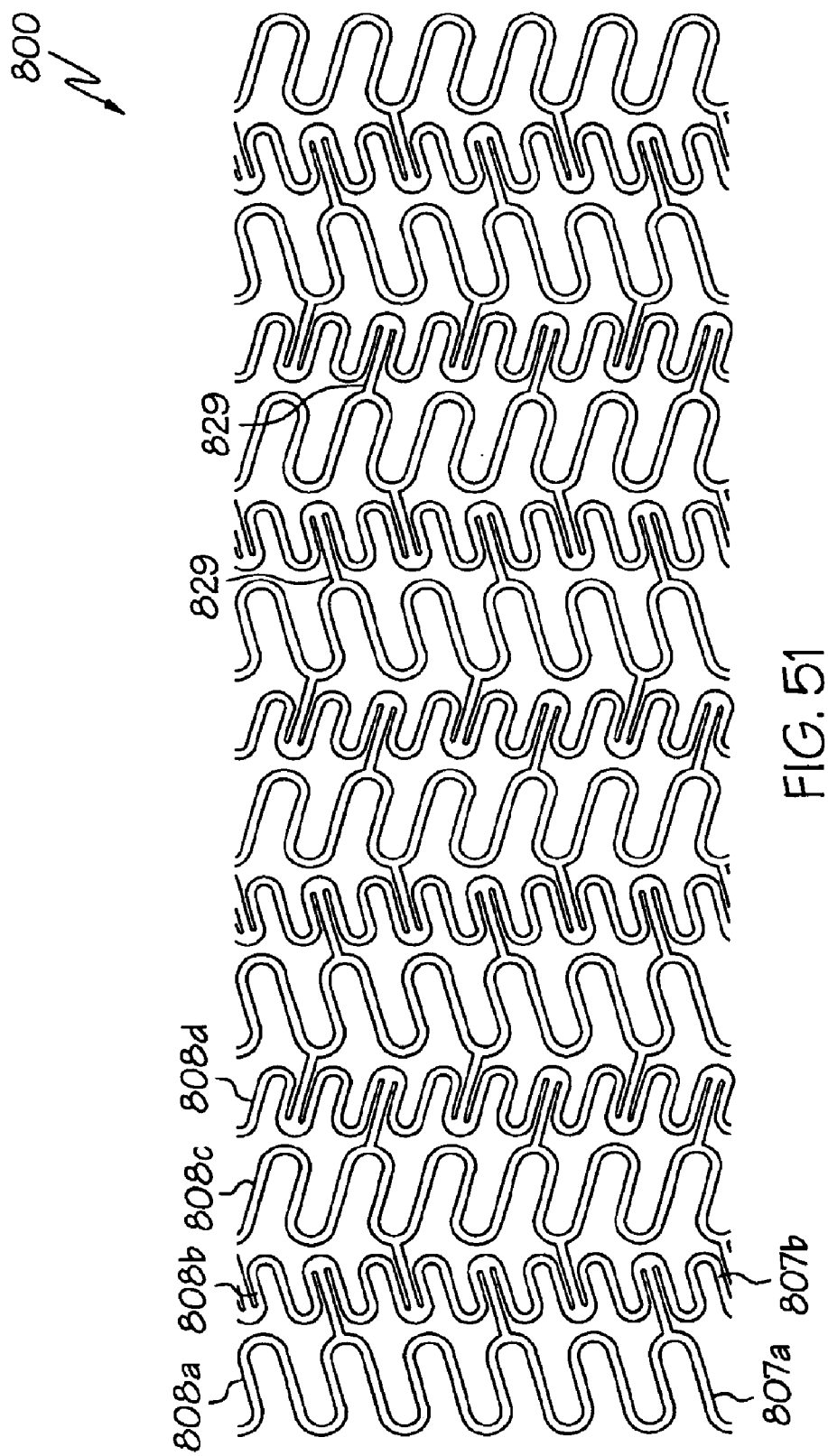

In yet another embodiment of the invention, as shown by way of example in FIG. 51, all of the struts 807 of stent 800 are non-parallel to the longitudinal axis of the stent and, within a given undulating band 808a,b are substantially parallel with one another. All of the undulating bands may have struts which are parallel with one another (not shown) or the struts of some of the undulating bands may be oriented in opposite directions, as shown in FIG. 51. Specifically, in the stent of FIG. 51, the struts 807a in the proximal-most first undulating band 808a are substantially parallel to one another and the struts 807b in the proximal-most second undulating band 808b are substantially parallel to one another and parallel to the struts in the proximal-most first undulating band. The struts in the next two undulating bands 808c and 808d are parallel to one another but are disposed in an opposite direction relative to the struts in undulating bands 808a and 808b. Adjacent undulating bands are connected via connectors 829. First undulating bands 808a,c are longer than second undulating bands 808d,e and desirably are wider as well. Also desirably, the first undulating bands have fewer peaks and troughs than the second undulating bands.

Optionally, not shown, the struts in the first undulating bands may incline in a first direction relative to the longitudinal axis of the stent and the struts in the second undulating bands may incline in a second direction opposite the first direction about the longitudinal axis of the stent.

The invention is also directed to embodiments in which the orientation of the struts in the first undulating bands alternates between consecutive first undulating bands relative to the longitudinal axis as shown in FIG. 51. Optionally, the orientation of the struts in the second undulating bands may alternate between consecutive second undulating bands relative to the longitudinal axis as shown in FIG. 51.

Figure 52:
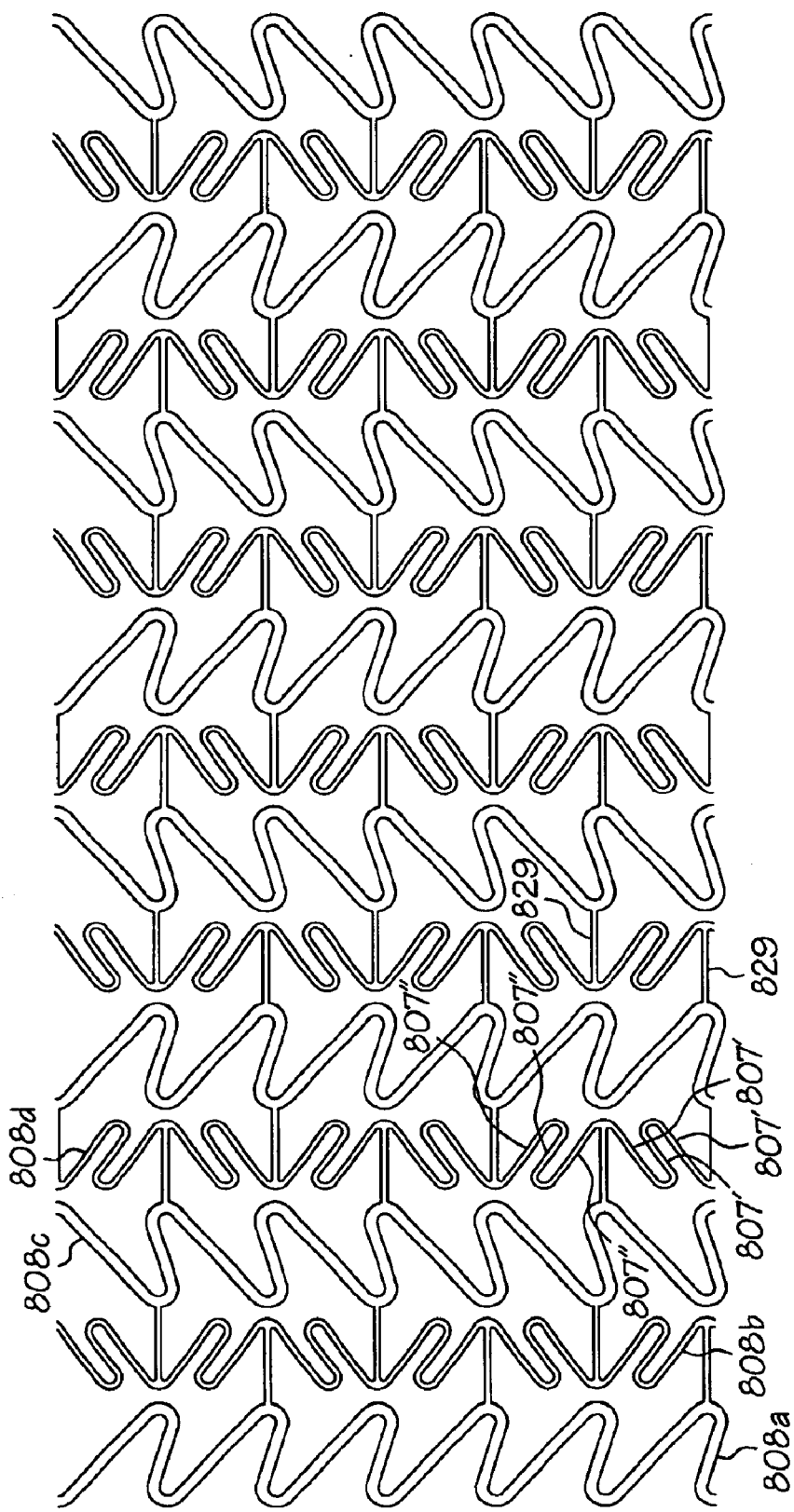

In yet another embodiment, as shown in FIG. 52, each second undulating band 808b,d may comprise a plurality of consecutive struts 807' oriented in a first direction relative to the longitudinal axis of the stent and a plurality of consecutive struts 807" oriented in a second direction opposite the first direction and relative to the longitudinal axis of the stent. Adjacent undulating bands are connected via connectors 829. First undulating bands 808a,c are longer than second undulating bands 808d,e and desirably are wider as well. Also desirably, the first undulating bands have fewer peaks and troughs than the second undulating bands.

Any of the inventive stents disclosed herein may also be modified so that all of the undulating bands are of the same width. The inventive stents disclosed herein may also be modified so that the first undulating bands are of a greater radial rigidity than the second undulating bands, of the same radial rigity or of a lesser radial rigidity than the second undulating bands.

Desirably, in any of the embodiments disclosed above, all of the undulating bands are of the same length. However, it is also within the scope of the invention for the first and second undulating bands to be of different lengths.

The invention is directed to any of the above stents whether in the unexpanded state or in the expanded state.

The invention is further directed to bifurcated stents where one or more portions of the bifurcated stent has the above-disclosed structure. For example, each of the legs of a bifurcated stent or a single leg of the bifurcated stent or the entirety of the bifurcated stent may have a structure such as that disclosed above. In one embodiment of the invention one branch and/or the trunk of a bifurcated stent may comprise a stent with long connectors such as are shown, for example, in FIG. 26a and another branch may comprise a stent with short connectors such as are shown, for example, in FIG. 34. Additional details concerning bifurcated stents may be found in U.S. Pat. No. 5,916,263 as well as in U.S. application Ser. No. 09/659,571.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the undulating bands and/or longitudinal connectors may increase or decrease along portions of the stent or along the entire length of the stent. The amplitude and wavelength of several successive first undulating bands may remain constant while the width and/or thickness of the successive first undulating bands decreases. Similarly, the amplitude and wavelength of several successive second undulating bands may remain constant while the width and/or thickness of the successive second undulating bands decreases.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and welding the sheet, by electrode discharge machining, or by molding the stent with the desired design.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel-titanium alloys generically known as "nitinol", platinum/tungsten alloys and titanium alloys. such as stainless steel, tantalum and elgiloy. The invention also contemplates the use of more than one material in the inventive stents. For example, the first undulating bands and the second undulating bands may be made of different materials. Optionally, the connectors may be made of a different material than the first and/or second undulating bands.

The inventive stents may be provided in mechanically expandable form, in self-expanding form or as a hybrid of the two. Mechanically expandable stents, in accordance with the invention, may be expanded using any suitable mechanical device including a balloon.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends, copolymers, mixtures, blends and copolymers.

The inventive stents may find use in coronary arteries, renal arteries, peripheral arteries including illiac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus and the prostate.

Suitable stent delivery devices such as those disclosed in U.S. Pat. Nos. 6,123,712, 6,120,522 and 5,957,930 may be used to deliver the inventive stents to the desired bodily location. The choice of delivery device will depend on whether a self-expanding or balloon expandable stent is used. The inventive stents may be delivered in conjunction with one or more stent retaining sleeves. An example of stent retaining sleeves is disclosed in U.S. provisional application No. 60/238,178.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2, or on claim 1; etc.).

The disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent having a proximal end and a distal end comprising
 a first undulating band forming a closed path about a whole circumference of the stent, the first undulating band comprising a series of alternating first peaks and first troughs, the first peaks oriented in a distal direction, the first troughs oriented in a proximal direction, the first undulating band having a first wavelength and a first amplitude,
 a second undulating band forming a closed path about a whole circumference of the stent, the second undulating band comprising a series of alternating second peaks and second troughs, the second peaks oriented in a distal direction, the second troughs oriented in a proximal direction, the second undulating band having a second wavelength and a second amplitude, the second amplitude different from the first amplitude, the second wavelength different from the first wavelength,
 a third undulating band comprising a series of alternating third peaks and third troughs, the third peaks oriented in a distal direction, the third troughs oriented in a proximal direction, the third undulating band having a third wavelength and a third amplitude, the third wavelength equal to the first wavelength and the third amplitude equal to the first amplitude,
 a plurality of longitudinally oriented first connectors extending between first peaks and second peaks, and
 a plurality of longitudinally oriented second connectors extending between second troughs and third troughs.

2. The stent of claim 1 comprising at least three first connectors equally spaced about the periphery of the stent.

3. The stent of claim 1 wherein the first amplitude is greater than the second amplitude.

4. The stent of claim 4 wherein the first wavelength is greater than the second wavelength.

5. The stent of claim 1 wherein the first wavelength is greater than the second wavelength.

6. The stent of claim 1 comprising three first connectors equally spaced about the periphery of the stent and three second connectors equally spaced about the periphery of the stent.

7. The stent of claim 7 wherein first and second connectors which are circumferentially adjacent are separated by at least one second peak and one second trough.

8. The stent of claim 1 further comprising a fourth undulating band comprising a series of alternating fourth peaks and fourth troughs, the fourth peaks oriented in a distal direction, the fourth troughs oriented in a proximal direction, the fourth undulating band having a fourth wavelength and a fourth amplitude, the fourth wavelength equal to the second wavelength and the fourth amplitude equal to the second amplitude, a plurality of longitudinally oriented third connectors extending between third peaks and fourth peaks.

9. The stent of claim 9 wherein the first, second and third connectors are circumferentially displaced from one another.

10. The stent of claim 1 wherein the first wavelength is 1.5 times the second wavelength.

11. The stent of claim 1 wherein the first undulating band is characterized by a first width and the second undulating band is characterized by a second width different from the first width.

12. The stent of claim 12 wherein the width of the first undulating band exceeds the width of the second undulating band.

13. The stent of claim 9 wherein the first undulating band is characterized by a first width, the second undulating band is characterized by a second width, the third undulating band is characterized by a third width and the fourth undulating band is characterized by a fourth width, the first and third width equal to one another, the second and fourth widths equal to one another and the first width greater than the second width.

14. A stent comprising a plurality of first expansion cells, each first expansion cell having a proximal end,
a distal end,
a first side extending between the proximal and distal ends, and
a second side opposite the first side and extending between the proximal and distal ends,
the proximal end of the cell consisting of an undulating segment having
  a first trough opening in a distal direction,
  a second trough opening in a distal direction, and
  a first peak opening in a proximal direction, the first peak disposed between the
  first trough and the second trough,
the distal end of the cell consisting of an undulating segment having a first half peak and a second half peak, three troughs opening in a distal direction and two peaks opening in a proximal direction, the peaks and troughs alternating with one another and disposed between the first and second half peaks,
the first and second sides being substantially straight, longitudinally extending members
wherein the first expansion cells form closed bands, which extend all the way around the circumference of the stent.

15. The stent of claim 14 further comprising second expansion cells, the second expansion cells mirror images of the first expansion cells.

16. The stent of claim 15 wherein the second expansion cells are arranged in circumferential bands extending about the periphery of the stent.

17. The stent of claim 16 wherein the bands of first expansion cells and the bands of second expansion cells alternate along the length of the stent.

18. The stent of claim 17 wherein first and second expansion cells which are adjacent one another are staggered about the circumference of the stent.

19. The stent of claim 15 comprising a circumferential band of first expansion cells at one end of the stent and a circumferential band of second expansion cells at the other end of the stent.

* * * * *

UNITED STATES PATENT AND TRADEMARK OFFICE
CERTIFICATE OF CORRECTION

PATENT NO.         : 6,896,696 B2                                    Page 1 of 5
APPLICATION NO. : 09/957983
DATED                  : May 24, 2005
INVENTOR(S)        : Burns Doran et al.

It is certified that error appears in the above-identified patent and that said Letters Patent is hereby corrected as shown below:

Front page, under "References Cited", add the following:
            --U.S. PUBLISHED DOCUMENTS

| | | | |
|---|---|---|---|
| 2001/0039447 A1 | 11/8/01 | Pinchasik et al. | 623/1.15 |
| 2002/0007211 A1 | 1/17/02 | Pinchasik et al. | 623/1.16 |
| 2002/0007212 A1 | 1/17/02 | Brown et al. | 623/1.16 |
| 2002/0022876 A1 | 2/21/02 | Richter et al. | 623/1.15 |
| 2002/0103529 A1 | 8/1/02 | Pinchasik et al. | 623/1.15 |
| 2003/0083736 A1 | 5/1/03 | Brown et al. | 623/1.16-- |

Front page, under "U.S. PATENT DOCUMENTS", add the following:

| | | | |
|---|---|---|---|
| --2,836,181 | 5/27/58 | Tapp | 606/155 |
| 3,105,492 | 10/1/63 | Jeckel | 623/1.44 |
| 3,272,204 | 9/13/66 | Artandi et al. | 606/151 |
| 3,490,975 | 1/20/70 | Lightwood et al. | 156/167 |
| 3,509,883 | 5/5/70 | Dibelius | 604/104 |
| 3,526,228 | 9/1/70 | Lyng | 606/151 |
| 3,562,820 | 2/16/71 | Braun | 623/23.64 |
| 3,635,215 | 1/18/72 | Shea et al. | 128/840 |
| 3,657,744 | 4/25/72 | Ersek | 128/898 |
| 3,771,526 | 11/13/73 | Rudle | 606/153 |
| 3,868,956 | 4/4/75 | Alfidi et al. | 606/194 |
| 3,993,078 | 11/23/76 | Bergentz et al. | 606/156 |
| 4,078,167 | 3/7/78 | Banas et al. | 219/121.11 |
| 4,127,761 | 11/28/78 | Pauly et al. | 219/121.84 |
| 4,130,904 | 12/26/78 | Whalen | 623/1.44 |
| 4,140,126 | 2/20/79 | Choudhury | 606/194 |
| 4,141,364 | 2/27/79 | Schultze | 128/207.15 |
| 4,164,045 | 9/14/79 | Bokros et al. | 623/1.28 |
| 4,214,587 | 7/29/80 | Sakura Jr. | 606/155 |
| 4,300,244 | 11/17/81 | Bokros | 623/1.13 |
| 4,313,231 | 2/2/82 | Koyamada | 623/1.32 |
| 4,319,363 | 3/16/82 | Ketharanathan | 623/1.47 |
| 4,425,908 | 1/17/84 | Simon | 128/899 |
| 4,441,215 | 4/10/84 | Kaster | 623/1.53 |
| 4,470,407 | 9/11/84 | Hussein | 600/108 |
| 4,501,264 | 2/26/85 | Rockey | 128/898 |
| 4,503,569 | 3/12/85 | Dotter | 623/1.19 |
| 4,512,338 | 4/23/85 | Balko et al. | 606/108 |
| 4,535,770 | 8/20/85 | Lemole | 606/108 |
| 4,550,447 | 11/5/85 | Seiler Jr. et al. | 623/1.32 |
| 4,553,545 | 11/19/85 | Maass et al. | 606/198 |
| 4,560,374 | 12/24/85 | Hammerslag | 604/509 |
| 4,580,568 | 4/8/86 | Gianturco | 606/198 |

UNITED STATES PATENT AND TRADEMARK OFFICE
CERTIFICATE OF CORRECTION

PATENT NO. : 6,896,696 B2
APPLICATION NO. : 09/957983
DATED : May 24, 2005
INVENTOR(S) : Burns Doran et al.

It is certified that error appears in the above-identified patent and that said Letters Patent is hereby corrected as shown below:

| | | | |
|---|---|---|---|
| 4,597,389 | 7/1/86 | Ibrahim et al. | 606/194 |
| 4,647,416 | 3/3/87 | Seiler Jr. et al. | 264/118 |
| 4,649,922 | 3/17/87 | Wiktor | 606/194 |
| 4,655,771 | 4/7/87 | Wallsten | 623/1.22 |
| 4,655,776 | 4/7/87 | Lesinski | 623/10 |
| 4,665,918 | 5/19/87 | Garza et al. | 606/108 |
| 4,681,110 | 7/21/87 | Wiktor | 606/194 |
| 4,693,721 | 9/15/87 | Ducheyne | 623/23.54 |
| 4,733,665 | 3/29/88 | Palmaz | 606/108 |
| 4,739,762 | 4/26/88 | Palmaz | 623/1.11 |
| 4,740,207 | 4/26/88 | Kreamer | 623/1.15 |
| 4,760,849 | 8/2/88 | Kropf | 606/191 |
| 4,762,128 | 8/9/88 | Rosenbluth | 606/192 |
| 4,771,773 | 9/20/88 | Kropf | 606/108 |
| 4,776,337 | 10/11/88 | Palmaz | 623/1.11 |
| 4,786,507 | 9/6/88 | Fischell et al. | |
| 4,769,029 | 9/6/88 | Patel | 623/1.32 |
| 4,787,899 | 11/29/88 | Lazarus | 623/1.11 |
| 4,795,458 | 1/3/89 | Regan | 623/1.19 |
| 4,795,465 | 1/3/89 | Marten | 623/9 |
| 4,800,882 | 1/31/89 | Gianturco | 606/194 |
| 4,820,298 | 4/11/89 | Leveen et al. | 623/1.18 |
| 4,830,003 | 5/16/89 | Wolff et al. | 606/191 |
| 4,842,575 | 6/27/89 | Hoffman Jr. et al. | 600/36 |
| 4,848,343 | 7/18/89 | Wallsten et al. | 606/194 |
| 4,851,009 | 7/25/89 | Pinchuk | 623/66.1 |
| 4,856,516 | 8/15/89 | Hillstead | 606/194 |
| 4,872,874 | 10/10/89 | Taheri | 128/898 |
| 4,877,030 | 10/31/89 | Beck et al. | 606/195 |
| 4,878,906 | 11/7/89 | Lindermann et al. | 623/3.18 |
| 4,886,062 | 12/12/89 | Wiktor | 606/194 |
| 4,913,141 | 4/3/90 | Hillstead | 623/1.11 |
| 4,922,905 | 5/8/90 | Strecker | 606/195 |
| 4,950,227 | 8/21/90 | Savin et al. | 623/1.12 |
| 4,950,258 | 8/21/90 | Kawai et al. | 604/530 |
| 4,994,071 | 2/19/91 | MacGregor | 606/194 |
| 5,015,253 | 5/14/91 | MacGregor | 623/1.15 |
| 5,019,090 | 5/28/91 | Pinchuk | 623/1.15 |
| 5,035,706 | 7/30/91 | Gianturco et al. | 606/198 |
| 5,037,392 | 8/6/91 | Hillstead | 606/194 |
| 5,059,211 | 10/22/91 | Stack et al. | 623/1.15 |
| 5,064,435 | 11/12/91 | Porter | 623/23.7 |
| 5,092,877 | 3/3/92 | Pinchuk | 128/898 |
| 5,102,417 | 4/7/92 | Palmaz | 606/195 |
| 5,104,399 | 4/14/92 | Lazarus | 623/1.14 |

UNITED STATES PATENT AND TRADEMARK OFFICE
CERTIFICATE OF CORRECTION

PATENT NO. : 6,896,696 B2
APPLICATION NO. : 09/957983
DATED : May 24, 2005
INVENTOR(S) : Burns Doran et al.

It is certified that error appears in the above-identified patent and that said Letters Patent is hereby corrected as shown below:

| | | | |
|---|---|---|---|
| 5,104,404 | 4/14/92 | Wolff | 623/1.16 |
| 5,108,415 | 4/28/92 | Pinchuk et al. | 606/194 |
| 5,108,417 | 4/28/92 | Sawyer | 623/1.22 |
| 5,122,154 | 6/16/92 | Rhodes | 623/1.13 |
| 5,133,732 | 7/28/92 | Wiktor | 623/1.22 |
| 5,135,536 | 8/4/92 | Hillstead | 606/195 |
| 5,139,480 | 8/18/92 | Hickle et al. | 604/8 |
| 5,147,385 | 9/15/92 | Beck et al. | 128/898 |
| 5,147,400 | 9/15/92 | Kaplan et al. | 623/13.18 |
| 5,158,548 | 10/27/92 | Lau et al. | 606/194 |
| 5,163,952 | 11/17/92 | Froix | 623/1.18 |
| 5,195,984 | 3/23/93 | Schatz | 623/1.2 |
| 5,197,978 | 3/30/93 | Hess | 623/1.18 |
| 5,217,483 | 6/8/93 | Tower | 623/1.15 |
| 5,226,913 | 7/13/93 | Pinchuk | 140/71R |
| 5,282,823 | 2/1/94 | Schwartz et al. | 623/1.22 |
| 5,282,824 | 9/1/94 | Gianturco | 623/1.13 |
| 5,292,331 | 3/8/94 | Boneau | 623/1.16 |
| 5,304,200 | 4/19/94 | Spaulding | 623/1.16 |
| 5,344,425 | 9/6/94 | Sawyer | 606/198 |
| 5,354,308 | 10/11/94 | Simon et al. | 623/1.15 |
| 5,354,309 | 10/11/94 | Schnepp-Pesch et al. | 606/198 |
| 5,383,892 | 1/24/95 | Cardon et al. | 623/1.16 |
| 5,405,377 | 4/11/95 | Cragg | 623/1.2 |
| 5,449,373 | 9/12/95 | Pinchasik et al. | 606/198 |
| 5,735,893 | 4/7/98 | Lau et al. | 623/1 |
| 5,741,327 | 4/21/98 | Frantzen | 623/1 |
| 5,755,771 | 5/26/98 | Penn et al. | 623/1 |
| 5,755,781 | 5/26/98 | Jayaraman | 623/1 |
| 5,755,776 | 5/26/98 | Al-Saadon | 623/1 |
| 5,776,161 | 7/7/98 | Globerman | 606/194 |
| 5,776,183 | 7/7/98 | Kanesaka et al. | 623/1 |
| 5,800,521 | 9/1/98 | Orth | 623/1 |
| 5,807,404 | 9/15/98 | Richter | 623/1 |
| 5,810,872 | 9/22/98 | Kanesaka et al. | 606/198 |
| 5,824,059 | 10/20/98 | Wijay | 623/1 |
| 5,836,966 | 11/17/98 | St. German | 606/198 |
| 5,855,600 | 1/5/99 | Alt | 623/1 |
| 5,868,780 | 2/9/99 | Lashinski et al. | 606/198 |
| 5,911,754 | 6/15/99 | Kanesaka et al. | 623/1 |
| 5,913,895 | 6/22/99 | Burpee et al. | 623/1 |
| 5,922,021 | 7/13/99 | Jang | 623/1 |
| 5,938,697 | 8/17/99 | Killion et al. | 623/1 |
| 5,948,016 | 9/7/99 | Jang | 623/1 |
| 5,954,743 | 9/21/99 | Jang | 606/198 |
| 6,017,365 | 1/25/00 | Von Oepen | 623/1 |

UNITED STATES PATENT AND TRADEMARK OFFICE
CERTIFICATE OF CORRECTION

PATENT NO. : 6,896,696 B2  Page 4 of 5
APPLICATION NO. : 09/957983
DATED : May 24, 2005
INVENTOR(S) : Burns Doran et al.

It is certified that error appears in the above-identified patent and that said Letters Patent is hereby corrected as shown below:

| | | | |
|---|---|---|---|
| 6,068,656 | 5/30/00 | Von Oepen | 623/1.17 |
| 6,129,755 | 10/10/00 | Mathis et al. | 623/1.15 |
| 6,179,867 | 1/30/01 | Cox | 623/1.15 |
| 6,183,506 | 2/6/01 | Penn et al. | 623/1.15 |
| 6,231,598 | 5/15/01 | Berry et al. | 623/1.15 |
| 6,245,102 | 6/12/01 | Jayaraman | 623/1.15 |
| 6,273,910 | 8/14/01 | Limon | 623/1.15 |
| 6,273,911 | 8/14/01 | Cox et al. | 623/1.15 |
| 6,511,505 | 1/28/03 | Cox et al. | 623/1.16 |
| 6,673,107 | 01/6/04 | Brandt et al. | 623/1.35 |
| 6,730,117 | 5/4/04 | Tseng et al. | 623/1.16-- |

Front page, after "FOREIGN PATENT DOCUMENTS", add the following:

| | |
|---|---|
| --EP 0 606 165 A1 | 7/13/94 |
| EP 0 796 597 A2 | 9/24/97 |
| EP 0 821 920 A1 | 2/4/98 |
| EP 0 876 806 A1 | 11/11/98 |
| JP 6-4175 | 3/6/94 |
| WO 94/17754 | 8/18/94 |
| WO 96/26689 | 9/6/96 |
| WO 97/04721 | 2/13/97 |
| WO 97/14375 | 2/24/97 |
| WO 97/25937 | 7/24/97 |
| WO 97/32543 | 9/12/97 |
| WO 97/32544 | 9/12/97 |
| WO 97/33534 | 9/18/97 |
| WO 97/40780 | 11/6/97 |
| WO 97/40781 | 11/6/97 |
| WO 97/40782 | 11/6/97 |
| WO 97/40783 | 11/6/97 |
| WO 97/40874 | 11/6/97 |
| WO 98/20810 | 5/22/98 |
| WO 99/44535 | 9/10/99-- |

UNITED STATES PATENT AND TRADEMARK OFFICE
CERTIFICATE OF CORRECTION

PATENT NO. : 6,896,696 B2
APPLICATION NO. : 09/957983
DATED : May 24, 2005
INVENTOR(S) : Burns Doran et al.

It is certified that error appears in the above-identified patent and that said Letters Patent is hereby corrected as shown below:

Column 4

On line 35 delete [10b] and insert therefore --110b--.

Column 16

On line 39 delete [WC] and insert therefore --$W_c$--.

Column 28

On line 64 delete the second instance of [4] and insert therefore --3--.

Column 29

On line 5 delete the second instance of [7] and insert therefore --6--.

On line 18 delete the second instance of [9] and insert therefore --8--.

On line 26 delete the second instance of [12] and insert therefore --11--.

On line 29 delete [9] and insert therefore --8--.

Signed and Sealed this

Fourth Day of July, 2006

JON W. DUDAS
*Director of the United States Patent and Trademark Office*